US010731127B2

(12) United States Patent
Li et al.

(10) Patent No.: US 10,731,127 B2
(45) Date of Patent: Aug. 4, 2020

(54) CHIMERIC ANTIGEN RECEPTORS TARGETING GPC3 AND USES THEREOF

(71) Applicant: Carsgen Therapeutics Limited, Shanghai (CN)

(72) Inventors: Zonghai Li, Shanghai (CN); Huiping Gao, Shanghai (CN); Hua Jiang, Shanghai (CN); Bizhi Shi, Shanghai (CN); Huamao Wang, Shanghai (CN); Kesang Li, Shanghai (CN); Hongyang Wang, Shanghai (CN); Shengli Yang, Shanghai (CN); Jianren Gu, Shanghai (CN)

(73) Assignee: CARsgen Therapeutics Limited, Shanghai (CN)

( * ) Notice: Subject to any disclaimer, the term of this patent is extended or adjusted under 35 U.S.C. 154(b) by 454 days.

(21) Appl. No.: 14/889,778

(22) PCT Filed: May 6, 2014

(86) PCT No.: PCT/CN2014/076913
§ 371 (c)(1),
(2) Date: Mar. 1, 2016

(87) PCT Pub. No.: WO2014/180306
PCT Pub. Date: Nov. 13, 2014

(65) Prior Publication Data

US 2016/0215261 A1 Jul. 28, 2016

(30) Foreign Application Priority Data

May 8, 2013 (CN) .......................... 2013 1 0164725

(51) Int. Cl.

| | |
|---|---|
| ***C07K 14/725*** | (2006.01) |
| ***C07K 16/28*** | (2006.01) |
| ***C12N 5/0783*** | (2010.01) |
| ***C07K 14/705*** | (2006.01) |
| ***C07K 16/18*** | (2006.01) |
| *A61K 39/00* | (2006.01) |

(52) U.S. Cl.
CPC ........ *C12N 5/0638* (2013.01); *C07K 14/7051* (2013.01); *C07K 14/70517* (2013.01); *C07K 14/70532* (2013.01); *C07K 16/18* (2013.01); *A61K 2039/5158* (2013.01); *C07K 2317/622* (2013.01); *C07K 2319/03* (2013.01); *C12N 2510/00* (2013.01); *C12N 2740/16043* (2013.01); *C12N 2840/20* (2013.01)

(58) Field of Classification Search
CPC ...... C07K 16/18; C07K 16/30; C07K 16/303; C07K 14/7051; C07K 14/70517; C07K 14/70521; C07K 2319/00; C07K 2319/03; C07K 2319/33; C07K 2319/70; C07K 2319/74; C12N 5/0636; C12N 5/0637; C12N 5/0638; C12N 2740/16041; C12N 2740/16043; C12N 2510/00
See application file for complete search history.

(56) References Cited

U.S. PATENT DOCUMENTS

| | | | | |
|---|---|---|---|---|
| 7,919,086 | B2 | 4/2011 | Nakano et al. | |
| 2007/0190599 | A1* | 8/2007 | Nakano ................ | C07K 16/303 435/69.1 |
| 2014/0170114 | A1* | 6/2014 | Kaplan ............ | G01N 33/57438 424/93.2 |
| 2017/0204177 | A1* | 7/2017 | Wang ..................... | A61K 48/00 |
| 2018/0201902 | A1* | 7/2018 | Wang .................. | C12N 5/0636 |

FOREIGN PATENT DOCUMENTS

| | | | |
|---|---|---|---|
| CN | 102702353 | A | 10/2012 |
| WO | 2008/045437 | A2 | 4/2008 |
| WO | 2010/025177 | A1 | 3/2010 |
| WO | 2012/145469 | A1 | 10/2012 |
| WO | 2012/156747 | A1 | 11/2012 |
| WO | 2013/070468 | A1 | 5/2013 |

OTHER PUBLICATIONS

Milone et al., Mol. Therapy 2009; 17:1453-1464.*
pWPT-Gfp, plasmid #12255; www.addgene.org/12255/; last visited Aug. 8, 2017.*
McGinley et al., Stem Cell Res & Therapy 2011: 2:12, pp. 1-12; doi:10.1186/scrt53.*
PCT International Search Report for International Application No. PCT/CN2014/076913 dated Aug. 19, 2014, English Translation, 7 pages.
Carpenito Carmine et al., "Control of large, established tumor xenografts with genetically retargeted human T cells containing CD28 and CD137 domains," Proceedings of the National Academy of Sciences, Mar. 3, 2009, vol. 106, No. 9, pp. 3360-3365.
Tamada Koji et al., "Redirecting Gene-Modified T Cells toward Various Cancer Types Using Tagged Antibodies," Clinical Cancer Research, Dec. 1, 2012, vol. 18, No. 23, pp. 6436-6445.
Ho Mitchell and Kim Heungnam, "Glypican-3: A new target for cancer immunotherapy," European Journal of Cancer, 2011, No. 47, pp. 333-338.
Li Yonghai et al., "Validation of glypican-3-specific scFv isolated from paired display/secretory yeast display library," BMC Biotechnology, 2012, vol. 12, No. 23, 10 pages.

(Continued)

*Primary Examiner* — Jessica H Roark
(74) *Attorney, Agent, or Firm* — Wilson Sonsini Goodrich & Rosati

(57) ABSTRACT

A nucleic acid encoding a chimeric antigen receptor expressed at surface of a T lymphocyte, said chimeric antigen receptor comprises, connected in the order of, an extracellular binding domain, a transmembrane region, and an intracellular signaling domain, wherein the extracellular binding domain comprises a single chain antibody, scFv (GPC3), which specifically recognizes the C-terminal epitope of GPC3. A genetically modified T lymphocyte having a chimeric antigen receptor expressed at surface thereof, and the chimeric antigen receptor is expressed by the nucleic acid described above.

19 Claims, 17 Drawing Sheets

Specification includes a Sequence Listing.

(56) References Cited

OTHER PUBLICATIONS

Sadelain Michel et al., "The Basic Principles of Chimeric Antigen Receptor Design," Cancer Discovery, Apr. 2013, vol. 3, pp. 388-398.
Hui Liu et al., "Synthesis of full length recombinant chimeric receptor anti-erbB2 scFv-CD28-ζ and construction of its eukaryotic expression vector," Journal of Chinese PLA Postgraduate Medical School, vol. 31, No. 4, Apr. 2010, pp. 360-362 (English Abstract).
An-sheng Bai et al., "Expression of Kinase Insert Domain-containing Receptor in Prostate Adenocarcinoma," National Journal of Andrology, vol. 13, No. 4, Apr. 2007, pp. 324-326 (English Abstract).
Yu Sawada et al., "Phase I Trial of a Glypican-3-Derived Peptide Vaccine for Advanced Hepatocellular Carcinoma: Immunologic Evidence and Potential for Improving Overall Survival," Clinical Cancer Research, vol. 18, No. 13, Jul. 1, 2012, pp. 3686-3696.
Huiping Gao et al., "Development of T Cells Redirected to Glypican-3 for the Treatment of Hepatocellular Carcinoma," Clinical Cancer Research, vol. 20, No. 24, Dec. 15, 2014, pp. 6418-6428.
Hartmann, et al., Unical development of CAR T cells—challenges and opportunities in translating innovative treatment concepts, EMBO Molecular Medicine, 2017, 9(9):1183-1197.
Wang, et al., The status and development of tumor microenvironment simulation platforms, Int. J Clin Exp. Pathol, 2017, 10(2):842-852.
Zhang, CAR T-cell therapy: opportunities and Challenges, Immunotherapy, 2016, 8(3):245-247.
European search report with written opinion dated Oct. 21, 2016 for EP Application No. 14794936.
Abou-Alfa, et al. Randomized phase II placebo controlled study of codrituzumab in previously treated patients with advanced hepatocellular carcinoma. J Hepatol. Aug. 2016;65(2):289-95. doi: 10.1016/j.jhep.2016.04.004. Epub Apr. 13, 2016.
Zhao, et al. Affinity maturation of T-cell receptor-like antibodies for Wilms tumor 1 peptide greatly enhances therapeutic potential. Leukemia. Nov. 2015;29(11):2238-47. doi: 10.1038/leu.2015.125. Epub May 19, 2015.

* cited by examiner

Mouse from empty vector control group

Mouse from GPC3-28BBZ group

Mouse from 2D3-28BBZ group

Mouse from GPC3-28BBZ group

CHIMERIC ANTIGEN RECEPTORS TARGETING GPC3 AND USES THEREOF

CROSS-REFERENCE TO RELATED APPLICATIONS

This application is a U.S. national phase application filed under 35 U.S.C. § 371 of International Application Number PCT/CN2014/076913, filed May 6, 2014, designating the United States, which claims priority from Chinese Application Number CN 201310164725.X, filed May 8, 2013, which are both hereby incorporated herein by reference in their entirety.

REFERENCE TO A SEQUENCE LISTING

The Sequence Listing associated with this application is filed in electronic format via EFS-Web and is hereby incorporated into the specification in its entirety. The name of the text file containing the Sequence Listing is "157923x1 amend ST25." The size of the text file is 100 KB, and the text file was created on Mar. 14, 2016.

TECHNICAL FIELD

This invention relates to the field of cell therapy for tumor, more specifically, relates to the field of genetically modified T lymphocyte therapy for epithelial-originated tumors with specific expression of GPC3.

BACKGROUND ART

Glypican-3 (GPC3, also known as DGSX, GTR2-2, MXR7, OCI-5, SDYS, SGB, SGBS or SGBS1) is a cell surface protein belonging to the glypican family of heparin sulfate proteoglycans. GPC3 gene encodes and produces a core protein precursor of about 70 kDa, the precursor protein can be cleaved by furin into a soluble amino terminal (N-terminal) peptide of about 40 kDa which is capable of entering blood, and a membrane binding carboxyl terminal (C-terminal) peptide of about 30 kDa containing 2 heparin sulfate chains. GPC3 protein is attached to the cell membrane by a glycosylphosphatidylinositol (GPI) anchor.

GPC3 is highly expressed in fetal liver and not expressed in normal adult liver tissue, but its expression is reactivated in hepatocellular carcinoma, and has a very close association with the development of liver cancer, the detection rate of GPC3 expression is relatively high during early stage of liver cancer and increases along with the development of liver cancer. Meanwhile, the expression of GPC3 is not detected in liver adenocarcinoma, cholangiocarcinoma, liver metastasis and 12 common solid tumors and 21 non-hepatoma cell lines. Furthermore, GPC3 is also expressed in tumors such as melanoma, ovarian clear cell carcinoma, yolk sac tumor, neuroblastoma and other tumors. Considering its specifically high expression in hepatocellular carcinoma, melanoma and other tumors, GPC3 is considered to be a candidate target for tumor immunotherapy.

There have been reports about liver cancer detection utilizing anti-GPC3 antibody and investigation programs on antibody-dependent cell-mediated cytotoxicity (ADCC) or complement dependent cytotoxicity (CDC) using anti-GPC3 antibody. Antibodies for therapeutic uses generally recognize the C-terminus of the GPC3 protein. However, antibody therapy is restrained by the in vivo half-life of antibody in blood circulation, which is mostly less than 23 days. Therefore, antibody therapy for tumor requires continued administration and/or increased dosage of administration, which would result in increased treatment cost to the patients, and in certain circumstances, may even lead to unwilling termination of treatment. Moreover, as an exogenous protein, therapeutic antibody may be associated with in vivo risk of causing allergic reaction and generating neutralizing-antibodies against said therapeutic antibody.

The role of T lymphocytes in immune response against tumor is gaining more and more attention. Adoptive immunotherapy based on T lymphocyte has achieved certain effects on some tumors, and such immunotherapy may overcome the above limitations of antibody therapy, but its efficacy on most tumors is still unsatisfactory (Grupp S A, et al., Adoptive cellular therapy, Curr Top Microbiol Immunol, 2011, 344:149-72). In recent years, enlightened by the finding that specific recognition of CTL towards target cells is dependent on T lymphocytes receptor (T Cell Receptor, TCR), scFv antibody against tumor associated antigen is fused with intracellular signal activation motif of T lymphocyte receptor such as CD3ζ or FcεRIγ into a chimeric antigen receptor (Chimeric Antigen Receptor, CAR), and presented at the surface of T lymphocyte through genetic modification by lentiviral transduction or similar means. Such CAR T lymphocytes can selectively direct to tumor cells and specifically kill tumor in a MHC-independent manner, where MHC stands for major histocompatibility complex. CAR T lymphocyte therapy is a novel immunotherapeutic strategy in the field of cancer immunotherapy (Schmitz M, et al., Chimeric antigen receptor-engineered T cells for immunotherapy of Cancer, J Biomed Biotechnol, 2010, doi: 10.1155/2010/956304).

Chimeric antigen receptor comprises an extracellular binding domain, a transmembrane region and an intracellular signaling domain. Generally, the extracellular domain comprises an scFv that is capable of recognizing a tumor-associated antigen, the transmembrane region employs the transmembrane region from molecules such as CD8, CD28 and the likes, and the intracellular signaling domain employs an immunoreceptor tyrosine-based activation motif (ITAM) CD3ζ or FcεRIγ and the intracellular signaling domain of co-stimulatory signaling molecule such as CD28, CD137, CD134 and the likes.

In the first generation CAR T lymphocyte, the intracellular signaling domain comprises ITAM only, and parts of the chimeric antigen receptor are connected in the form of scFv-TM-ITAM. Such CAR T can induce cellular cytotoxic effect against tumor, but the level of cytokines secreted is relatively low, and no sustaining anti-tumor effect could be induced in the body (Zhang T. et al., Chimeric NKG2D-modified T cells inhibit systemic T-cell lymphoma growth in a manner involving multiple cytokines and cytotoxic pathways, Can Res 2007, 67 (22): 11029-11036).

In the second generation CAR T lymphocyte that developed afterwards, an intracellular signaling domain of CD28 or CD 137 (also known as 4-1BB) is further included, and parts of the chimeric antigen receptor are connected in the form of scFv-TM-CD28-ITAM or scFv-TM-CD137-ITAM. Co-stimulatory effect of B7/CD28 or 4-1BBL/CD137 in the intracellular signaling domain induces sustained proliferation of T lymphocytes, and is capable of increasing the level of cytokines such as IL-2, IFN-γ and others secreted by T lymphocytes, as well as improving the in vivo survival period and the anti-tumor effect of the CAR T (Dotti G. et al., CD28 costimulation improves expansion and persistence of chimeric antigen receptor modified T cells in lymphoma patients J Clin Invest, 2011, 121 (5): 1822-1826).

In the third generation CAR T lymphocyte that developed in recent years, parts of the chimeric antigen receptor are connected in the form of scFv-TM-CD28-CD137-ITAM or scFv-TM-CD28-CD134-ITAM, the in vivo survival and the anti-tumor effect of the CART is further improved (Carpenito C, et al., Control of large established tumor xenografts with genetically retargeted human T cells containing CD28 and CD 137 domains, PNAS, 2009, 106(9): 3360-3365).

Besides the attractive prospect of CAR T lymphocyte in tumor immunotherapy, some potential risks shall be taken into account. For instance, certain normal tissues may exhibit low expression of specific antigen to be recognized by the CAR, this may results in damage by CAR T lymphocytes to such normal tissues. For example, treatment against carbonic anhydrase IX, the antigen expressed in tumor cells of patients having renal cell carcinoma, is the first reported case of clinical application of adoptive therapy with CAR T lymphocytes, which is also the first case reporting on-target off-tumor effect of CAR T lymphocytes. After multiple administrations of CAR T lymphocytes, patients developed liver toxicity of grades 2-4. Upon analysis, the cause is believed to be the CAIX expression in a low level on bile duct epithelial cells, this clinical trial was discontinued while assessment about therapeutic outcomes in patients are excluded (Stoter G. et al., Treatment of metastatic renal cell carcinoma with autologous T-lymphocytes genetically retargeted against carbonic anhydrase IX: first clinical experience, J din oncol, 2006, 24 (13): e20-e22; Ngo M C, et al., Ex vivo gene transfer for improved adoptive immunotherapy of cancer Human Molecular Genetics, 2011, R1_R7). Furthermore, the excessive co-stimulation signal in CAR may reduce the threshold required for activating effector cells, such that genetically modified T lymphocyte may be activated at conditions of rather low level of antigen or at the absence of antigen pulse, and resulting in the release of large amount of cytokines which may induce so-called "cytokine storm". This signal leakage will cause off-target cytotoxicity, resulting in non-specific tissue damage. For example, sudden death of a patient caused by such "cytokine storm" induced by low Her2 expression in normal lung tissue was observed during a clinical treatment using a third-generation CAR T cells targeting Her2 for patients having advanced colorectal cancer with liver and lung metastasis (Morgan R A, et al., Report of a serious adverse event following the administration of T cells transduced with a chimeric antigen receptor recognizing Erbb2 Molecular Therapy, 2010, 18 (4): 843-851).

Therefore, a strong need exists in the art for a tumor treatment regimen using lymphocyte encoding GPC3-specific chimeric antigen receptor while overcoming the above defects.

BRIEF DESCRIPTION OF THE INVENTION

In a first aspect, the present invention relates to a nucleic acid encoding a GPC3 chimeric antigen receptor for expression at the surface of a T lymphocyte. The chimeric antigen receptor expressed thereby provides the T lymphocyte which expresses said receptor with a highly specific cytotoxicity against tumor cells with high GPC3 expression. The GPC3 chimeric antigen receptor comprises, connected in the order of, an extracellular binding domain, a transmembrane region, and an intracellular signaling domain, wherein the extracellular binding domain comprises a single chain antibody, scFv(GPC3), which specifically recognizes the C-terminal epitope of GPC3. The extracellular binding domain of said chimeric antigen receptor binds to the transmembrane region of CD8 or CD28 through the hinge region of CD8, and connected immediately after the transmembrane region is the intracellular signaling domain.

Nucleic acid sequences of the present invention may be in the form of DNA or RNA. DNA includes cDNA, genomic DNA or synthetic DNA. DNA can be single-stranded or double-stranded. DNA may be coding strand or non-coding strand. In this invention, nucleic acid codons encoding amino acid sequence of the chimeric antigen receptor can be degenerate, that is, multiple degenerate nucleic acid sequences encoding the same amino acid sequence are all included within the scope of the present invention. Degenerate nucleic acid codons encoding corresponding amino acids are well-known in the art. The present invention also relates to variants of the polynucleotides described above, such variant encodes a polypeptide having the same amino acid sequence as the polypeptide of the present invention, or a fragment, analog and derivative thereof. Such polynucleotide variants can be allelic variants occurred naturally or variants occurred non-naturally. Such nucleotide variants include substitution variants, deletion variants and insertion variants. As known in the art, an allelic variant is an alternate form of a polynucleotide, it may contain one or more nucleotide substitutions, deletions or insertions, but the function of the encoded polypeptide is not materially changed.

The present invention also relates to a polynucleotide hybridizes to the polynucleotide described above, provided that the two sequences having at least 50%, preferably at least 70%, more preferably at least 80%, most preferably at least 90% or at least 95% identity. Particularly, the present invention relates to a polynucleotide hybridizes to the polynucleotide of the present invention under stringent conditions. In the present invention, the term "stringent conditions" refers to: (1) hybridization and washing at low ionic strength and high temperature, such as 0.2×SSC, 0.1% SDS, 60° C.; or (2) hybridization at the presence of a denaturing agent, such as 50% (v/v) formamide, 0.1% calf serum/0.1% Ficoll, 42° C. and the like; or (3) hybridization occurs only when identity between two sequences is at least 90% or more, preferably 95% or more. Moreover, the polynucleotide capable of hybridization encodes a polypeptide having the same biological function and activity as the mature polypeptide as shown in SEQ ID NOs: 22-25.

Monoclonal antibodies specifically recognize C-terminal epitope of human GPC3 have been described in, for example, CN101186650A (Chugai); meanwhile, according to literature, Advances in Liver Cancer Antibody Therapies: A Focus on Glypican-3 and Mesothelin, BioDrugs 2011 Oct. 1; 25 (5):275-284, other monoclonal antibodies specifically recognize C-terminal epitope, including GC33 and hGC33, are also reported respectively, targeting GPC3 antigenic determinant positioned at C-terminal 524-563 amino acid residues, also reported are monoclonal antibodies GPC3-C02, 1G12 and others. These monoclonal antibodies as disclosed can be used in the preparation of the single chain antibody portion of the nucleic acid encoded chimeric protein antigen receptor of the present invention. Other monoclonal antibodies which recognize C-terminal epitope of GPC3 may also be used in the present invention by a suitable manner.

Single-chain antibody scFv(GPC3) can be prepared by genetic engineering or chemical synthesis based on the sequence of GPC3 monoclonal antibodies described above. In the present invention, the term "Single-chain antibody, scFv" refers to a fragment of antibody defined as follows, a recombinant protein comprises a heavy chain variable domain (VH) and a light chain variable domain (VL) connected by a linker, which brings these two domains into association such that an antigen-binding site is formed. Typically, scFv size is ⅙ the size of an intact antibody. ScFv is preferably an amino acid chain having a sequence encoded by a nucleotide chain. The scFv used in this invention may be further modified by routine techniques known in the art, separately or in combination, such as amino acid deletions, insertions, substitutions, additions, and/or recombination and/or other modification methods. Methods for introducing such modifications into the DNA sequence for an antibody according to its amino acid sequence are well known in the art; see, e.g., Sambrook, Molecular Cloning: A Laboratory Manual, Cold Spring Harbor Laboratory (1989) N.Y. Preferably, said modification is conducted at the nucleic acid level. The single-chain antibody may also include derivatives thereof. In this invention, when "antibody derivative" includes, for example, derivatives obtained by phage display technology, the ratio of phage antibodies binding to GPC3 epitope can be increased using techniques such as surface plasmon resonance used in BIAcore system (Schier, Human Antibody Hybridomas, 7(1996), 97-105; Malmborg, J. Immunol. Methods, 183(1995), 7-13). Further included are antibody derivatives generated by, for example, the method described in WO 89/09622 for production of chimeric antibodies, the method described in EP-A10239400 and WO90/07861 for producing humanized antibodies, the methods described in WO91/10741, WO94/02602 and WO96/33735 for generating xenogeneic antibodies, such as human antibodies produced in mouse.

The term "specific recognition" used in the present invention means that the antibody or scFv of this invention does not or does not substantially cross-react with any polypeptide other than the target antigen. The level of its specificity can be assessed by immunological techniques, including but not limited to, immunoblotting, immunoaffinity chromatography, flow cytometry analysis, etc. In the present invention, the specific recognition is preferably determined by flow cytometry, while criteria for specific recognition under particular circumstance can be decided by those of ordinary skill in the art based on common knowledge in the art.

The transmembrane region of the chimeric antigen receptor may be selected from the transmembrane region of proteins such as CD8 or CD28. CD8 or CD28 is a natural marker on surface of T lymphocytes. Human CD8 protein is a heterodimer comprising two chains, αβ or γδ. In an embodiment of the present invention, the transmembrane region is selected from the transmembrane region of CD8α or CD28. Furthermore, hinge region of CD8α is a flexible region, therefore, the transmembrane region of CD8 or CD28 is used along with the hinge region to connect the target recognition domain scFv and the intracellular signaling domain of the chimeric antigen receptor.

The intracellular signaling domain can be selected from the intracellular signaling domain of CD3ζ, FcεRIγ, CD28, CD137, CD134 proteins, and combinations thereof. CD3 molecule consists of five subunits, wherein the CD3ζ subunit (also known as CD3 zeta, abbreviated Z) containing 3 ITAM motifs, said motif is an important signal transduction segment in TCR-CD3 complex. CD3δZ (hereinafter referred to as DZ), a truncated CD3ζ sequence having no ITAM motif, is a construct generally used as a negative control in practice of the present invention. FcεRIγ, mainly distributed at surface of mast cells and basophils, contains one ITAM motif, and is similar to CD3ζ in structure, distribution and function. Moreover, as mentioned previously, CD28, CD137, CD134 are costimulatory signaling molecules, the costimulatory effect caused by the intracellular signaling domain therein upon complexing with the respective ligands may cause sustaining proliferation of T lymphocytes, can increase the level of cytokines such as IL-2 and IFN-γ secreted by the T lymphocytes, as well as improve in vivo survival period and antitumor effects of CAR T lymphocytes.

The GPC3 chimeric antigen receptor encoded by nucleic acid according to the present invention may be selected from chimeric antigen receptors being connected in the orders as following:

scFv(GPC3)-CD8-CD3ζ, scFv(GPC3)-CD8-CD137-CD3ζ, scFv(GPC3)-CD28a-CD28b-CD3ζ, scFv(GPC3)-CD28a-CD28b-CD137-CD3ζ, and combinations thereof, wherein in applicable chimeric antigen receptors, CD28a represents the transmembrane region of CD28 molecule, and CD28b represents the intracellular signaling domain of CD28 molecule. The GPC3-targeting chimeric antigen receptors provided above are collectively referred to as scFv(GPC3)-CAR.

In an embodiment of the invention, the nucleic acid of the present invention has a sequence as set forth in SEQ ID NOs: 18 to 21. In another embodiment of the present invention, the nucleic acid of the present invention is a nucleic acid encoding the chimeric antigen receptor selected from one of SEQ ID NOs: 22-25.

In a second aspect, the present invention includes a vector comprising the nucleic acid encoding the chimeric antigen receptor expressed on surface of T lymphocytes. In a specific embodiment, the vector used in the present invention is a lentivirus vector pWPT-eGFP. This plasmid is a third generation self-inactivating lentivirus vector system consisting of three plasmids, which are: a packaging plasmid psPAX2 encoding protein Gag/Pol and encoding Rev protein; an envelope plasmid PMD2.G encoding VSV-G protein; and an empty vector pWPT-eGFP, which may be used for the recombinant introduction of the object nucleic acid sequence, i.e. a nucleic acid sequence encoding the CAR. In the empty vector pWPT-eGFP (which itself acts as a mock vector in subsequent tests), an elongation factor-1α (EF-1α) promoter regulates the expression of enhanced green fluorescent protein (eGFP). The recombinant expression vector pWPT-eGFP-F2A-CAR comprising the object nucleic acid sequence encoding the CAR achieves the co-expression of eGFP and CAR through the ribosomal skipping sequence 2A (abbreviated as F2A) from food-and-mouth disease virus (FMDV). In a specific embodiment, the vector of the present invention comprises a nucleic acid sequence as set forth in one of SEQ ID NOs: 27-30.

In a third aspect, the present invention includes a virus comprising the vector described above. The virus of the present invention includes packaged virus with the ability to infect, and also includes virus yet to be packaged while containing essential components for packaging into infectious virus. Other viruses transducing T lymphocytes and the corresponding plasmid vectors that known in the art may also be used in the present invention.

In an embodiment of the present invention, the virus is a lentivirus containing the pWPT-eGFP-F2A-CAR recombinant vector (i.e., containing scFv(GPC3)-CAR) as described above.

In a fourth aspect, the present invention includes a genetically modified T lymphocyte, which is transduced with the nucleic acid of this invention or transduced with a recombinant plasmid comprising the nucleic acid as described above, or comprises a virus containing said plasmid. Conventional nucleic acid transfection methods in the art, including non-viral and viral transfection, are all suitable for use in the present invention. Non-viral transfection methods include electroporation and transposon approach. Recently, Amaxa has developed a nucleofection instrument, Nucleofector, which can directly introduce exogenous gene into cell nucleus to achieve effective transfection of target gene. In addition, transposon systems based on transporon such as Sleeping Beauty transposon (Sleeping Beauty system) or PiggyBac transposon exhibit substantially improved transduction efficiency than of general electroporation, the employment of Nucleofector transfection instrument in combination with Sleeping Beauty transposon system has been reported (Davies J K, et al., Combining CD 19 redirection and alloanergization to generate tumor-specific human T cells for allogeneic cell therapy of B-cell malignancies, Cancer Res, 2010, 70(10): OF1-10), which not only provides a higher transduction efficiency, but also is capable of achieving directed incorporation of target gene. In an embodiment of the present invention, the T lymphocyte modified with the chimeric antigen receptor gene is obtained by a transfection approach based on virus, such as retrovirus or lentivirus. Such approach has advantages including high transfection efficiency, capability of achieving stable expression of exogenous gene, and ability to shorten the time required for in vitro culture of lymphocytes to an amount meeting clinical demand, etc. At the surface of the genetically modified T lymphocyte, the transfected nucleic acid is expressed through transcription, and translation. As demonstrated by in vitro cytotoxicity assays towards various cultured tumor cells, genetically modified T lymphocytes of the present invention expressing chimeric antigen receptor at surface possess tumor cell killing effects (also known as cytotoxicity) of high specificity. Accordingly, the nucleic acid encoding the chimeric antigen receptor, the plasmid conprising the nucleic acid, the virus comprising the plasmid, and the genetically modified T lymphocyte transfected with said nucleic acid, plasmid or virus of the present invention can be effectively used for tumor immunotherapy.

In one embodiment, the lymphocyte of the present invention expresses a chimeric antigen receptor at its surface, said chimeric antigen receptor is encoded and expressed by a nucleic acid as set forth by one of SEQ ID NOs: 18-21. In another embodiment, the genetically modified T lymphocyte of the present invention expresses a chimeric antigen receptor at its surface, said chimeric antigen receptor has an amino acid sequence selected from one of SEQ ID NOs: 22-25.

DETAILED DESCRIPTION OF SPECIFIC EMBODIMENTS

Figure 1:
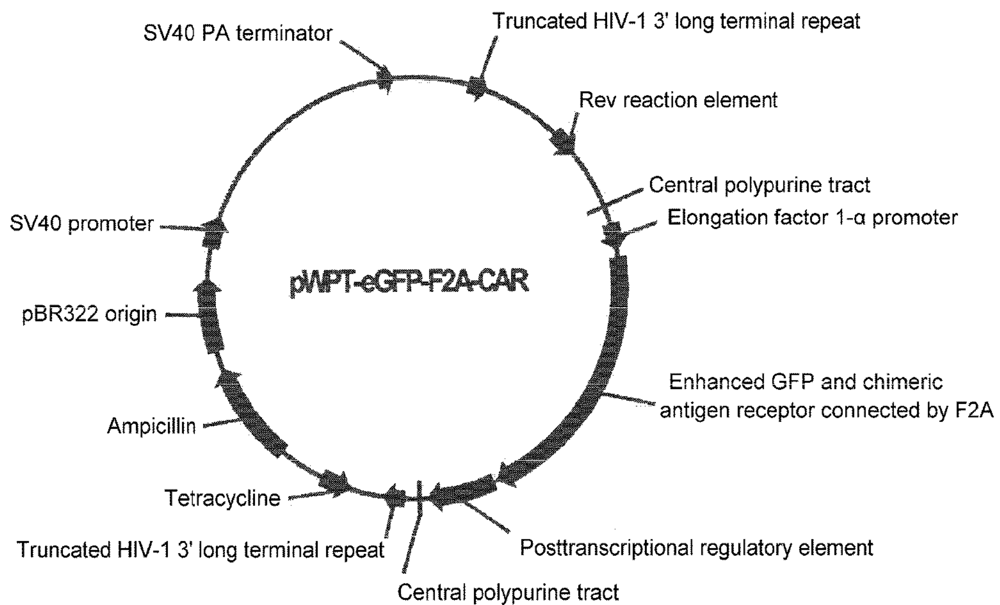
FIG. 1 shows the schematic structure of pWPT-eGFP-F2A-CAR, an exemplified lentivirus vector comprising a CAR coding sequence of the present invention.

This invention is further illustrated below with reference to specific examples. It should be understood that these examples are merely illustrative of the present invention without intending to limit the scope of the invention. In the following Examples, if not specifically indicated, experimental process was conducted with conditions in accordance with conventional conditions, such as those described by Sambrook et al. in Molecular Cloning: A Laboratory Manual (New York: Cold Spring Harbor laboratory Press, 1989), meanwhile, when a manufacturer's instruction is explicitly mentioned in an Example, the condition(s) recommended such instruction shall be followed.

Example 1. Construction of Lentiviral Plasmid Expressing the Chimeric Antigen Receptor of this Invention, and Virus Packaging Table 1 below provides exemplified order of connecting various parts of the chimeric antigen receptor of this invention, the illustration shown in FIG. 2 could be referred to for such connection as well.

TABLE 1

| Chimeric antigen receptor | Extracellular binding domain - transmembrane region - intracellular signaling domain 1 - intracellular signaling domain 2 etc | Description |
|---|---|---|
| GPC3-δZ | scFv(GPC3)-CD8-CD3δzeta | Negative Control |
| GPC3-Z | scFv(GPC3)-CD8-CD3 zeta | 1st generation |
| GPC3-BBZ | scFv(GPC3)-CD8-CD137-CD3 zeta | 2nd generation |
| GPC3-28Z | scFv(GPC3)-CD28a-CD28b-CD3 zeta | 2nd generation |
| GPC3-28BBZ | scFv(GPC3)-CD28a-CD28b-CD137-CD3 zeta | 3rd generation |
| 2D3-28BBZ | 2D3-CD28a-CD28b-CD137-CD3 zeta | 3rd generation |

1. Amplification of Nucleic Acid Fragment (1) Amplification of scFv (GPC3) Sequence The sequence of scFv (GPC3) was amplified using nucleotide GPC3/CD3 for bifunctional single-chain antibody constructed in our laboratory as the template, the sequence of the template is described in Chinese patent application 201210480326.x by SEQ ID NO: 9 therein. Amplification primers used for amplification of scFv (GPC3) are, upstream primer: 5'-gatgttgtgatgactcagtctc-3, (SEQ ID NO: 1), and downstream primer: 5'-gcgctggcgtcgtggttgaggagacggtgaccag-3' (SEQ ID NO: 2); all amplified bands were 746 bp in size. PCR amplification conditions were: initial denaturation at 94° C. for 4 min; denaturation at 94° C. for 40 s, annealing at 58° C. for 40 s, and extension at 68° C. for 40 s, for 25 cycles; followed by final elongation at 68° C. for 10 min. PCR result was confirmed by amplified band of expected fragment size on agarose gel electrophoresis.

(2) Nucleic Acid Sequences for Other Parts of the Chimeric Receptor Antigen

Nucleic acid sequences for parts of the chimeric receptor antigen other than scFv(GPC3) were obtained by PCR using SEQ ID NOs: 1-4 as disclosed in Patent Application No. 201310108532.2 as template, respectively. In particular, besides the scFv(GPC3) for the CAR, the following parts for the GPC3 chimeric antigen receptor were amplified, for CD8-CD3ζ (Z) and CD28a-CD28b-CD137-CD3ζ (28BBZ), scFv(EFGR)-CD8-CD3ζ (disclosed as SEQ ID NO: 1 in Patent Application 201310108532.2) and ScFv(EFGR)-CD28a-CD28b-CD137-CD3ζ (disclosed as SEQ ID NO: 2 in Patent Application 201310108532.2) were used respectively as the template, while using forward primer 5'-accacgacgccagcgccgcgaccac-3' (SEQ ID NO: 3) and downstream primer 5'-gaggtcgacctagcgagggggcagggcctgcatgtgaag-3' (SEQ ID NO: 4), PCR amplification conditions were: initial denaturation at 94° C. for 4 min; denaturation at 94° C. for 40 s, annealing at 60° C. for 40 s, and extension at 68° C. for 40 s, for 25 cycles; followed by final elongation at 68° C. for 10 min. Target bands are of 549 bp and 816 bp, respectively; PCR results were confirmed by amplified bands of expected fragment size on agarose gel electrophoresis.

In addition, CD8-CD3 delta ζ (delta Z, abbreiviated δZ), CD8-CD137-CD3ζ (BBZ) and CD28a-CD28b-CD3ζ (28Z) were obtained as following, respectively:

A) 1 ml of Trizol reagent (Invitrogen) was added into $1\times10^7$ healthy human peripheral blood mononuclear cells (provided by Shanghai Blood Center) to lyse the cells, then total RNA was isolated by phenol-chloroform extraction, and reverse transcribed using reverse transcription kit ImProm-IFM (Promega) to prepare cDNA. Using the cDNA prepared thereby as template, the followings were conducted respectively:

(i) CD8α hinge region—transmembrane region was obtained by amplification using upstream primer 5'-gtcaccgtctcctcaaccacgacgccagcg-3' (SEQ ID NO: 5) and downstream primer 5'-ggtgataaccagtgacaggag-3' (SEQ ID NO: 6), PCR amplification conditions were: initial denaturation at 94° C. for 4 min; denaturation at 94° C. for 30 s, annealing at 58° C. for 30 s, and extension at 68° C. for 30 s, for 25 cycles; followed by final elongation at 68° C. for 10 min. Target band has a theoretical size of 198 bp; amplified product was confirmed of being consistent with the theoretical size by agarose gel electrophoresis.

(ii) CD8α hinge region—transmembrane region—delta Z (i.e., CD8-CD3 delta ζ) was obtained by amplification using upstream primer 5'-gtcaccgtctcctcaaccacgacgccagcg-3' (SEQ ID NO: 5) and downstream primer 5'-gaggtcgacctacgcgggggcgtctgcgctcctgctgaacttcactctggtgataaccagtg-3' (SEQ ID NO: 7), PCR amplification conditions were the same as described above. Target band has a theoretical size of 261 bp; amplified product was confirmed of being consistent with the theoretical size by agarose gel electrophoresis.

(iii) CD28 transmembrane region—intracellular signaling domain was obtained by amplification using upstream primer 5'-ttttgggtgctggtggtggttgg-3' (SEQ ID NO: 8) and downstream primer 5'-gctgaacttcactctggagcgataggctgcgaag-3' (SEQ ID NO: 9), PCR amplification conditions were the same as described above. Target band has a theoretical size of 219 bp; amplified product was confirmed of being consistent with the theoretical size by agarose gel electrophoresis.

(iiii) CD137 intracellular domain was obtained by amplification using upstream primer 5'-aaacggggcagaaagaaactc-3' (SEQ ID NO: 10) and downstream primer 5'-cagttcacatcctccttc-3' (SEQ ID NO: 11), PCR amplification conditions were the same as described above. Target band has a theoretical size of 126 bp; amplified product was confirmed of being consistent with the theoretical size by agarose gel electrophoresis.

(iiiii) CD3 zeta signaling domain was obtained by amplification using upstream primer 5'-cactggttatcaccagagtgaagttcagcaggagc-3' (SEQ ID NO: 12) and downstream primer 5'-gaggtcgacctagcgagggggcagggcctgcatg-3' (SEQ ID NO: 13), PCR amplification conditions were the same as described above. Target band has a theoretical size of 339 bp; amplified product was confirmed of being consistent with the theoretical size by agarose gel electrophoresis.

B) Assembly of Nucleic Acid Fragments (i) CD8α hinge region—CD28 transmembrane region was assembled using upstream primer 5'-accacgacgcca-gcgccg-3, (SEQ ID NO: 14) and downstream primer 5'-cac-ccagaaaataataaag-3' (SEQ ID NO: 15), assembling conditions were: initial denaturation of CD8 a hinge region (50 ng)+CD28 transmembrane region (50 ng) at 94° C. for 4 min; denaturation at 94° C. for 30 s, annealing at 60° C. for 30 s, extension at 68° C. for 30 s, for 5 cycles; followed by elongation at 68° C. for 10 min; following addition of DNA polymerase as well as upstream and downstream primers were 25 cycles of PCR amplification, amplification conditions were: initial denaturation at 94° C. for 4 min; denaturation at 94° C. for 30 s, annealing at 60° C. for 30 s, and extension at 68° C. for 30 s, for 25 cycles; followed by final elongation at 68° C. for 10 min. The theoretical size is 216 bp. Amplified product was confirmed of being consistent with the theoretical size by agarose gel electrophoresis.

(ii) CD137-CD3ζ, i.e. BBZ, was obtained by assembly and amplification using upstream primer 5'-aaacggggca-gaaagaaactc-3' (SEQ ID NO: 10) and downstream primer 5'-gaggtcgacctagcgagggggcagggcctgcatg-3' (SEQ ID NO: 13), the assembly and amplification conditions were the same as described above. The theoretical size is 478 bp. Amplified product was confirmed of being consistent with the theoretical size by agarose gel electrophoresis.

(iii) CD8α hinge region—transmembrane region and BBZ were assembled and PCR amplified to obtain the target fragment, CD8α hinge region—transmembrane domain—BBZ intracellular domain, i.e., CD8-CD137-CD3ζ, wherein primers used were upstream primer 5'-gtcaccgtctcctcaaccac-gacgccagcg-3' (SEQ ID NO: 5) and downstream primer 5'-gaggtcgacctagcgagggggcagggcctgcatg-3' (SEQ ID NO: 13), the assembly and amplification conditions were the same as described above. The theoretical size is 691 bp. Amplified product was confirmed of being consistent with the theoretical size by agarose gel electrophoresis.

(iiii) CD8α hinge region—CD28 transmembrane region—intracellular domain and Z were assembled and PCR amplified as above to obtain the target fragment, CD8α hinge region—CD28 transmembrane region—28Z intracellular domain, namely CD28a-CD28b-CD3ζ, wherein primers used were upstream primer 5'-gtcaccgtctcctcaaccac-gacgccagcg-3' (SEQ ID NO: 5) and downstream primer 5'-gaggtcgacctagcgagggggcagggcctgcatg-3' (SEQ ID NO: 13), the assembly and amplification conditions were the same as described above. The theoretical size is 706 bp. Amplified product was confirmed of being consistent with the theoretical size by agarose gel electrophoresis.

(3) Obtaining eGFP Nucleic Acid Fragment Having F2A and CD8α Signal Peptide at 3' End Utilizing pWPT-eGFP-F2A-806-Z disclosed in Patent Application 201310108532.2 as template, eGFP nucleic acid fragment having F2A and CD8α signal peptide at 3' end was amplified using upstream primer 5'-cttacgcgtcctagcgctaccg-gtcgccaccatggtgagcaagggcgaggag-3' (SEQ ID NO: 16) and downstream primer 5'-cggcctggcggcgtggagcag-3'(SEQ ID NO: 17), PCR amplification conditions were: initial denaturation at 94° C. for 4 min, denaturation at 94° C. for 40 s, annealing at 56° C. for 40 s, extension at 68° C. for 50 s, for 25 cycles; followed by final elongation at 68° C. for 10 min. The theoretical size is 883 bp. Amplified product was confirmed of being consistent with the theoretical size by agarose gel electrophoresis.

2. Assembly of Nucleic Acid Fragments

Figure 2:
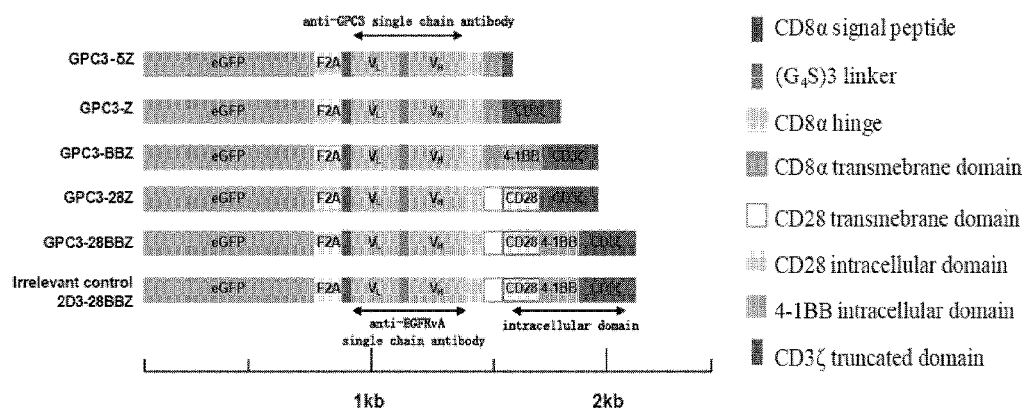
FIG. 2 shows a schematic view of an exemplified connection between the different fragments of the CAR of the present invention, wherein the eGFP and scFv (GPC3) specific chimeric antigen receptor are connected via the ribosomal skipping sequence F2A.

Amplified fragments CD8-CD3ζ, CD8-CD137-CD3ζ, CD28a-CD28b-CD3ζ, CD28a-CD28b-CD137-CD3ζ prepared as described above in subsection "(2) Nucleic acid sequences for other parts of the chimeric receptor antigen" were respectively assembled with equimolar of eGFP nucleic acid fragment having F2A and CD8α signal peptide at 3' end (approx. 50 ng) prepared as described above in subsection "(3) Nucleic acid sequences for other parts of the chimeric receptor antigen" and equimolar of scFv(GPC3) (approx. 50 ng), the three fragments were assembled following the pattern shown in FIG. 2 and PCR amplified, assembling conditions were: initial denaturation at 94° C. for 4 min; denaturation at 94° C. for 40 s, annealing at 60° C. for 40 s, extension at 68° C. for 140 s, for 5 cycles; followed by elongation at 68° C. for 10 min; following addition of DNA polymerase as well as upstream primer 5'-cttacgcgtcctagcgctaccggtcgccaccatggtgagcaagggcgag-gag-3' (SEQ ID NO:16) and downstream primer 5'-gaggtc-gacctagcgagggggcagggcctgcatg-3' (SEQ ID NO:13) were 25 cycles of PCR amplification, amplification conditions were: initial denaturation at 94° C. for 4 min; denaturation at 94° C. for 40 s, annealing at 60° C. for 40 s, and extension at 68° C. for 140 s, for 25 cycles; followed by final elongation at 68° C. for 10 min. The theoretical sizes of the amplified eGFP-GPC3-Z, eGFP-GPC3-BBZ, eGFP-GPC3-28Z and eGFP-GPC3-28BBZ are 2161 bp, 2278 bp, 2302 bp, and 2428 bp, respectively. Amplified products were confirmed of being consistent with the corresponding theoretical sizes by agarose gel electrophoresis.

Using the same experimental conditions as described above without addition of eGFP nucleic acid fragment having F2A and CD8α signal peptide at 3' end (approx. 50 ng), GPC3 chimeric antigen receptor encoding nucleic acid sequences GPC3-Z (SEQ ID NO: 18), GPC3-BBZ (SEQ ID NO: 19), GPC3-28Z (SEQ ID NO: 20) and GPC3-28BBZ (SEQ ID NO: 21) could be obtained using upstream primer 5'-gatgttgtgatgactcagtctc-3' (SEQ ID NO: 1) and downstream primer 5'-gaggtcgacctagcgagggggcagggcctgcatg-3' (SEQ ID NO: 13), these encoding nucleic acid sequences respectively encode the GPC3 chimeric antigen receptors having the following amino acid sequences, GPC3-Z (SEQ ID NO: 22), GPC3-BBZ (SEQ ID NO: 23), GPC3-28Z (SEQ ID NO: 24) and GPC3-28BBZ (SEQ ID NO: 25).

In addition, amplified fragment CD8-CD3ζ delta prepared as described above in subsection "(2) Nucleic acid sequences for other parts of the chimeric receptor antigen" was assembled with equimolar of the fragment prepared as described above in subsection "(3) Nucleic acid sequences for other parts of the chimeric receptor antigen" and equimolar of scFv(GPC3) using upstream primer 5'-cttacgcgtc-ctagcgctaccggtcgccaccatggtgagcaagggcgaggag-3' (SEQ ID NO: 16) and downstream primer 5'-gaggtcgac-ctacgcgggggcgtctgcgctcctgctgaacttcactctggtgataaccagtg-3' (SEQ ID NO: 7) by assembling and PCR amplification under the same condition as described above to obtain eGFP-GPC3-δ Z (SEQ ID NO: 31). The theoretical size is 1858 bp. Amplified product was confirmed of being consistent with the theoretical size by agarose gel electrophoresis.

2-1. Construction of Lentiviral Vector Encoding Sham Control 2D3-28BBZ CAR (Namely, pWPT-eGFP-F2A-2D3-28BBZ)

A. Obtaining Nucleic Acid Fragment for 2D3 Single Chain Antibody Against the Intracellular Region Polypeptide (WTE) of a Novel EGFR Variant, EGFRvA Using mRNA from 2D3 hybridoma cell lines (prepared by Shanghai Raygene biotechnology Co., Ltd.) against WTE polypeptide as template, first strand cDNA was synthesized by reverse transcription using RT-PCR kit. The first strand cDNA was used as template for amplification of VH and VL genes using Heavy Primers and Light Primer Mix as the primers (both purchased from Shanghai Raygene biotechnology Co., Ltd.), respectively, PCR conditions were: initial denaturation at 94° C. for 4 min; denaturation at 94° C. for 40 s, annealing at 55° C. for 40 s, and extension at 68° C. for 40 s, for 30 cycles; followed by final elongation at 68° C. for 7 min. The PCR product was detected by agarose gel electrophoresis, and VH, VL fragments were recovered using gel extraction kit.

Then VH, VL fragments were further used as templates for assembling VH and VL fragments into scFv by overlap PCR using Linker-Primer Mix for primers (purchased from Shanghai Raygene biotechnology Co., Ltd.), PCR conditions were: denaturation at 94° C. for 1 min, annealing and extension at 63° C. for 4 min, for a total of 7 cycles. After 7 cycles, into a reaction system of 50 μl were supplemented with Linker-Primer Mix, polymerase buffer and $ddH_2O$, and proceeded with PCR. PCR conditions were: initial denaturation at 94° C. for 4 min, denaturation at 94° C. for 40 s, annealing at 58° C. for 40 s, extension at 68° C. for 1 min, for 30 cycles, then final elongation at 68° C. for 7 min. The PCR product was detected by agarose gel electrophoresis, and the scFv fragment was recovered using gel extraction kit.

B. Expression and Activity Assay of 2D3 Single Chain Antibody Against WTE Polypeptides The scFv fragment obtained above and pCANTAB 5E vector (purchased from Pharmacia Inc.) were double digested by SfiI and NotI, digested fragments were recovered from gel, ligated at 16° C. overnight, then transformed into competent *E. coli* HB2151, on the next day, 20 single colonies were picked from the transformation plates and cultured at 30° C. to OD600 of 0.4~0.6 when IPTG was added to a final concentration of 0.05 mmol/L to induce expression, then expressed overnight (18 h). Supernatant was obtained by centrifugation, and soluble scFv expressed therein was assessed by ELISA analysis. Specifically, a 96-well plate was coated by antigen WTE-BSA (manufactured by Shanghai Raygene biotechnology Co., Ltd.) at 50 ng/well (1 ng/μl, 50 μl/well), incubated at 37° C. for 2 h, blocked with 5% PBS skimmed milk powder (Bright Dairy Co., Ltd.) at 37° C. for 2 h, washed three times with 0.1 M phosphate buffer (PBS), then the supernatant from culture with induced expression was loaded to the 96-well plate by 50 μl/well, and incubated at 37° C. for 1 h. After washed three times with PBST (PBS+0.05% Tween20), HRP labeled anti-E tag antibody (purchased from Shanghai Raygene biotechnology Co., Ltd., 1:1000 dilution) was added 50 μl/well, and incubated at 37° C. for 1 h. After washed three times with PBST, goat anti-mouse IgG-HRP (purchased from Santa Cruz Biotechnology, 1:1000 dilution), was added and incubated at 37° C. for 1 h. After washed five times with PBST, Washed with PBST 5 times, ABTS visualizing reagent was added 100 μl/well, incubated for 10 min in dark for visualization. Optical absorbance was detected by Bio-Rad Model 680 platereader at a wavelength of 405 nm, values at least 2 times the optical absorbance of negative control were deemed positive. Clone 2D3-3, which is associated with the greatest OD value, was sequenced, then plasmid pCANTAB 5E 2D3-3 scfv was isolated for single chain antibody 2D3 used in the sham control CAR adopted in this application, and separately assembled with fragment CD28a-CD28b-CD137-CD3ζ prepared as described above in subsection "(2) Nucleic acid sequences for other parts of the chimeric receptor antigen" and equimolar of eGFP nucleic acid fragment having F2A and CD8α signal peptide at 3' end prepared as described above in subsection "(3) Nucleic acid sequences for other parts of the chimeric receptor antigen" (approx. 50 ng), the three fragments were assembled following the pattern shown in FIG. 2 and PCR amplified, assembling conditions were: initial denaturation at 94° C. for 4 min; denaturation at 94° C. for 40 s, annealing at 60° C. for 40 s, extension at 68° C. for 140 s, for 5 cycles; followed by elongation at 68° C. for 10 min; following addition of DNA polymerase as well as upstream primer 5'-cttacgcgtcctagcgctaccggtcgccaccatggtgagcaagggcgaggag-3' (SEQ ID NO:16) and downstream primer 5'-gaggtcgacctagcgagggggcagggcctgcatg-3' (SEQ ID NO:13) were 25 cycles of PCR amplification, amplification conditions were: initial denaturation at 94° C. for 4 min; denaturation at 94° C. for 40 s, annealing at 60° C. for 40 s, and extension at 68° C. for 140 s, for 25 cycles; followed by final elongation at 68° C. for 10 min. The theoretical size of the amplified eGFP-2D3-28BBZ is 2443 bp. Amplified product was confirmed of being consistent with the theoretical size by agarose gel electrophoresis.

3. Construction of Lentiviral Vectors

The exemplified vector system utilized in the lentiviral plasmid vector constructed in the present invention belongs to the third generation self-inactivating lentiviral vector system, which consists of three plasmids, a packaging plasmid psPAX2 encoding protein Gag/Pol, and encoding Rev protein; an envelope plasmid PMD2.G encoding VSV-G protein, and a recombinant expression vector which is based on empty vector pWPT-eGFP and encoding the target gene CAR.

In the empty vector pWPT-eGFP, the elongation factor-1α (EF-1α) promoter regulates expression of the enhanced green fluorescent protein (eGFP), while in the recombinant expression vector encoding target gene CAR, the co-expression of eGFP and target gene CAR was achieved through the ribosomal skipping sequence (F2A) from foot and mouth disease virus (FMDV). F2A is a fragment of core sequence of 2A (alternatively, "self-splicing polypeptide 2A") from foot and mouth disease virus, which pertains the "self-splicing" capability of 2A that allows the co-expression of both upstream and downstream genes. Associated with advantages including high splicing efficiency, highly balanced expression of upstream and downstream genes, as well as its own short sequences, 2A offers an effective and feasible approach of building polycistronic vectors for gene therapy. Particularly, immunotherapy based on T lymphocyte modified with chimeric antigen receptor gene primarily utilizes this sequence to achieve the co-expression of target gene and GFP or eGFP, thus, the expression of CAR can be detected indirectly by detecting the expression of GFP or eGFP.

Figure 3:
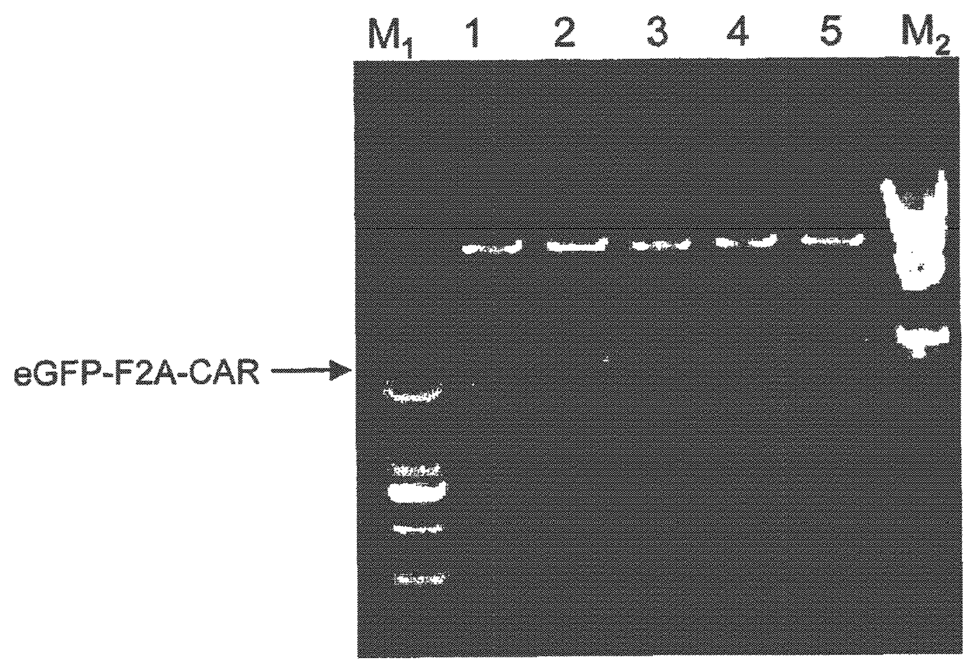
FIG. 3 shows an electrophoregram of nucleic acid for the identification of lentiviral plasmid of Example 1 upon MluI and SalI double digestion. Wherein M1 is DS2000 molecular weight marker (Dongsheng Biotech Co., Ltd., Guangzhou); M2 is Hind III marker (Dongsheng Biotech Co., Ltd., Guangzhou). Lanes 1-5 are, respectively, 1: pWPT-eGFP-F2A-GPC3-δ Z;
2: pWPT-eGFP-F2A-GPC3-Z;
3: pWPT-eGFP-F2A-GPC3-BBZ;
4: pWPT-eGFP-F2A-GPC3-28Z;
5: pWPT-eGFP-F2A-GPC3-28BBZ.

In this Example, lentiviral vectors collectively named as pWPT-eGFP-F2A-CAR are constructed having F2A associated with eGFP and specific CAR to be coexpressed. Target gene eGFP-F2A-CARs obtained in Step 2 described above were double digested by restriction endonucleases MluI and SalI, ligated into pWPT vector which has been digested by the same enzymes, such that lentiviral vectors expressing each chimeric antigen receptors were constructed. The constructed vectors were identified through digestion by MluI and SalI (FIG. 3) and sequenced for correctness; vectors validated thereby are ready for packaging lentivirus. As described above, eGFP-F2A-CAR was transcribed into one mRNA, while eventually translated into two polypeptides, eGFP and anti-GPC3 chimeric antigen receptor, wherein the anti-GPC3 chimeric antigen receptor would be localized to the cell membrane under the guidance of CD8α signal peptide. After inserted into lentiviral plasmid vector, the negative control eGFP-GPC3-δ Z expressed, at the surface of cell membrane, a GPC3 chimeric antigen receptor δ Zcontaining truncated δ Z (GPC3-δ Z) having the amino acid sequence of SEQ ID NO: 32.

Complete nucleic acid sequences of the vectors containing each target CAR are as following: pWPT-eGFP-F2A-GPC3-δ Z (SEQ ID NO: 26); pWPT-eGFP-F2A-GPC3-Z (SEQ ID NO: 27); pWPT-eGFP-F2A-GPC3-BBZ (SEQ ID NO: 28); pWPT-eGFP-F2A-GPC3-28Z (SEQ ID NO: 29); pWPT-eGFP-F2A-GPC3-28BBZ (SEQ ID NO: 30).

4. Plasmid Transfection and Lentivirus Packaging in 293T Cells

For transfection, 293T cells (ATCC: CRL-11268) cultured to passage 6 to 10 were seeded at a density of $6\times10^6$ in a 10 cm dish, incubated overnight at 37° C., 5% $CO_2$. The medium is DMEM (PAA Laboratories) containing 10% fetal bovine serum (PAA Laboratories). On the next day, the medium was exchanged for serum-free DMEM 2 hours prior to the transfection.

Transfection was carried out by the following steps:

4.1 Dissolving 20 μg of empty plasmid pWPT-eGFP (mock control) or 20 μg of each target gene plasmid pWPT-eGFP-F2A-CAR was separately dissolved into 500 μl MillQ water along with 15 μg of packaging plasmid PAX2 and 6 μg of envelope plasmid pMD2.G;

4.2 Dropwise adding 62 μl 2.5M $CaCl_2$ (Sigma), mixed by votexing at 1200 rpm/min;

4.3 Then dropwise adding 500 μl 2× Hepes (280 mM NaCl, 10 mM KCl, 1.5 mM Na2HPO4.2H2O, 12 mM glucose, 50 mM Hepes (Sigma), pH7.05, 0.22 μM filter sterilized), mixed by votexing at 1200 rpm/min for 10 s;

4.4 The mixture was immediately added dropwise into the culture dish and gently shaken to uniform, incubated at 37° C., 5% $CO_2$ for 4~6 h, then replaced with DMEM containing 10% fetal bovine serum.

Transfection efficiency (i.e., the proportion of cells presenting green fluorescent) was observed the next day, transfection with a positive transfection rate of ~80% is deemed a successful one. At 48 h or 72 h after transfection, virus was collected by filtration with 0.45 μm filter (Millipore), followed by centrifugation at 28000 rpm under 4° C. for 2 hours using Beckman Optima L-100XP ultracentrifuge, the supernatant was discarded and the resulting pellet was resuspended into Quantum 007 medium (PAA company) to 1/10 ~1/50 of the starting liquid volume, divided into 100 μL/tube aliquots and frozen at −80° C. before virus titration or transducing T lymphocytes.

5. Titration of Lentivirus Carrying Mock or eGFP-F2A-CAR

On the first day, 293T cells were seeded at $1\times10^5$/mL, 100 μl/well into a 96-well culture plate, incubated at 37° C., 5% $CO_2$, where the medium is DMEM containing 10% fetal bovine serum. On the second day, 50 μl/well of culture supernatant was withdrawn, and supplemented with 50 μl/well of fresh culture medium as described above while containing a final concentration of 6 μg/mL of polybrene, incubated at 37° C., 5% $CO_2$ for 30 min. Then 10 μl/well of virus stock solution or 1 μl/well of concentrated virus solution was added, conducted with a 4-step 1:5 dilutions in duplicates, incubated at 37° C., 5% $CO_2$. At 48 hours after infection, eGFP was detected by flow cytometry, a positive rate of 5~20% of the cell number is suitable, calculated to give the titer (U/mL)=positive rate×dilution rate×100×$10^4$. From calcium phosphate transfection, the packaged lentiviruses containing mock (i.e., empty vector) control and each eGFP-F2A-CAR all reached a viral titer of about 0.5~$2\times10^6$ U/mL, and the viral titer detected from the concentrated virus was about $2\times10^7$ U/mL.

Example 2. CTL Cells Infected with Recombinant Lentivirus

Human peripheral blood mononuclear cells were obtained from healthy human peripheral blood by density gradient centrifugation (provided by Shanghai Blood Center), from such peripheral blood mononuclear cells CTLs were obtained by a negative selection process using CTL magnetic beads sorting (Stem Cell Technologies). After sorting, CTL cells were assayed by flow cytometry for purity of the CTL cells, a positive rate of 95% is deemed suitable for the next operation. CTL cells were added into Quantum 007 lymphocyte culture medium (PAA Laboratories) to a density of $1\times10^6$/mL, and dynabeads (Invitrogen) coated with both anti-CD3 and anti-CD28 antibodies were added to a cell: bead ratio of 1:1, and recombinant human IL-2 (Shanghai Huaxin High Biotechnology Inc.) was added to a final concentration of 100 U/mL for a stimulatory culture of 24 h. Then the CTL cells were infected by the recombinant lentivirus prepared above at an MOI of approx. 5. The infected cells were passaged every other day at a density of $5\times10^5$/mL, the lymphocyte culture medium was supplemented with a final concentration of 100 U/mL of recombinant human IL-2 as well.

Figure 4:
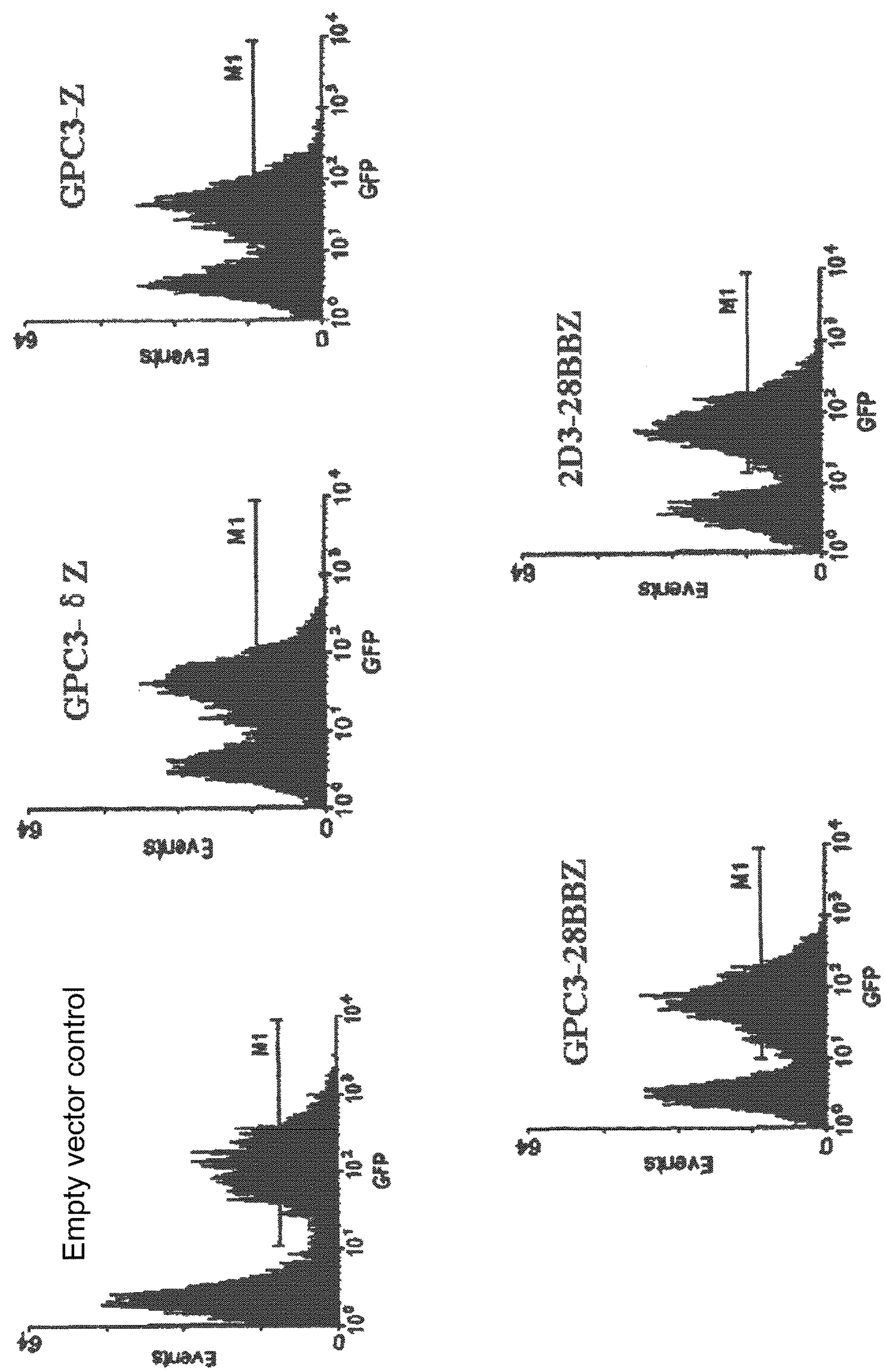
FIG. 4 shows results of flow cytometry assays for eGFP expression by CTL (cytotoxic T lymphocyte) cells infected by virus as described in Example 2.

At day 8 of culture, transduced CTL cells were assayed by flow cytometry for the expression of various chimeric antigen receptors. By virtue of the co-expression of eGFP and CAR, cells detected of being eGFP positive are positive cells expressing the chimeric antigen receptor (FIG. 4). Using untransduced T lymphocytes as the negative control, the positive rate of virus infected CTL cells expressing various chimeric antigen receptors are shown in the following table. This result on positive rates indicates that CARP CTL cells of certain positive rate could be obtained by the process of lentivurs infection.

TABLE 2

| CAR transfecting the CTL cells | eGFP positive rate of CTL cells |
|---|---|
| Mock (empty vector control) | 50% |
| GPC3-DZ | 59% |
| GPC3-Z | 58% |
| GPC3-28BBZ | 60% |
| 2D3-28BBZ | 62% |

Figure 5:
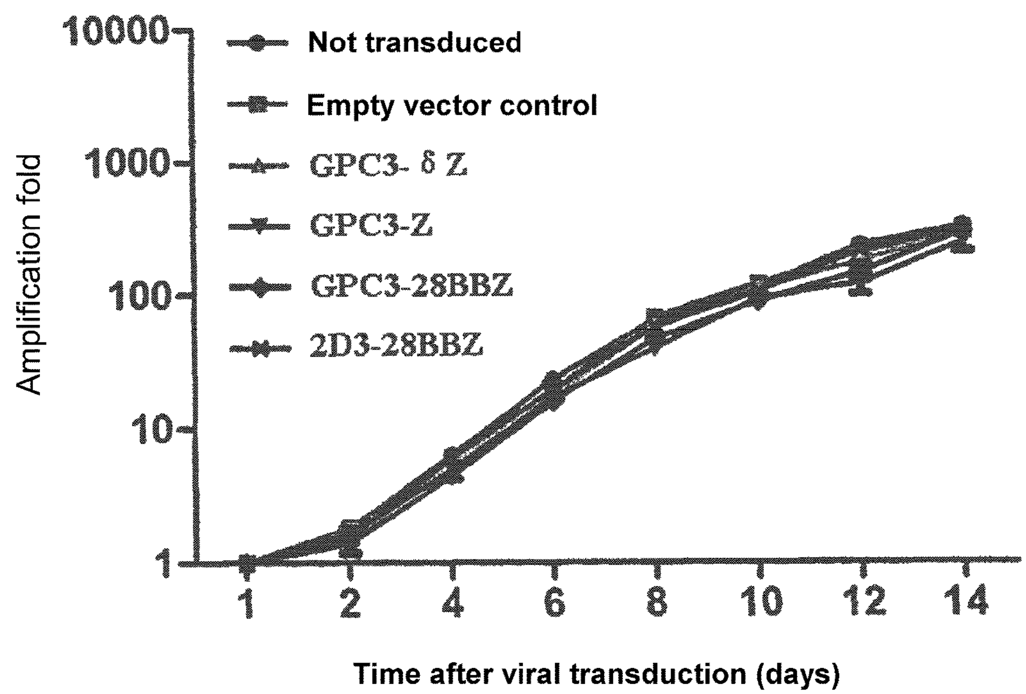
FIG. 5 shows the in vitro growth profiles of embodiment of the invention expression in vitro growth profile of CTL cells expressing different chimeric antigen receptors ($CAR^+$) as described in Example 2. The graph shows that, at day 14 after viral infection, CTL cells expressing different chimeric antigen receptors reached an in vitro proliferation of 200 times.

After respectively infected by viruses packaged with different chimeric antigen receptors, CTL cells were passaged at a cell density of $5\times10^5$/ml every other day, counted, and the medium for passaged culture was supplemented with IL-2 (a final concentration of 100 U/ml), the culture reached a proliferation of about 200 times at day 14 of culture (see FIG. 5), demonstrating that the CTL cells expressing various chimeric antigen receptor can undergo a certain amount of in vitro proliferation, which ensures the feasibility of subsequent in vitro cytotoxicity tests and in vivo assays.

Example 3. In Vitro Cytotoxicity Assay for Cells Expressing Chimeric Antigen Receptor Target cells used in in vitro cytotoxicity tests were hepatocellular carcinoma cell lines as shown in Table 3, effector cells were the CTL cells annotated as chimeric antigen receptor positive ($CAR^+$), which are the positive cells expressing chimeric antigen receptor in FACS detection as validated in Example 2 and in vitro cultured for 12 days.

TABLE 3

| Tumor Type | Identity | Source |
|---|---|---|
| Hepatocellular carcinoma | PLC/PRF/5 | ATCC: CRL-8024 |
| Hepatocellular cancer | Hep 3B2.1-7 | ATCC: HB-8064 |
| Hepatic adenocarcinoma | SK-HEP-1 | ATCC: HTB-52 |
| Hepatocellular cancer | Hep G2 | ATCC: HB-8065 |
| Hepatic adenocarcinoma | Huh-7 | RIKEN: RCB1366 |

Figure 6A:
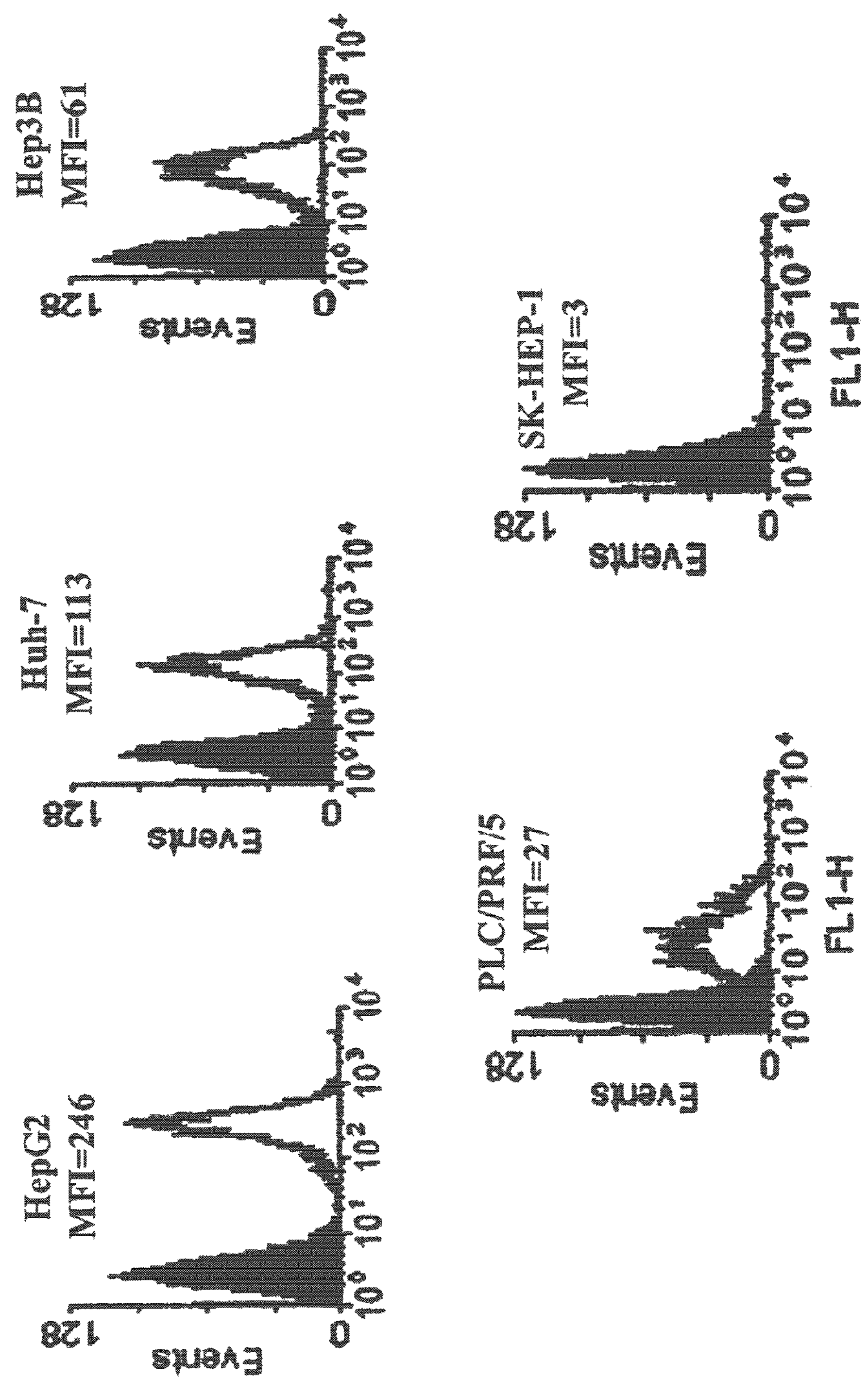
FIG. 6A shows the level of GPC3 expressed by various hepatocellular carcinoma cell lines detected by flow cytometry, GPC3 expression by the cells is represented by Mean Fluorescence Intensity (MFI)
Figure 6B:
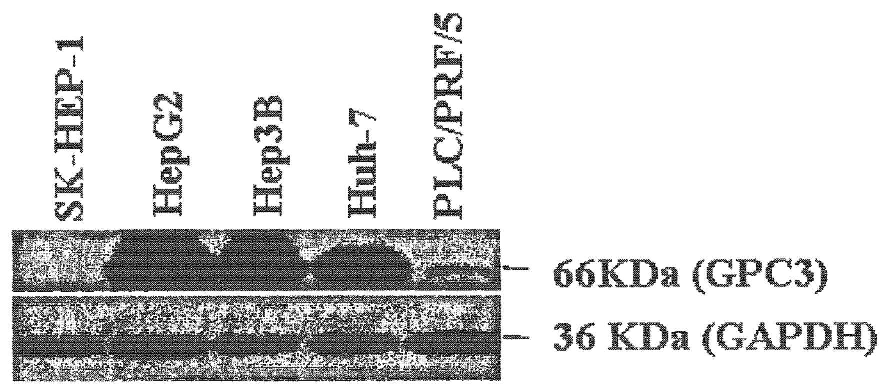
FIG. 6B shows the western blot results for the level of GPC3 expressed by these cell lines, wherein GAPDH is used as a loading internal control.

Hepatocellular carcinoma cell lines HepG2, Huh-7, Hep3B, PLC/PRF/5 and SK-HEP-1 were detected by flow cytometry and western blot for GPC3 expression levels, flow cytometry results are shown in FIG. 6A, GPC3 expression in cell was presented by Mean Fluorescence Intensity (MFI). Meanwhile, the GPC3 expression levels of each cell lines were further validated by western blot approach, the results are shown in FIG. 6B, wherein GAPDH was used as a loading control. The results suggests that various levels of GPC3 expression were observed in four hepatocellular carcinoma cell lines HepG2, Huh-7, Hep3B and PLC/PRF/5, while no GPC3 expression was detected in SK-HEP-1.

Each experimental group and each control group are comprised of the following materials:

Each experimental group: each target cells+CTLs expressing various chimeric antigen receptors, Control group 1: the maximum LDH release from the target cells, Control group 2: the spontaneous LDH release form target cells, Control group 3: the spontaneous LDH release from effector cells.

Detection process: CytoTox 96 non-radioactive cytotoxicity assay kit (Promega) was used to carry out the detection. The process is based on colorimetric detection, which is an alternative for $^{51}Cr$ release assay. CytoTox 96® assay quantitatively measure lactate dehydrogenase (LDH). LDH is a stable cytoplasmic enzyme, which is released upon cell lysis in a way that is basically the same as $^{51}Cr$ release in the radioactive assay. LDH released into the culture supernatant can be detected by a 30 minutes coupled enzymatic reaction, wherein LDH converts a tetrazolium salt (INT) into a red formazan. An amount of the red product produced thereby is proportional to the number of lysed cells. Instructions for CytoTox 96 non-radioactive cytotoxicity assay kit could be referred to for particulars.

Based on the circumstance, effector:target ratios were 3:1, 1:1, and 1:3, respectively, the number of target cells was 10,000/well (50 μL $2\times10^5$/mL), and the number of effector cells was determined by the corresponding effector:target ratio. Each group was setup with five wells in replicate, an average of the 5 replicate wells was calculated. The detection was conducted at 18 h.

Cytotoxicity is calculated using the following equation:

$$\text{Cytotoxicity \%} = \frac{\text{Experimental Group} - \text{Control 2} - \text{Control 3}}{\text{Control 1} - \text{Control 2}} \times 100\%$$

Results of the experiments indicate the following:

As shown in Table 4, in this invention, CTL expression chimeric antigen receptor GPC3-Z CAR$^+$ and CTL expression chimeric antigen receptor GPC3-28BBZ CAR$^+$ both exhibited very significantly specific cytotoxicity against GPC3 positive hepatocellular carcinoma cell lines HepG2, Huh-7, Hep3B and PLC/PRF/5 cells, and presented an effector:target ratio dependency, namely a higher effector: target ratio would give a stronger cytotoxicity effect, meanwhile, these CTLs exhibited no specific cytotoxicity against GPC3 negative hepatocellular carcinoma cell line SK-HEP-1. At an effector:target ratio of 3:1, GPC3-28BBZ resulted in a cytotoxicity of up to 97% against GPC3 positive hepatoma cell HepG2 cells, and a cytotoxicity of up to 84% against GPC3 positive hepatoma cell PLC/PRF/5.

Data on effector:target ratio dependency further indicate the specific cytotoxicity effect of the CTLs expressing chimeric antigen receptor targeting GPC3 according to this invention on GPC3 positive hepatoma cell lines.

In comparison, negative control CTLs infected by virus transfected with mock plasmid (empty plasmid vector pWPT-eGFP carrying no GPC3-CAR) or sham control CAR 2D3-28BBZ exhibited rather low cytotoxicity against all 5 cell lines described above, suggesting an insensitivity towards GPC3 expression. In addition, due to the lack of intracellular signaling domain, CTLs transfected with GPC3-δZ containing a truncated form of CD3ζ was similar to the CTLs transfected with mock and 2D3-28BBZ in terms of toxicity effect. In summary, according to the present invention, the CTL expressing chimeric antigen receptor targeting GPC3 (GPC3-Z and GPC3-28BBZ) exhibited specific toxicity effect on GPC3 positive hepatoma cells, and GPC3-28BBZ CAR T cells expressing the signaling domains of costimulatory molecules CD28 and CD137 exhibited a stronger toxicity effect than those GPC3-Z CAR T cells which do not possess these two signaling domains.

TABLE 4

| Cytotoxicity | GPC3-28BBZ Effector:target ratio | | | GPC3-Z Effector:target ratio | | | Mock Effector:target ratio | | |
|---|---|---|---|---|---|---|---|---|---|
| (%) | 3:1 | 1:1 | 1:3 | 3:1 | 1:1 | 1:3 | 3:1 | 1:1 | 1:3 |
| PLC/PRF/5 | 84 ± 3.5 | 41 ± 6.2 | 18 ± 3.9 | 65 ± 5 | 31 ± 6.5 | 11 ± 6.2 | 13 ± 7 | 5 ± 1.5 | 1.3 ± 3.2 |
| Hep3B | 81 ± 5.5 | 53 ± 4.9 | 25 ± 8.3 | 69 ± 7.7 | 39 ± 6.3 | 19 ± 1.9 | 2.3 ± 4.7 | 7.6 ± 3.5 | 8.8 ± 4.2 |
| SK-HEP-1 | 8.4 ± 4.5 | 5.4 ± 7.2 | 9 ± 4.3 | 3.3 ± 2.1 | 4.4 ± 3.4 | 2.5 ± 2.2 | 13 ± 10 | 12 ± 7.9 | 10 ± 5 |
| Hep G2 | 96 ± 5.1 | 60 ± 4.9 | 15 ± 4 | 61 ± 6.5 | 39 ± 4.7 | 16 ± 0.3 | 9 ± 2.2 | 3.5 ± 1.9 | 1.5 ± 0.5 |
| Huh-7 | 97 ± 6.3 | 71 ± 3.8 | 25 ± 4.6 | 75 ± 3.8 | 54 ± 6.4 | 26 ± 6.2 | 16 ± 2.5 | 15 ± 5.3 | 4.6 ± 1.6 |

TABLE 4-continued

| Cytotoxicity | 2D3-28BBZ Effector:target ratio | | | GPC3-DZ Effector:target ratio | | |
|---|---|---|---|---|---|---|
| (%) | 3:1 | 1:1 | 1:3 | 3:1 | 1:1 | 1:3 |
| PLC/PRF/5 | 16 ± 7.7 | 8.4 ± 4.7 | 3.6 ± 3.4 | 4.3 ± 1.7 | 11.6 ± 2.9 | 4.3 ± 1.3 |
| Hep3B | 13.6 ± 5.8 | 9.5 ± 5.9 | 4.8 ± 2.9 | 12 ± 3.9 | 8.9 ± 3.2 | 5.7 ± 4.9 |
| SK-HEP-1 | 12. ± 3.6 | 9.8 ± 6.6 | 2.1 ± 3.4 | 13 ± 3.9 | 9.8 ± 6.6 | 3.9 ± 2.8 |
| Hep G2 | 16 ± 8.9 | 7.7 ± 4.7 | 1.3 ± 2.5 | 5.4 ± 4.3 | 0.5 ± 2.9 | 0.05 ± 2.3 |
| Huh-7 | 18 ± 9.2 | 12.6 ± 4.5 | 4.8 ± 3.1 | 17 ± 2.2 | 13 ± 3.3 | 4.2 ± 1.3 |

Example 4. Preliminary Test of Treating Huh-7 Xenografted Tumor of High GPC3 Expression Using CAR T Cells Targeting GPC3

Animal grouping: Forty NOD/SCID mice, aged 6-8 weeks were randomly divided into six groups (n=6~7 per group), the experimental groups were, GPC3-Z CAR T lymphocyte group, GPC3-28BBZ CAR T lymphocyte group of different effector:target ratios (1:1 and 1:2); the control groups were, GPC3-δZ CAR T lymphocyte, mock CAR T lymphocyte control group, and saline control group.

Inoculation: At day 0, 200 mg/kg of cyclophosphamide was intraperitoneally injected; at day 1, Huh-7 cells ($2\times10^6$/mouse) were inoculated subcutaneously into the right flank with GPC3-Z, Mock, GPC3-28BBZ (1:1 and 1:2) CAR T lymphocytes and GPC3-δZ CAR T lymphocytes mixed with 1:1 effector cells, while the mice in saline control group were injected with Huh-7 cells ($2\times10^6$/mouse) only.

Figure 7A:
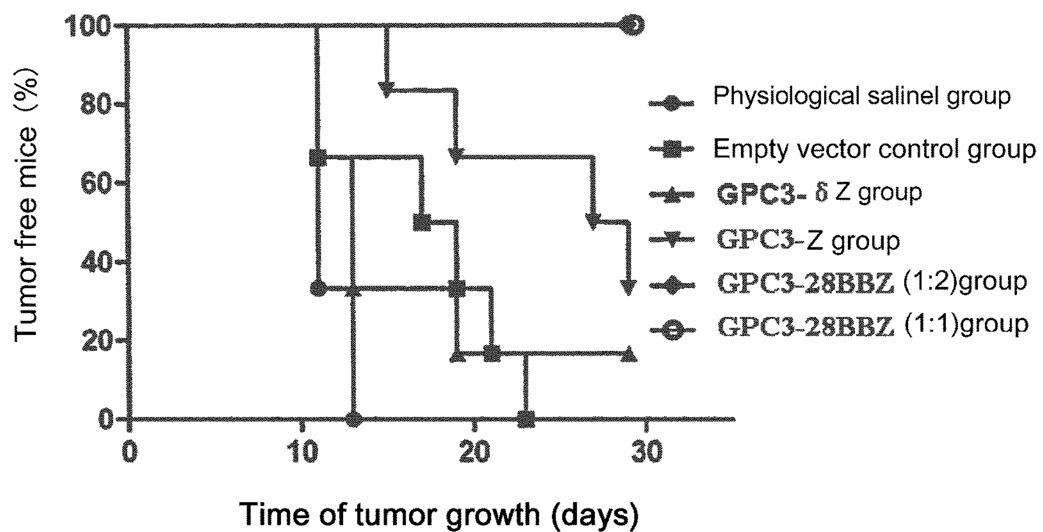
FIG. 7A is a graph showing the percentage of tumor-free mice within each group vs. time after treatment of Huh-7 xenografted tumor by CAR T cells targeting GPC3.
Figure 7B:
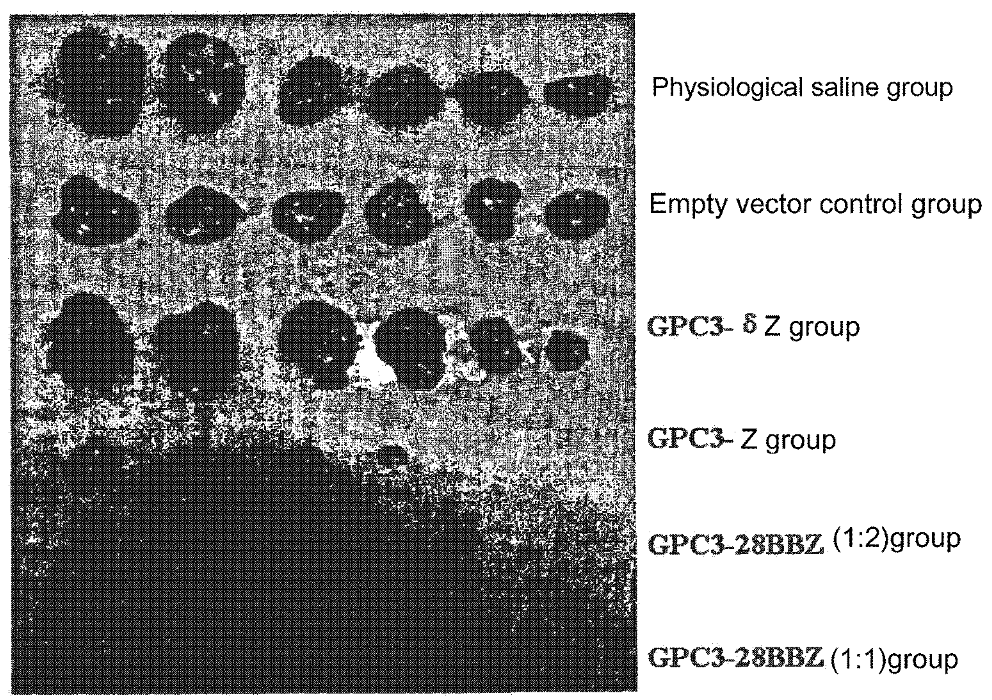
FIG. 7B shows the size of tumors in 6 mice sacrificed in each group.

Results of the experiment showed that the CAR T cells expressing GPC3-Z and GPC3-28BBZ can specifically inhibit GPC3-positive Huh-7 cells from tumor formation. The experiment was terminated when tumor in mice of control group reached 2000 $mm^3$ (day 28 after the xenograft inoculation). In GPC3-Z CAR T lymphocyte treatment group, 2/6 mice exhibited no tumor growth, and in GPC3-28BBZ CAR T lymphocyte treatment groups with effector: target ratio of both 1:1 and 1:2 groups, all six mice exhibited no tumor growth, while in control groups, such as Mock group and GPC3-δZ CAR T lymphocyte group and the saline group, no effect on tumor formation in mice was observed (FIG. 7A). FIG. 7B shows the sizes of tumors obtained after sacrifice from the bodies of all 6 mice in each group.

Example 5. Treatment Assay of GPC3-Targeted CAR T Cells Against Subcutaneous Huh-7 Tumor Xenografts with High GPC3 Expression Tumor inoculation: Well growing Huh-7 cells in logarithmic growth phase were collected and adjusted to a cell density of $1\times10^7$/ml using physiological saline, and injected in a volume of 200 μL ($2\times10^6$/mouse), the date of tumor inoculation was recorded as day 0.

Adoptive transfer of T cells: When the tumor volume in mice reached 200-300 $mm^3$, which is day 13 after the tumor inoculation, cyclophosphamide (200 mg/kg) was intraperitoneally injected, and at day 14, the experimental groups and the control groups were administrated $8\times10^6$/mouse of genetically modified T lymphocyte (positive transfection rate of approx. 50%) and physiological saline only, respectively, by tail vein injection.

Animal grouping: Thirty NOD/SCID mice, aged 6-8 weeks were randomly divided into four groups of 6 each the experimental group was GPC3-28BBZ CAR T lymphocyte treatment group, and the control groups were, 2D3-28BBZ CAR T lymphocyte control group, mock genetically modified CAR T lymphocyte control group, and saline control group.

Two weeks after the adoptive transfer of T cells (Day 28), tumor volume in control mice reached 2000 $mm^3$, the experiment was terminated. In GPC3-28BBZ CAR T lymphocyte treatment group, tumor regression was observed in 3/6 mice, in comparison with all three control groups, volume (FIG. 8A) and weight (FIG. 8B) of residual tumor in mice both show results of significant differences (*$P<0.001$). FIG. 8D shows the tumor tissue profile of sacrificed mice in each group. FIG. 8**E shows the tumor regression profile in mice after GPC3-28BBZ CAR T lymphocyte treatment (in comparison with Mock group). The results demonstrate that GPC3-28BBZ CAR T lymphocytes can significantly inhibit the growth of Huh-7 tumor xenografts.

Figure 8A:
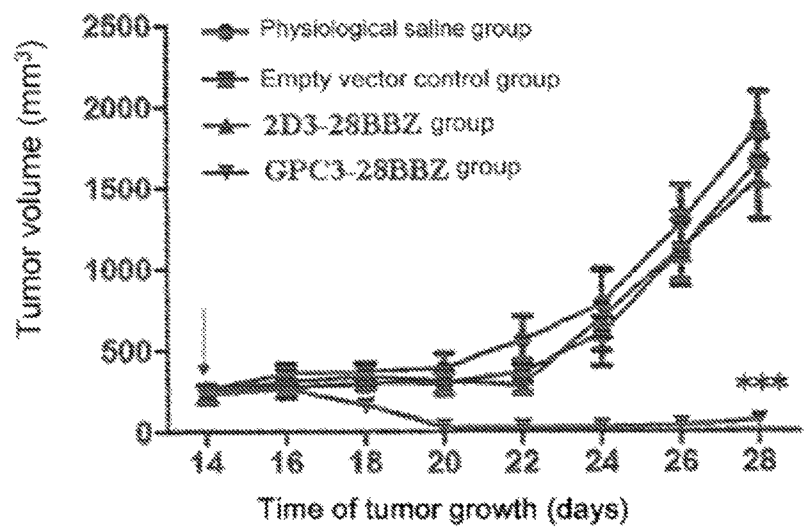
FIG. 8A shows the result comparing the volume of residual tumor in mice between the groups as described in Example 5.
Figure 8B:
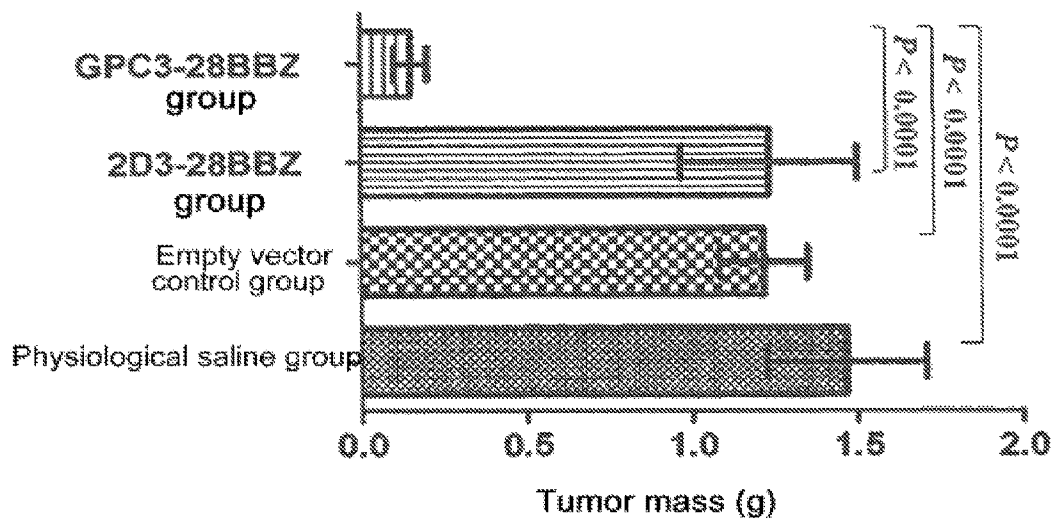
FIG. 8B shows the result comparing the weight of residual tumor in mice between the groups as described in Example 5.
Figure 8C:
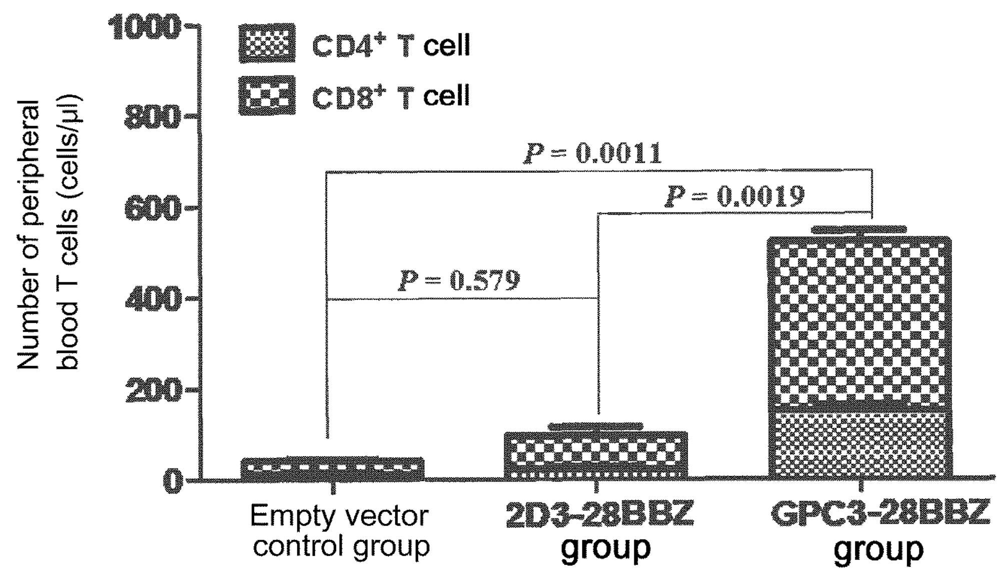
FIG. 8C shows the number of viable T cells in peripheral blood of mice in each group as described in Example 5 detected one week after adoptive infusion of T lymphocytes.
Figure 8D:
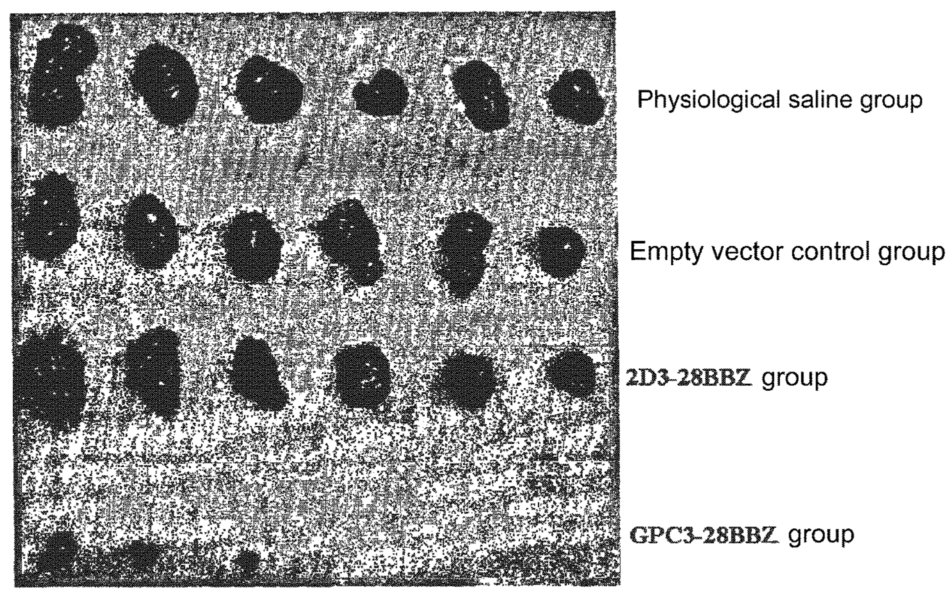
FIG. 8D shows the tumor profiles of mice in each group as described in Example 5 observed upon sacrifice.
Figure 8E:
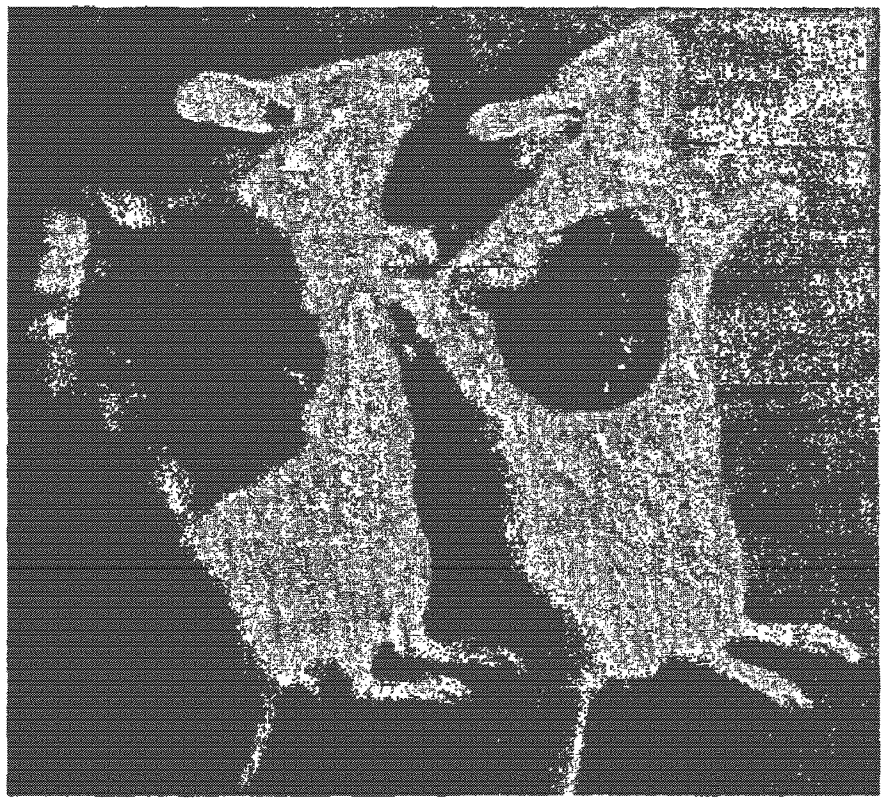
FIG. 8E shows the tumor regression observed in mice treated by GPC3-28BBZ CAR T lymphocyte as described in Example 5 (in comparison with mock).

In addition, number of survived peripheral blood T cells was detected one week after adoptive infusion of T lymphocytes, results are shown in FIG. 8C, T cell numbers in GPC3-28BBZ CAR T cells treated mice was significantly higher than the mock control group and 2D3-28BBZ CAR T lymphocyte treatment group (GPC3-28BBZ vs mock, P=0.0011; GPC3-28BBZ vs 2D3-28BBZ, P=0.0019; 2D3-28BBZ vs mock, P=0.359). The results shown in FIG. 9C demonstrate that GPC3-28BBZ CAR T lymphocytes can survive well in vivo.

Figure 9:
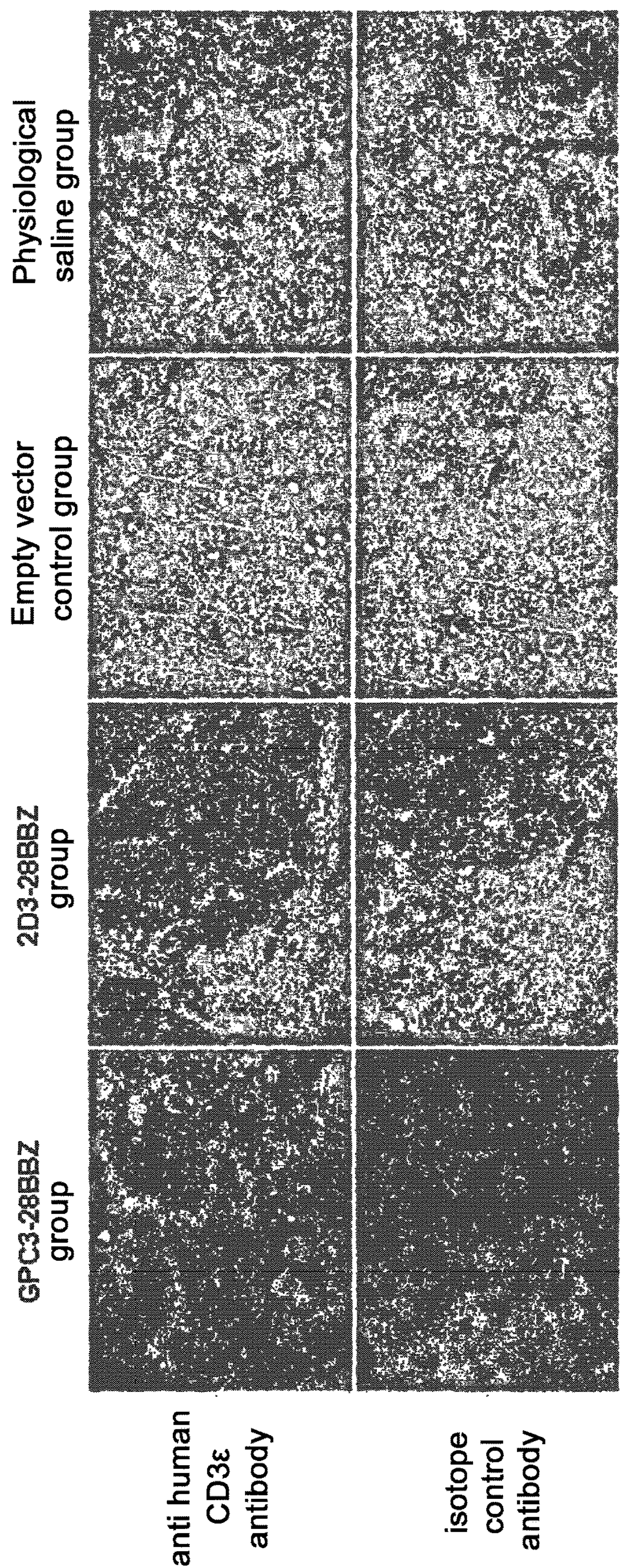
FIG. 9 shows the immunohistochemical staining results indicating the T cell accumulation in grafted tumor tissue in mice of each group after adoptive infusion as described in Example 5.

At the end of the experiment, grafted Huh-7 tumor tissues from each group were sectioned and immunostained using anti-human CD3e antibody, results of the immunohistochemical staining are shown in FIG. 9. The results show that, human CD3 positive T cells observed in site of subcutaneous grafted tumor of mice in GPC3-28BBZ CAR T cell treatment group were substantially more than those in 2D3-28BBZ transfected and mock T cell treatment group, while no human T cells were detected in saline group, suggesting that GPC3-28BBZ CAR T cells can accumulate at the tumor site in order to exercise its function of killing tumor cells.

These results indicate that GPC3-28BBZ CAR T cells can partially remove subcutaneously grafted Huh-7 tumor of high GPC3 expression.

Example 6. Test of Treating PLC/RPF/5 Subcutaneously Xenografted Tumor of Low GPC3 Expression Using GPC3-28BBZ CAR T Cells Tumor inoculation: well growing PLC/RPF/5 cells in logarithmic growth phase were collected and adjusted to a cell density of $2.5\times10^7$/ml using physiologicalsaline, and injected in a volume of 200 μL ($5\times10^6$/mouse), and the date of tumor inoculation was recorded as day 0.

Adoptive transfer of T cells: when the tumor volume in mice reached 150 $mm^3$, which is day 21, cyclophosphamide (200 mg/kg) was intraperitoneally injected, and at day 22 and 30, the experimental groups and the control groups were administrated $8\times10^6$/mouse of genetically modified T lymphocyte (positive transfection rate of approx. 50%) and physiological saline only, respectively, by tail vein injection.

Animal grouping: Thirty NOD/SCID mice, aged 6-8 weeks were randomly divided into five groups of 6 each, the experimental group was GPC3-28BBZ CAR T lymphocyte treatment group, and the control groups were, 2D3-28BBZ CAR T lymphocyte control group, mock genetically modified CAR T lymphocyte control group, and saline control group.

When average tumor volume in mice reached 150 $mm^3$ (day 21), mice were randomly divided into 4 groups according to the T cells to be adoptive transferred and administrated with 200 mg/kg of cyclophosphamide by intraperitoneal injection, and at day 22 and 30, respectively administrated with $8\times10^6$/mouse of T lymphocyte genetically modified with GPC3-28BBZ, 2D3-28BBZ or mock (positive transfection rates of approx. 50%, respectively) and physiological saline only, respectively, by tail vein injection. The experiment was terminated at day 46 when average tumor volume in control mice reached 1500 $mm^3$.

Figure 10A:
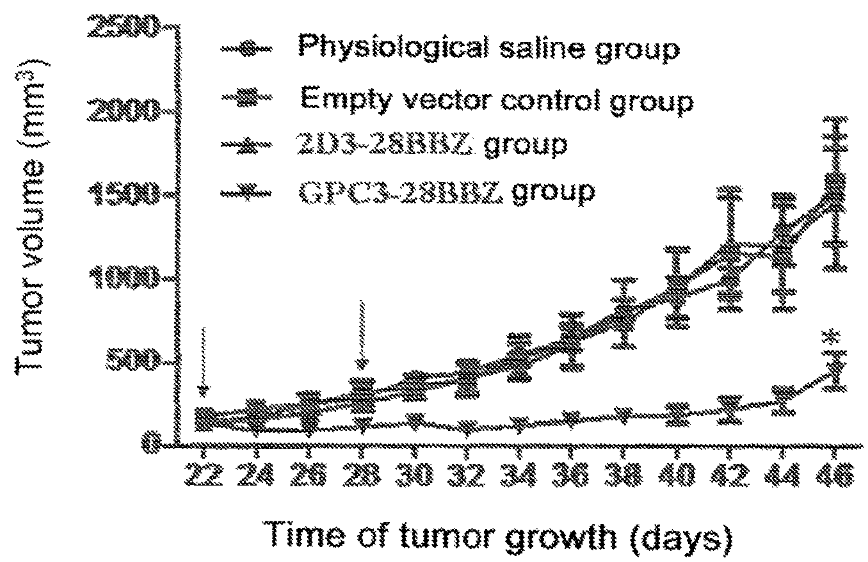
FIG. 10A shows the volume of grafted tumor in mice of the groups as described in Example 6.
Figure 10B:
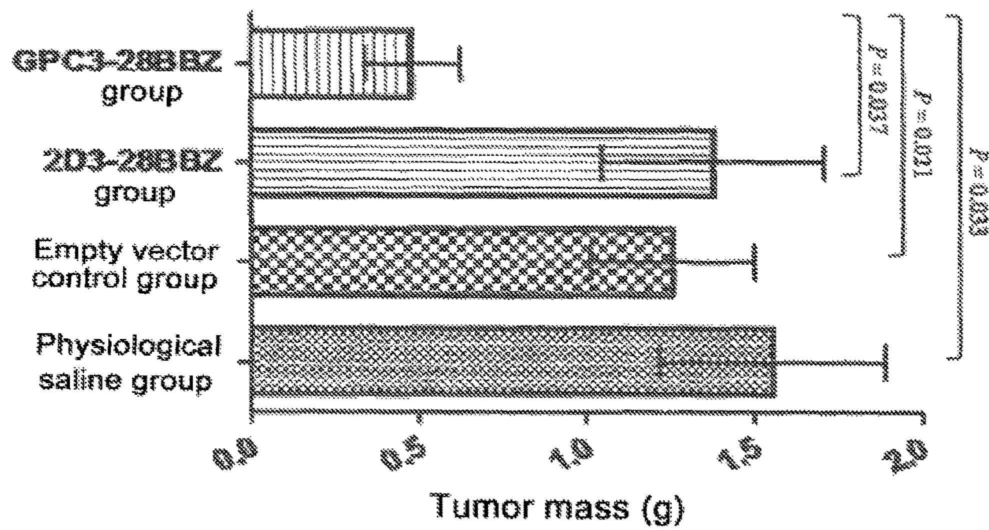
FIG. 10B shows the weight of tumor tissue obtained upon the completion of experiment from mice of each group as described in Example 6.
Figure 10C:
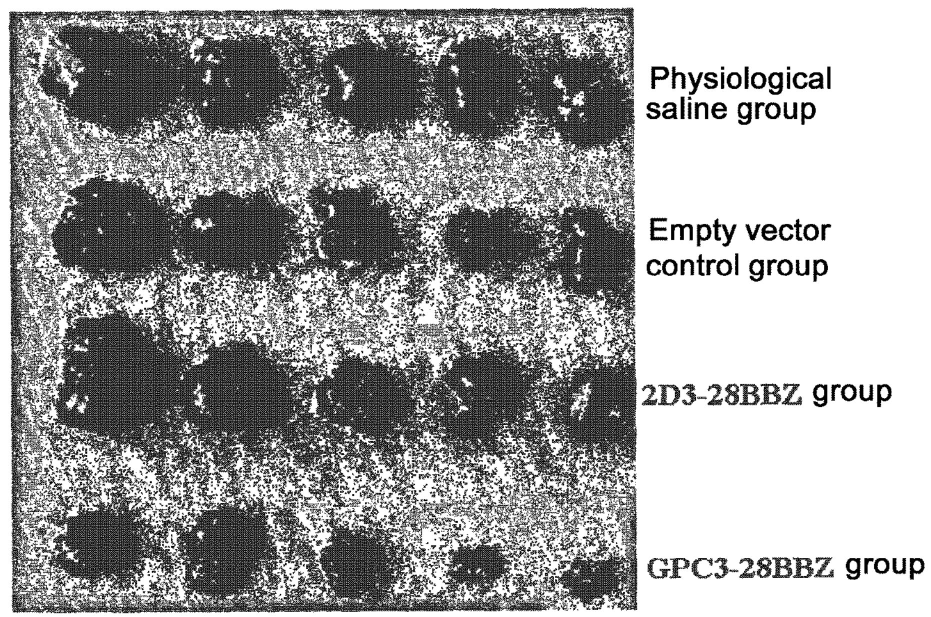
FIG. 10C shows the tumor tissue of mice in each group as described in Example 6.

FIG. 10A shows the growth curve of tumor. At day 46, the volume of grafted tumor in GPC3-28BBZ CAR T lymphocyte treatment group was significantly smaller than all control groups (*P<0.05). FIG. 10B shows weight result of tumor tissues obtained upon the closure of experiment, compared with tumors in control groups, tumor weights in GPC3-28BBZ CAR T lymphocyte treatment group were significantly lower than control groups (GPC3-28BBZ vs saline, P=0.0332; GPC3-28BBZ vs mock, P=0.0211; GPC3-28BBZ vs 2D3-28BBZ, P=0.0211). FIG. 10C shows the tumor tissue profile of sacrificed mice in each group when the experiment was terminated, indicating that GPC3-28BBZ CAR T lymphocytes treatment has a significantly inhibition effect on PLC/RPF/5 cells with low GPC3 expression.

Figure 10D:
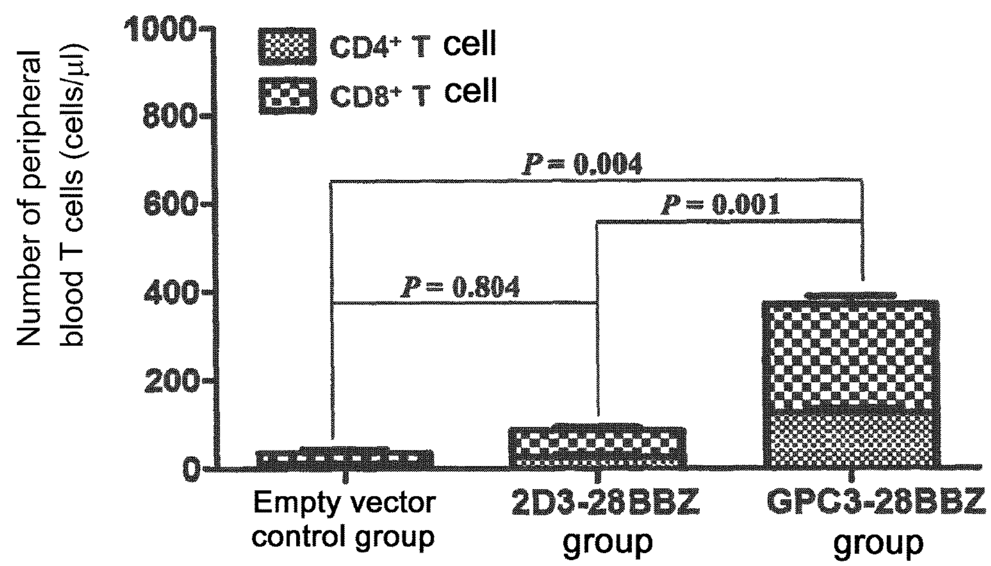
FIG. 10D shows the number of T cells in peripheral blood of mice in each group as described in Example 6 detected one week after the last adoptive infusion of T cells.

To detect T cell survival profile in mice, numbers of T cells in peripheral blood of mice were detected one week after the last adoptive transfer of T cells. The results shown in FIG. 10D indicate that the number of T cells observed in mice of GPC3-28BBZ CAR T lymphocytes treatment group was significantly higher than control (GPC3-28BBZ vs mock, P=0.004; GPC3-28BBZ vs 2D3-28BBZ, P=0.0097; 2D3-28BBZ vs mock, P=0.0804), suggesting that GPC3-28BBZ CAR T lymphocytes can survive well in vivo.

These results indicate that GPC3-28BBZ CAR T cells can significantly inhibit growth of grafted PLC/RPF/5 tumor with low GPC3 expression.

Example 7. Eradication Activities Assay of GPC3-28BBZ CAR T Cells Against Orthotopic GPC3-Positive Huh-7 Tumor Xenograft Tumor inoculation: Well growing Huh-7 cells (Luc+) in logarithmic growth phase were collected and adjusted to a cell density of $1\times10^8$/ml using normal saline, 25 μL cell suspension was mixed with 25 μL Metrigel (on ice), by open surgery conducted within a sterile clean bench, cells mixed to uniform were inoculated to the right lobe of liver ($2.5\times10^6$/mouse) for 40 NOD/SCID mice, aged 6-8 weeks, the date of tumor inoculation was recorded as day 0.

Animal grouping: After the date of tumor inoculation in mice, pictures were taken weekly, two weeks after, cyclophosphamide (200 mg/kg) was intraperitoneally injected and mice were randomly divided into 4 groups of 7 each, the experimental group was GPC3-28BBZ CAR T lymphocyte treatment group, and the control groups were, 2D3-28BBZ CAR T lymphocyte control group, mock genetically modified CAR T lymphocyte control group, and saline control group.

Adoptive transfer of T cells: At day 14 and 21 after tumor inoculation, $5\times10^6$/mouse of genetically modified T lymphocytes (positive transfection rates of approx. 50%, injection volume of 200 μL) or 200 μL of physiological saline only were injected by tail vein of the mice.

Figure 11A:
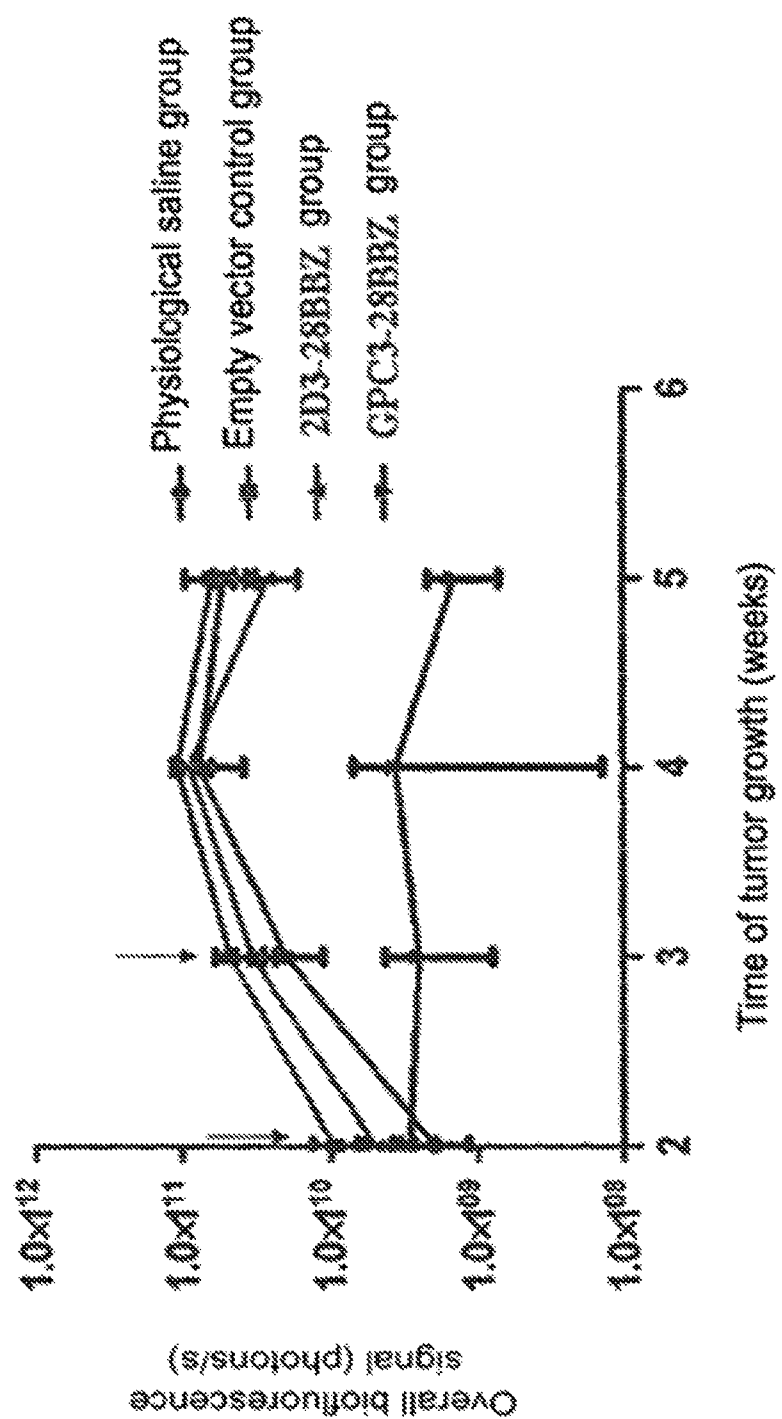
FIGS. 11A and 11B show the biofluorescence intensity of tumor and the actual tumor imaging picture of mice in each group as described in Example 7, respectively.
Figure 11B:
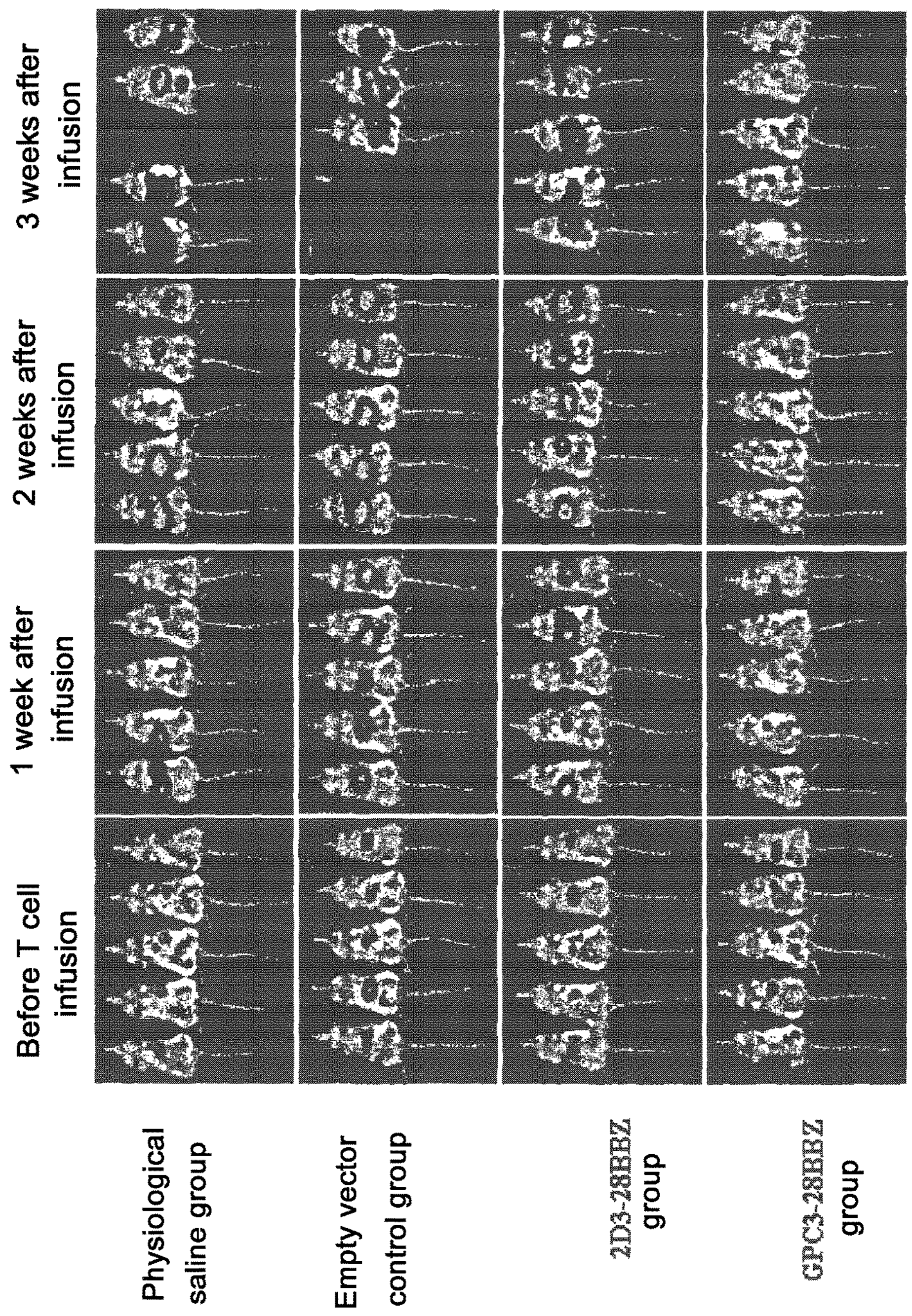
Figure 11C:
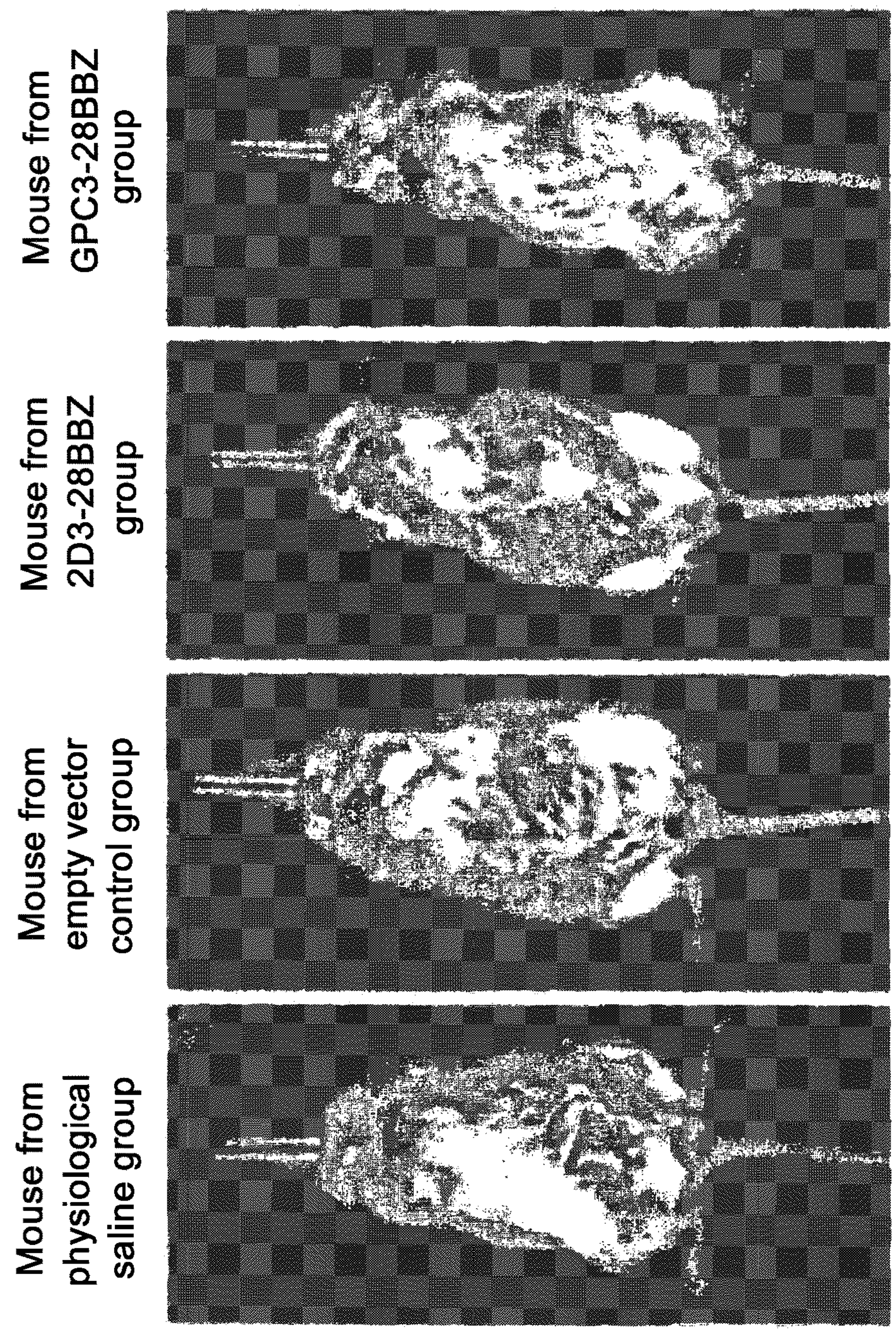
FIGS. 11C and 11D show abdominal tumor-bearing profiles (in vitro) and anatomically observed tumor profiles for mice in each group as described in Example 7, respectively.
Figures 11D, 11E:
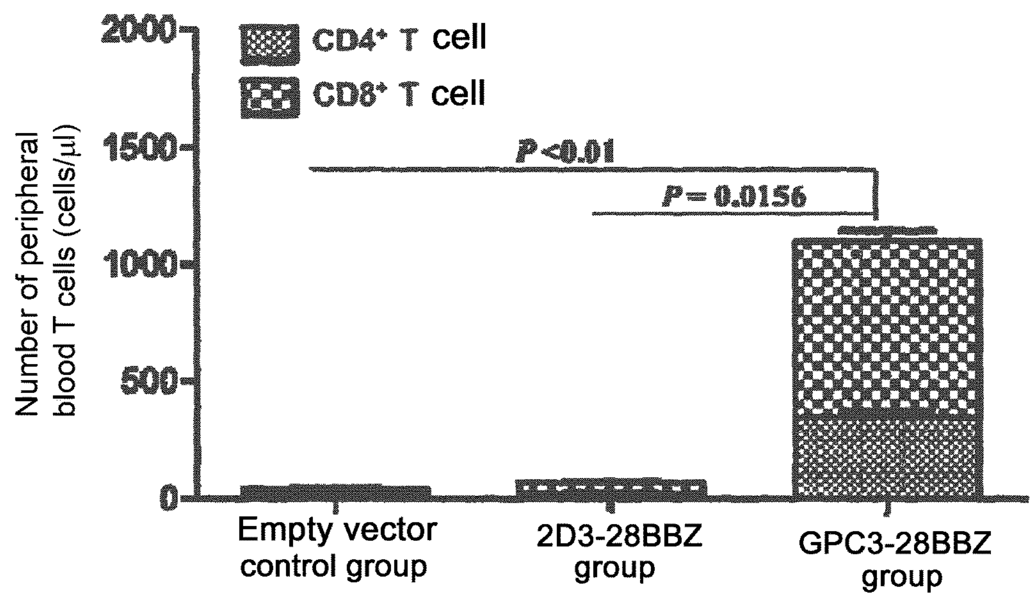
FIG. 11E shows the number of T cells in peripheral blood of mice in each group detected one week after the last adoptive transfusion of T cells.
Figure 11F:
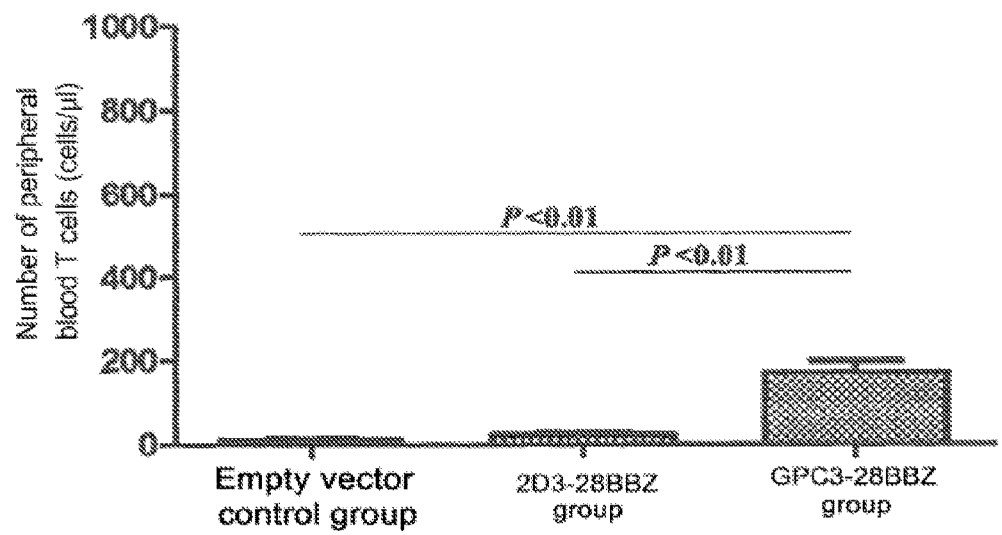
FIG. 11F shows the number of CAR positive T cells in peripheral blood of mice in each group detected one week after the last adoptive infusion of T cells.
Figure 11G:
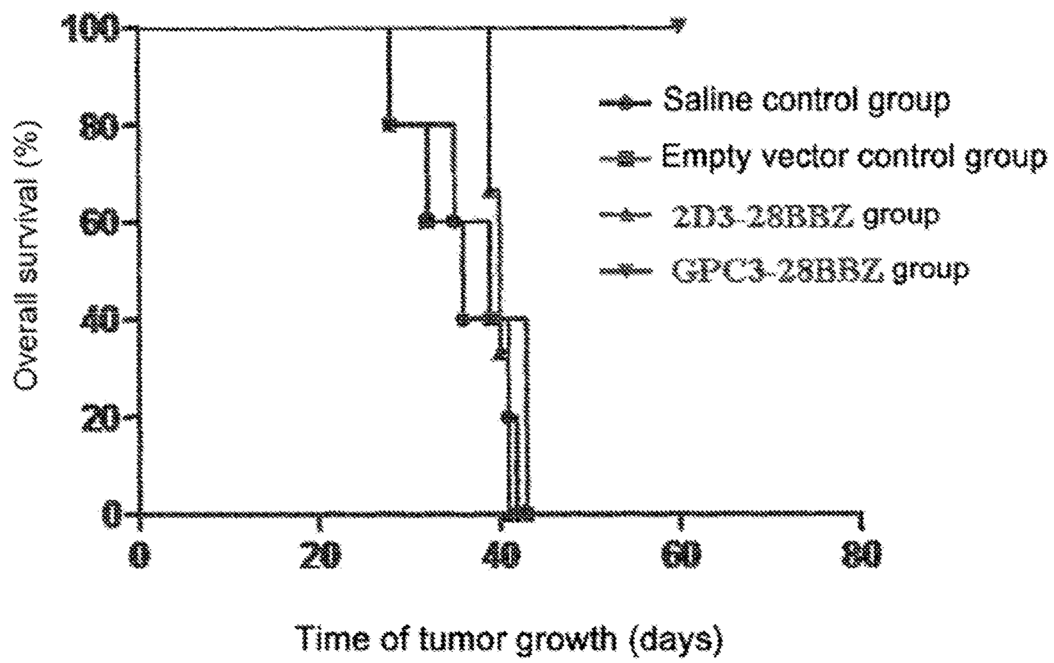
FIG. 11G shows the survival rate of mice in each group of Example 7 vs. the time after tumor inoculation.

At one week after the first injection of transgenic T lymphocytes for treatment, tumors observed in mice of GPC3-28BBZ CAR T lymphocyte treatment group were significantly smaller than those in control groups, and pictures taken subsequently 2 weeks and 3 weeks after both observed significantly smaller tumors in mice of GPC3-28BBZ CAR T lymphocyte treatment group than those in control groups (FIG. 11A and FIG. 11B), at one week after the last injection of transgenic T lymphocytes, mice in all 3 control groups, i.e., 2D3-28BBZ CAR T lymphocyte treatment control group, mock T cell treatment group, and saline control group, were observed with significantly swollen abdomen, while the mice in the GPC3-28BBZ CAR T lymphocyte treatment group had normal abdomen (FIG. 11C). Mice anatomy revealed that there was an enormous tumor mass at the liver of mice in control groups, while no tumor growth was observed at the liver of mice in the GPC3-28BBZ CAR T lymphocyte treatment group (FIG. 11D). Survival profile of injected T cells in mouse body was detected by withdrawing orbit blood at one week after the last injection of T lymphocytes, the results show that the number of lymphocyte observed in mice from GPC3-28BBZ CAR T lymphocytes treatment group is significantly more than that of mock and 2D3-28BBZ control groups (GPC3-28BBZ vs mock, P=0.0012; GPC3-28BBZ vs 2D3-28BBZ, P=0.0156; 2D3-28BBZ vs mock, P=0.355; FIG. 11E). With respect to CAR positive T-cells, the highest number in peripheral blood was also observed in GPC3-28BBZ CAR T cell treatment group (GPC3-28BBZ vs mock, P=0.0012; GPC3-28BBZ vs 2D3-28BBZ, P=0.0015; 2D3-28BBZ vs mock, P=0.22; FIG. 11F). After the experiment has continued for 4 weeks, animals in control groups died in succession. The median survival times in the control groups were 34 days in mock control group, 39 days in 2D3-28BBZ control group, and 33 days in saline group respectively (FIG. 11G), while at that point of time, mice in GPC3-28BBZ CAR T cell treatment group were still observed surviving well, with no swollen abdomen.

In summary, GPC3-28BBZ CAR T cells exhibits substantial efficacy for treating Huh-7 orthotopic xenografts, and GPC3-28BBZ CAR T cell can effectively survive in mice bearing Huh-7 orthotopic xenograft.

Seeking for protection in this application, T cells genetically modified with chimeric antigen receptor gene targeting GPC3 can specifically recognize and kill GPC3-positive hepatoma cells, while imposing no effect on GPC3 negative hepatoma cells, they have potential clinical value.

TABLE 5

| Sequence in this invention | |
|---|---|
| Sequence | Description |
| SEQ ID NOs: 1~17 | Primer sequences |
| SEQ ID NO: 18 | Nucleic acid sequence encoding chimeric antigen receptor GPC3-Z |
| SEQ ID NO: 19 | Nucleic acid sequence encoding chimeric antigen receptor GPC3-BBZ |
| SEQ ID NO: 20 | Nucleic acid sequence encoding chimeric antigen receptor GPC3-28Z |

TABLE 5-continued

| Sequence in this invention | |
|---|---|
| Sequence | Description |
| SEQ ID NO: 21 | Nucleic acid sequence encoding chimeric antigen receptor GPC3-28BBZ |
| SEQ ID NO: 22 | Amino acid sequence of chimeric antigen receptor GPC3-Z |
| SEQ ID NO: 23 | Amino acid sequence of chimeric antigen receptor GPC3-BBZ |
| SEQ ID NO: 24 | Amino acid sequence of chimeric antigen receptor GPC3-28Z |
| SEQ ID NO: 25 | Amino acid sequence of chimeric antigen receptor GPC3-28BBZ |
| SEQ ID NO: 26 | Complete sequence of vector pWPT-eGFP-F2A-GPC3-δZ |
| SEQ ID NO: 27 | Complete sequence of vector pWPT-eGFP-F2A-GPC3-Z |
| SEQ ID NO: 28 | Complete sequence of vector pWPT-eGFP-F2A-GPC3-BBZ |
| SEQ ID NO: 29 | Complete sequence of vector pWPT-eGFP-F2A-GPC3-28Z |

The invention claimed is:

1. A nucleic acid encoding a chimeric antigen receptor targeting glypican-3 (GPC3) for expressing at a surface of a human T lymphocyte, wherein the chimeric antigen receptor targeting GPC3 comprises, connected in an order of, an extracellular binding domain, a transmembrane region, and an intracellular signaling domain, wherein the extracellular binding domain comprises a single chain antibody scFv (GPC3) which specifically recognizes a C-terminal epitope of GPC3, and wherein the chimeric antigen receptor comprises SEQ ID NO: 25.

2. The nucleic acid according to claim 1 comprising SEQ ID NO: 21.

3. A vector comprising a nucleic acid encoding a chimeric antigen receptor targeting glypican-3 (GPC3) for expressing at a surface of a human T lymphocyte, wherein the chimeric antigen receptor targeting GPC3 comprises, connected in an order of, an extracellular binding domain, a transmembrane region, and an intracellular signaling domain, wherein the extracellular binding domain comprises a single chain antibody scFv(GPC3) which specifically recognizes a C-terminal epitope of GPC3, and wherein the chimeric antigen receptor comprises SEQ ID NO: 25.

4. The vector according to claim 3, wherein the vector comprises SEQ ID NO: 30.

5. A virus comprising a vector including nucleic acid encoding a chimeric antigen receptor targeting glypican-3 (GPC3) for expressing at a surface of a human T lymphocyte, wherein the chimeric antigen receptor targeting GPC3 comprises, connected in an order of, an extracellular binding domain, a transmembrane region, and an intracellular signaling domain, wherein the extracellular binding domain comprises a single chain antibody scFv(GPC3) which specifically recognizes a C-terminal epitope of GPC3, and wherein the chimeric antigen receptor comprises SEQ ID NO: 25.

6. A genetically modified T lymphocyte transfected with a nucleic acid encoding a chimeric antigen receptor targeting glypican-3 (GPC3) for expressing at a surface of a human T lymphocyte, wherein the chimeric antigen receptor targeting GPC3 comprises, connected in an order of, an extracellular binding domain, a transmembrane region, and an intracellular signaling domain, wherein the extracellular binding domain comprises a single chain antibody scFv(GPC3) which specifically recognizes a C-terminal epitope of GPC3, and wherein the chimeric antigen receptor comprises SEQ ID NO: 25.

7. A genetically modified T lymphocyte comprising a chimeric antigen receptor expressed at a surface thereof, wherein the chimeric antigen receptor is encoded by a nucleic acid comprising SEQ ID NO: 21.

8. A genetically modified T lymphocyte comprising a chimeric antigen receptor expressed at a surface thereof, wherein the chimeric antigen receptor comprises SEQ ID NO: 25.

9. A genetically modified T lymphocyte transfected with a vector comprising a nucleic acid encoding a chimeric antigen receptor targeting glypican-3 (GPC3) for expressing at a surface of a human T lymphocyte, wherein the chimeric antigen receptor targeting GPC3 comprises, connected in an order of, an extracellular binding domain, a transmembrane region, and an intracellular signaling domain, wherein the extracellular binding domain comprises a single chain antibody scFv(GPC3) which specifically recognizes a C-terminal epitope of GPC3, and wherein the chimeric antigen receptor comprises SEQ ID NO: 25.

10. A genetically modified T lymphocyte transfected with a virus comprising a vector comprising nucleic acid encoding a chimeric antigen receptor targeting glypican-3 (GPC3) for expressing at a surface of a human T lymphocyte, wherein the chimeric antigen receptor targeting GPC3 comprises, connected in an order of, an extracellular binding domain, a transmembrane region, and an intracellular signaling domain, wherein the extracellular binding domain comprises a single chain antibody scFv(GPC3) which specifically recognizes a C-terminal epitope of GPC3, wherein the chimeric antigen receptor comprises SEQ ID NO: 25.

11. A method of treating a hepatocellular carcinoma comprising administering to a human in need thereof an effective amount of genetically modified lymphocytes comprising a chimeric antigen receptor (CAR) that targets glypican-3 (GPC3), wherein the CAR comprises an extracellular binding domain, transmembrane region, and intracellular signaling domain, wherein the CAR binds a C-terminal epitope of GPC3, wherein the chimeric antigen receptor comprises SEQ ID NO: 25, and wherein the amount of the genetically modified lymphocytes is effective in reducing tumor volume after the administration.

12. The method of claim 11, further comprising administering cyclophosphamide to the human.

13. The method of claim 11, wherein the genetically modified lymphocytes are infused into the human.

14. The method of claim 11, wherein the genetically modified lymphocytes comprise a cytotoxic T cell (CTL).

15. The method of claim 11, wherein the CAR is encoded by SEQ ID NO: 21.

16. The method of claim 11, wherein the C-terminal epitope of GPC3 comprises amino acids 524-563 of GPC3.

17. The method of claim 11, wherein the amount of the genetically modified lymphocytes is effective in reducing tumor volume by at least 50%.

18. The method of claim 11, wherein the human comprises viable CD4+ or CD8+ T cells in peripheral blood after the administration.

19. The method of claim 11, wherein the amount of the genetically modified lymphocytes is effective in increasing survival time of the human after the administration.

* * * * *

SEQUENCE LISTING

```
<160> NUMBER OF SEQ ID NOS: 32

<210> SEQ ID NO 1
<211> LENGTH: 22
<212> TYPE: DNA
<213> ORGANISM: Artificial sequence
<220> FEATURE:
<223> OTHER INFORMATION: Primer

<400> SEQUENCE: 1

gatgttgtga tgactcagtc tc                                              22


<210> SEQ ID NO 2
<211> LENGTH: 34
<212> TYPE: DNA
<213> ORGANISM: Artificial sequence
<220> FEATURE:
<223> OTHER INFORMATION: Primer

<400> SEQUENCE: 2

gcgctggcgt cgtggttgag gagacggtga ccag                                 34


<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3

accacgacgc cagcgccgcg accac                                           25


<210> SEQ ID NO 4
<211> LENGTH: 39
<212> TYPE: DNA
<213> ORGANISM: Artificial sequence
<220> FEATURE:
<223> OTHER INFORMATION: Primer

<400> SEQUENCE: 4

gaggtcgacc tagcgagggg gcagggcctg catgtgaag                            39


<210> SEQ ID NO 5
<211> LENGTH: 62
<212> TYPE: DNA
<213> ORGANISM: Artificial sequence
<220> FEATURE:
<223> OTHER INFORMATION: Primer

<400> SEQUENCE: 5
```

-continued

```
gaggtcgacc tacgcggggg cgtctgcgct cctgctgaac ttcactctgg tgataaccag     60

tg                                                                    62


<210> SEQ ID NO 6
<211> LENGTH: 52
<212> TYPE: DNA
<213> ORGANISM: Artificial sequence
<220> FEATURE:
<223> OTHER INFORMATION: Primer

<400> SEQUENCE: 6

cttacgcgtc ctagcgctac cggtcgccac catggtgagc aagggcgagg ag             52


<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7

cggcctggcg gcgtggagca g                                               21


<210> SEQ ID NO 8
<211> LENGTH: 23
<212> TYPE: DNA
<213> ORGANISM: Artificial sequence
<220> FEATURE:
<223> OTHER INFORMATION: Primer

<400> SEQUENCE: 8

ttttgggtgc tggtggtggt tgg                                             23


<210> SEQ ID NO 9
<211> LENGTH: 34
<212> TYPE: DNA
<213> ORGANISM: Artificial sequence
<220> FEATURE:
<223> OTHER INFORMATION: Primer

<400> SEQUENCE: 9

gctgaacttc actctggagc gataggctgc gaag                                 34


<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10

aaacggggca gaaagaaact c                                               21


<210> SEQ ID NO 11
<211> LENGTH: 18
<212> TYPE: DNA
<213> ORGANISM: Artificial sequence
<220> FEATURE:
<223> OTHER INFORMATION: Primer

<400> SEQUENCE: 11

cagttcacat cctccttc                                                   18


<210> SEQ ID NO 12
<211> LENGTH: 35
```

<212> TYPE: DNA
<213> ORGANISM: Artificial sequence
<220> FEATURE:
<223> OTHER INFORMATION: Primer

<400> SEQUENCE: 12
cactggttat caccagagtg aagttcagca ggagc 35

<210> SEQ ID NO 13
<211> LENGTH: 34
<212> TYPE: DNA
<213> ORGANISM: Artificial sequence
<220> FEATURE:
<223> OTHER INFORMATION: Primer

<400> SEQUENCE: 13
gaggtcgacc tagcgagggg gcagggcctg catg 34

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
accacgacgc cagcgccg 18

<210> SEQ ID NO 15
<211> LENGTH: 19
<212> TYPE: DNA
<213> ORGANISM: Artificial sequence
<220> FEATURE:
<223> OTHER INFORMATION: Primer

<400> SEQUENCE: 15
cacccagaaa ataataaag 19

<210> SEQ ID NO 16
<211> LENGTH: 52
<212> TYPE: DNA
<213> ORGANISM: Artificial sequence
<220> FEATURE:
<223> OTHER INFORMATION: Primer

<400> SEQUENCE: 16
cttacgcgtc ctagcgctac cggtcgccac catggtgagc aagggcgagg ag 52

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
cggcctggcg gcgtggagca g 21

<210> SEQ ID NO 18
<211> LENGTH: 1266
<212> TYPE: DNA
<213> ORGANISM: Artificial sequence
<220> FEATURE:
<223> OTHER INFORMATION: GPC3 CAR (GPC3-Z)

<400> SEQUENCE: 18

```
gatgttgtga tgactcagtc tccactctcc ctgcccgtca cccctggaga gccggcctcc      60

atctcctgca gatctagtca gagccttgta cacagtaatg ccaacaccta tttacattgg     120

tacctgcaga agccagggca gtctccacag ctcctgatct ataaagtttc caaccgattt     180

tctggggtcc ctgacaggtt cagtggcagt ggatcaggca cagattttac actgaaaatc     240

agcagagtgg aggctgagga tgttggggtt tattactgct ctcaaaatac acatgttcct     300

cctacgtttg gccaggggac caagctggag atcaaacgtg gtggaggcgg ttcaggcgga     360

ggtggctctg gcggtggcgg atcgcaggtg cagctggtgc agtctggagc tgaggtgaag     420

aagcctgggg cctcagtgaa ggtctcctgc aaggcttctg gatacacctt caccgactat     480

gaaatgcact gggtgcgaca ggcccctgga caagggcttg agtggatggg agctcttgat     540

cctaaaactg gtgatactgc ctacagtcag aagttcaagg gcagagtcac gctgaccgcg     600

gacgaatcca cgagcacagc ctacatggag ctgagcagcc tgagatctga ggacacggcc     660

gtgtattact gtacaagatt ctactcctat acttactggg gccagggaac cctggtcacc     720

gtctcctcaa ccacgacgcc agcgccgcga ccaccaacac cggcgcccac catcgcgtcg     780

cagcccctgt ccctgcgccc agaggcgtgc cggccagcgg cggggggcgc agtgcacacg     840

agggggctgg acttcgcctg tgatatctac atctgggcgc ccttggccgg gacttgtggg     900

gtccttctcc tgtcactggt tatcaccaga gtgaagttca gcaggagcgc agacgccccc     960

gcgtaccagc agggccagaa ccagctctat aacgagctca atctaggacg aagagaggag    1020

tacgatgttt tggacaagag acgtggccgg gaccctgaga tggggggaaa gccgcagaga    1080

aggaagaacc ctcaggaagg cctgtacaat gaactgcaga aagataagat ggcggaggcc    1140

tacagtgaga ttgggatgaa aggcgagcgc cggaggggca aggggcacga tggcctttac    1200

cagggtctca gtacagccac caaggacacc tacgacgccc ttcacatgca ggccctgccc    1260

cctcgc                                                               1266
```

```
<210> SEQ ID NO 19
<211> LENGTH: 1392
<212> TYPE: DNA
<213> ORGANISM: Artificial sequence
<220> FEATURE:
<223> OTHER INFORMATION: GPC3-BBZ

<400> SEQUENCE: 19

gatgttgtga tgactcagtc tccactctcc ctgcccgtca cccctggaga gccggcctcc      60

atctcctgca gatctagtca gagccttgta cacagtaatg ccaacaccta tttacattgg     120

tacctgcaga agccagggca gtctccacag ctcctgatct ataaagtttc caaccgattt     180

tctggggtcc ctgacaggtt cagtggcagt ggatcaggca cagattttac actgaaaatc     240

agcagagtgg aggctgagga tgttggggtt tattactgct ctcaaaatac acatgttcct     300

cctacgtttg gccaggggac caagctggag atcaaacgtg gtggaggcgg ttcaggcgga     360

ggtggctctg gcggtggcgg atcgcaggtg cagctggtgc agtctggagc tgaggtgaag     420

aagcctgggg cctcagtgaa ggtctcctgc aaggcttctg gatacacctt caccgactat     480

gaaatgcact gggtgcgaca ggcccctgga caagggcttg agtggatggg agctcttgat     540

cctaaaactg gtgatactgc ctacagtcag aagttcaagg gcagagtcac gctgaccgcg     600

gacgaatcca cgagcacagc ctacatggag ctgagcagcc tgagatctga ggacacggcc     660

gtgtattact gtacaagatt ctactcctat acttactggg gccagggaac cctggtcacc     720

gtctcctcaa ccacgacgcc agcgccgcga ccaccaacac cggcgcccac catcgcgtcg     780
```

```
cagcccctgt ccctgcgccc agaggcgtgc cggccagcgg cggggggcgc agtgcacacg    840
agggggctgg acttcgcctg tgatatctac atctgggcgc ccttggccgg gacttgtggg    900
gtccttctcc tgtcactggt tatcaccaaa cggggcagaa agaaactcct gtatatattc    960
aaacaaccat ttatgagacc agtacaaact actcaagagg aagatggctg tagctgccga   1020
tttccagaag aagaagaagg aggatgtgaa ctgagagtga agttcagcag gagcgcagac   1080
gcccccgcgt accagcaggg ccagaaccag ctctataacg agctcaatct aggacgaaga   1140
gaggagtacg atgttttgga caagagacgt ggccgggacc ctgagatggg gggaaagccg   1200
cagagaagga agaaccctca ggaaggcctg tacaatgaac tgcagaaaga taagatggcg   1260
gaggcctaca gtgagattgg gatgaaaggc gagcgccgga ggggcaaggg gcacgatggc   1320
ctttaccagg gtctcagtac agccaccaag gacacctacg acgcccttca catgcaggcc   1380
ctgccccctc gc                                                       1392
```

```
<210> SEQ ID NO 20
<211> LENGTH: 1410
<212> TYPE: DNA
<213> ORGANISM: Artificial sequence
<220> FEATURE:
<223> OTHER INFORMATION: GPC3-28Z

<400> SEQUENCE: 20
```

```
gatgttgtga tgactcagtc tccactctcc ctgcccgtca cccctggaga gccggcctcc     60
atctcctgca gatctagtca gagccttgta cacagtaatg ccaacaccta tttacattgg    120
tacctgcaga agccagggca gtctccacag ctcctgatct ataaagtttc caaccgattt    180
tctggggtcc ctgacaggtt cagtggcagt ggatcaggca cagattttac actgaaaatc    240
agcagagtgg aggctgagga tgttggggtt tattactgct ctcaaaatac acatgttcct    300
cctacgtttg gccaggggac caagctggag atcaaacgtg gtggaggcgg ttcaggcgga    360
ggtggctctg gcggtggcgg atcgcaggtg cagctggtgc agtctggagc tgaggtgaag    420
aagcctgggg cctcagtgaa ggtctcctgc aaggcttctg gatacacctt caccgactat    480
gaaatgcact gggtgcgaca ggcccctgga caagggcttg agtggatggg agctcttgat    540
cctaaaactg gtgatactgc ctacagtcag aagttcaagg gcagagtcac gctgaccgcg    600
gacgaatcca cgagcacagc ctacatggag ctgagcagcc tgagatctga ggacacggcc    660
gtgtattact gtacaagatt ctactcctat acttactggg gccagggaac cctggtcacc    720
gtctcctcaa ccacgacgcc agcgccgcga ccaccaacac cggcgcccac catcgcgtcg    780
cagcccctgt ccctgcgccc agaggcgtgc cggccagcgg cggggggcgc agtgcacacg    840
agggggctgg acttcgcctg tgatttttgg gtgctggtgg tggttggtgg agtcctggct    900
tgctatagct tgctagtaac agtggccttt attattttct gggtgaggag taagaggagc    960
aggctcctgc acagtgacta catgaacatg actccccgcc gccccgggcc aacccgcaag   1020
cattaccagc cctatgcccc accacgcgac ttcgcagcct atcgctccag agtgaagttc   1080
agcaggagcg cagacgcccc cgcgtaccag cagggccaga accagctcta taacgagctc   1140
aatctaggac gaagagagga gtacgatgtt ttggacaaga gacgtggccg ggaccctgag   1200
atggggggaa agccgcagag aaggaagaac cctcaggaag gcctgtacaa tgaactgcag   1260
aaagataaga tggcggaggc ctacagtgag attgggatga aaggcgagcg ccggaggggc   1320
aaggggcacg atggccttta ccagggtctc agtacagcca ccaaggacac ctacgacgcc   1380
```

```
cttcacatgc aggccctgcc ccctcgctag                                    1410


<210> SEQ ID NO 21
<211> LENGTH: 1533
<212> TYPE: DNA
<213> ORGANISM: Artificial sequence
<220> FEATURE:
<223> OTHER INFORMATION: GPC3-CAR (GPC3-28BBZ)

<400> SEQUENCE: 21

gatgttgtga tgactcagtc tccactctcc ctgcccgtca cccctggaga gccggcctcc      60

atctcctgca gatctagtca gagccttgta cacagtaatg ccaacaccta tttacattgg     120

tacctgcaga agccagggca gtctccacag ctcctgatct ataaagtttc caaccgattt     180

tctggggtcc ctgacaggtt cagtggcagt ggatcaggca cagattttac actgaaaatc     240

agcagagtgg aggctgagga tgttggggtt tattactgct ctcaaaatac acatgttcct     300

cctacgtttg gccaggggac caagctggag atcaaacgtg gtggaggcgg ttcaggcgga     360

ggtggctctg gcggtggcgg atcgcaggtg cagctggtgc agtctggagc tgaggtgaag     420

aagcctgggg cctcagtgaa ggtctcctgc aaggcttctg gatacacctt caccgactat     480

gaaatgcact gggtgcgaca ggcccctgga caagggcttg agtggatggg agctcttgat     540

cctaaaactg gtgatactgc ctacagtcag aagttcaagg gcagagtcac gctgaccgcg     600

gacgaatcca cgagcacagc ctacatggag ctgagcagcc tgagatctga ggacacggcc     660

gtgtattact gtacaagatt ctactcctat acttactggg gccagggaac cctggtcacc     720

gtctcctcaa ccacgacgcc agcgccgcga ccaccaacac cggcgcccac catcgcgtcg     780

cagcccctgt ccctgcgccc agaggcgtgc cggccagcgg cggggggcgc agtgcacacg     840

agggggctgg acttcgcctg tgatttttgg gtgctggtgg tggttggtgg agtcctggct     900

tgctatagct tgctagtaac agtggccttt attattttct gggtgaggag taagaggagc     960

aggctcctgc acagtgacta catgaacatg actccccgcc gccccgggcc aacccgcaag    1020

cattaccagc cctatgcccc accacgcgac ttcgcagcct atcgctccaa acggggcaga    1080

aagaaactcc tgtatatatt caaacaacca tttatgagac cagtacaaac tactcaagag    1140

gaagatggct gtagctgccg atttccagaa gaagaagaag gaggatgtga actgagagtg    1200

aagttcagca ggagcgcaga cgcccccgcg taccagcagg gccagaacca gctctataac    1260

gagctcaatc taggacgaag agaggagtac gatgttttgg acaagagacg tggccgggac    1320

cctgagatgg ggggaaagcc gcagagaagg aagaaccctc aggaaggcct gtacaatgaa    1380

ctgcagaaag ataagatggc ggaggcctac agtgagattg ggatgaaagg cgagcgccgg    1440

aggggcaagg ggcacgatgg cctttaccag ggtctcagta cagccaccaa ggacacctac    1500

gacgcccttc acatgcaggc cctgccccct cgc                                 1533


<210> SEQ ID NO 22
<211> LENGTH: 422
<212> TYPE: PRT
<213> ORGANISM: Artificial sequence
<220> FEATURE:
<223> OTHER INFORMATION: GPC3-CAR(GPC3-Z)

<400> SEQUENCE: 22

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30
```

```
Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Arg Val Lys Phe Ser Arg Ser Ala Asp Ala Pro
305                 310                 315                 320

Ala Tyr Gln Gln Gly Gln Asn Gln Leu Tyr Asn Glu Leu Asn Leu Gly
                325                 330                 335

Arg Arg Glu Glu Tyr Asp Val Leu Asp Lys Arg Arg Gly Arg Asp Pro
            340                 345                 350

Glu Met Gly Gly Lys Pro Gln Arg Arg Lys Asn Pro Gln Glu Gly Leu
        355                 360                 365

Tyr Asn Glu Leu Gln Lys Asp Lys Met Ala Glu Ala Tyr Ser Glu Ile
    370                 375                 380

Gly Met Lys Gly Glu Arg Arg Arg Gly Lys Gly His Asp Gly Leu Tyr
385                 390                 395                 400

Gln Gly Leu Ser Thr Ala Thr Lys Asp Thr Tyr Asp Ala Leu His Met
                405                 410                 415

Gln Ala Leu Pro Pro Arg
            420
```

<210> SEQ ID NO 23
<211> LENGTH: 464

```
<212> TYPE: PRT
<213> ORGANISM: Artificial sequence
<220> FEATURE:
<223> OTHER INFORMATION: GPC3-BBZ amino acid

<400> SEQUENCE: 23

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Glu Gly Gly Cys Glu Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380
```

```
Val Leu Asp Lys Arg Arg Gly Arg Asp Pro Glu Met Gly Gly Lys Pro
385                 390                 395                 400

Gln Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460


<210> SEQ ID NO 24
<211> LENGTH: 469
<212> TYPE: PRT
<213> ORGANISM: Artificial sequence
<220> FEATURE:
<223> OTHER INFORMATION: GPC3-28Z

<400> SEQUENCE: 24

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285
```

```
Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465


<210> SEQ ID NO 25
<211> LENGTH: 511
<212> TYPE: PRT
<213> ORGANISM: Artificial sequence
<220> FEATURE:
<223> OTHER INFORMATION: GPC3-CAR (GPC3-Z8BBZ)

<400> SEQUENCE: 25

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175
```

```
Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510
```

<210> SEQ ID NO 26
<211> LENGTH: 10487
<212> TYPE: DNA
<213> ORGANISM: Artificial sequence
<220> FEATURE:
<223> OTHER INFORMATION: pWPT-eGFP-F2A-GPC3-delta Z

<400> SEQUENCE: 26

```
ttggaagggc taattcactc ccaaagaaga caagatatcc ttgatctgtg gatctaccac      60

acacaaggct acttccctga ttagcagaac tacacaccag ggccaggggt cagatatcca     120

ctgacctttg gatggtgcta caagctagta ccagttgagc cagataaggt agaagaggcc     180
```

```
aataaaggag agaacaccag cttgttacac cctgtgagcc tgcatgggat ggatgacccg    240
gagagagaag tgttagagtg gaggtttgac agccgcctag catttcatca cgtggcccga    300
gagctgcatc cggagtactt caagaactgc tgatatcgag cttgctacaa gggactttcc    360
gctggggact ttccagggag gcgtggcctg ggcgggactg gggagtggcg agccctcaga    420
tcctgcatat aagcagctgc tttttgcctg tactgggtct ctctggttag accagatctg    480
agcctgggag ctctctggct aactagggaa cccactgctt aagcctcaat aaagcttgcc    540
ttgagtgctt caagtagtgt gtgcccgtct gttgtgtgac tctggtaact agagatccct    600
cagacccttt tagtcagtgt ggaaaatctc tagcagtggc gcccgaacag ggacttgaaa    660
gcgaaaggga aaccagagga gctctctcga cgcaggactc ggcttgctga agcgcgcacg    720
gcaagaggcg aggggcggcg actggtgagt acgccaaaaa ttttgactag cggaggctag    780
aaggagagag atgggtgcga gagcgtcagt attaagcggg ggagaattag atcgcgatgg    840
gaaaaaattc ggttaaggcc agggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg gccgctgatc ttcagacctg gaggaggaga tatgagggac aattggagaa   1200
gtgaattata taaatataaa gtagtaaaaa ttgaaccatt aggagtagca cccaccaagg   1260
caaagagaag agtggtgcag agagaaaaaa gagcagtggg aataggagct ttgttccttg   1320
ggttcttggg agcagcagga agcactatgg gcgcagcgtc aatgacgctg acggtacagg   1380
ccagacaatt attgtctggt atagtgcagc agcagaacaa tttgctgagg gctattgagg   1440
cgcaacagca tctgttgcaa ctcacagtct ggggcatcaa gcagctccag gcaagaatcc   1500
tggctgtgga aagataccta aaggatcaac agctcctggg gatttggggt tgctctggaa   1560
aactcatttg caccactgct gtgccttgga atgctagttg gagtaataaa tctctggaac   1620
agatttggaa tcacacgacc tggatggagt gggacagaga aattaacaat tacacaagct   1680
taatacactc cttaattgaa gaatcgcaaa accagcaaga aaagaatgaa caagaattat   1740
tggaattaga taaatgggca agtttgtgga attggtttaa cataacaaat tggctgtggt   1800
atataaaatt attcataatg atagtaggag gcttggtagg tttaagaata gtttttgctg   1860
tactttctat agtgaataga gttaggcagg gatattcacc attatcgttt cagacccacc   1920
tcccaacccc gaggggaccc gacaggcccg aaggaataga agaagaaggt ggagagagag   1980
acagagacag atccattcga ttagtgaacg gatctcgacg gtatcggtta acttttaaaa   2040
gaaaaggggg gattgggggg tacagtgcag gggaaagaat agtagacata atagcaacag   2100
acatacaaac taaagaatta caaaaacaaa ttacaaaaat tcaaaatttt ccgatcacga   2160
gactagcctc gagaagcttg atcgatggct ccggtgcccg tcagtgggca gagcgcacat   2220
cgcccacagt ccccgagaag ttggggggag gggtcggcaa ttgaaccggt gcctagagaa   2280
ggtggcgcgg ggtaaactgg gaaagtgatg tcgtgtactg gctccgcctt tttcccgagg   2340
gtgggggaga accgtatata agtgcagtag tcgccgtgaa cgttcttttt cgcaacgggt   2400
ttgccgccag aacacaggtg tcgtgacgcg gatccaggcc taagcttacg cgtcctagcg   2460
ctaccggtcg ccaccatggt gagcaagggc gaggagctgt tcaccggggt ggtgcccatc   2520
ctggtcgagc tggacggcga cgtaaacggc cacaagttca gcgtgtccgg cgagggcgag   2580
```

```
ggcgatgcca cctacggcaa gctgaccctg aagttcatct gcaccaccgg caagctgccc   2640
gtgccctggc ccaccctcgt gaccaccctg acctacggcg tgcagtgctt cagccgctac   2700
cccgaccaca tgaagcagca cgacttcttc aagtccgcca tgcccgaagg ctacgtccag   2760
gagcgcacca tcttcttcaa ggacgacggc aactacaaga cccgcgccga ggtgaagttc   2820
gagggcgaca ccctggtgaa ccgcatcgag ctgaagggca tcgacttcaa ggaggacggc   2880
aacatcctgg ggcacaagct ggagtacaac tacaacagcc acaacgtcta tatcatggcc   2940
gacaagcaga agaacggcat caaggtgaac ttcaagatcc gccacaacat cgaggacggc   3000
agcgtgcagc tcgccgacca ctaccagcag aacaccccca tcggcgacgg ccccgtgctg   3060
ctgcccgaca accactacct gagcacccag tccgccctga gcaaagaccc caacgagaag   3120
cgcgatcaca tggtcctgct ggagttcgtg accgccgccg ggatcactct cggcatggac   3180
gagctgtaca agtccggagt gaaacagact ttgaattttg accttctgaa gttggcagga   3240
gacgttgagt ccaaccctgg gcccatggcc ttaccagtga ccgccttgct cctgccgctg   3300
gccttgctgc tccacgccgc caggccggat gttgtgatga ctcagtctcc actctccctg   3360
cccgtcaccc ctggagagcc ggcctccatc tcctgcagat ctagtcagag ccttgtacac   3420
agtaatgcca acacctattt acattggtac ctgcagaagc cagggcagtc tccacagctc   3480
ctgatctata aagtttccaa ccgattttct ggggtccctg acaggttcag tggcagtgga   3540
tcaggcacag attttacact gaaaatcagc agagtggagg ctgaggatgt tggggtttat   3600
tactgctctc aaaatacaca tgttcctcct acgtttggcc aggggaccaa gctggagatc   3660
aaacgtggtg gaggcggttc aggcggaggt ggctctggcg gtggcggatc gcaggtgcag   3720
ctggtgcagt ctggagctga ggtgaagaag cctggggcct cagtgaaggt ctcctgcaag   3780
gcttctggat acaccttcac cgactatgaa atgcactggg tgcgacaggc ccctggacaa   3840
gggcttgagt ggatgggagc tcttgatcct aaaactggtg atactgccta cagtcagaag   3900
ttcaagggca gagtcacgct gaccgcggac gaatccacga gcacagccta catggagctg   3960
agcagcctga gatctgagga cacggccgtg tattactgta caagattcta ctcctatact   4020
tactggggcc agggaaccct ggtcaccgtc tcctcaacca cgacgccagc gccgcgacca   4080
ccaacaccgg cgcccaccat cgcgtcgcag cccctgtccc tgcgcccaga ggcgtgccgg   4140
ccagcggcgg ggggcgcagt gcacacgagg gggctggact tcgcctgtga tatctacatc   4200
tgggcgccct tggccgggac ttgtggggtc cttctcctgt cactggttat caccagagtg   4260
aagttcagca ggagcgcaga cgcccccgcg taggtcgacc tcgagggaat tccgataatc   4320
aacctctgga ttacaaaatt tgtgaaagat tgactggtat tcttaactat gttgctcctt   4380
ttacgctatg tggatacgct gctttaatgc ctttgtatca tgctattgct tcccgtatgg   4440
ctttcatttt ctcctccttg tataaatcct ggttgctgtc tctttatgag gagttgtggc   4500
ccgttgtcag gcaacgtggc gtggtgtgca ctgtgtttgc tgacgcaacc cccactggtt   4560
ggggcattgc caccacctgt cagctccttt ccgggacttt cgctttcccc ctccctattg   4620
ccacggcgga actcatcgcc gcctgccttg cccgctgctg gacaggggct cggctgttgg   4680
gcactgacaa ttccgtggtg ttgtcgggga agctgacgtc ctttccatgg ctgctcgcct   4740
gtgttgccac ctggattctg cgcgggacgt ccttctgcta cgtcccttcg gccctcaatc   4800
cagcggacct tccttcccgc ggcctgctgc cggctctgcg gcctcttccg cgtcttcgcc   4860
ttcgccctca gacgagtcgg atctcccttt gggccgcctc cccgcatcgg gaattcgagc   4920
```

```
tcggtacctt taagaccaat gacttacaag gcagctgtag atcttagcca ctttttaaaa   4980
gaaaaggggg gactggaagg gctaattcac tcccaacgaa gacaagatgg gatcaattca   5040
ccatgggaat aacttcgtat agcatacatt atacgaagtt atgctgcttt ttgcttgtac   5100
tgggtctctc tggttagacc agatctgagc ctgggagctc tctggctaac tagggaaccc   5160
actgcttaag cctcaataaa gcttgccttg agtgcttcaa gtagtgtgtg cccgtctgtt   5220
gtgtgactct ggtaactaga gatccctcag acccttttag tcagtgtgga aaatctctag   5280
cagcatctag aattaattcc gtgtattcta tagtgtcacc taaatcgtat gtgtatgata   5340
cataaggtta tgtattaatt gtagccgcgt tctaacgaca atatgtacaa gcctaattgt   5400
gtagcatctg gcttactgaa gcagacccta tcatctctct cgtaaactgc cgtcagagtc   5460
ggtttggttg gacgaacctt ctgagtttct ggtaacgccg tcccgcaccc ggaaatggtc   5520
agcgaaccaa tcagcagggt catcgctagc cagatcctct acgccggacg catcgtggcc   5580
ggcatcaccg gcgccacagg tgcggttgct ggcgcctata tcgccgacat caccgatggg   5640
gaagatcggg ctcgccactt cgggctcatg agcgcttgtt tcggcgtggg tatggtggca   5700
ggccccgtgg ccgggggact gttgggcgcc atctccttgc atgcaccatt ccttgcggcg   5760
gcggtgctca acggcctcaa cctactactg ggctgcttcc taatgcagga gtcgcataag   5820
ggagagcgtc gaatggtgca ctctcagtac aatctgctct gatgccgcat agttaagcca   5880
gccccgacac ccgccaacac ccgctgacgc gccctgacgg gcttgtctgc tcccggcatc   5940
cgcttacaga caagctgtga ccgtctccgg gagctgcatg tgtcagaggt tttcaccgtc   6000
atcaccgaaa cgcgcgagac gaaagggcct cgtgatacgc ctatttttat aggttaatgt   6060
catgataata atggtttctt agacgtcagg tggcactttt cggggaaatg tgcgcggaac   6120
ccctatttgt ttatttttct aaatacattc aaatatgtat ccgctcatga gacaataacc   6180
ctgataaatg cttcaataat attgaaaaag gaagagtatg agtattcaac atttccgtgt   6240
cgcccttatt cccttttttg cggcattttg ccttcctgtt tttgctcacc cagaaacgct   6300
ggtgaaagta aaagatgctg aagatcagtt gggtgcacga gtgggttaca tcgaactgga   6360
tctcaacagc ggtaagatcc ttgagagttt tcgccccgaa gaacgttttc caatgatgag   6420
cacttttaaa gttctgctat gtggcgcggt attatcccgt attgacgccg ggcaagagca   6480
actcggtcgc cgcatacact attctcagaa tgacttggtt gagtactcac cagtcacaga   6540
aaagcatctt acggatggca tgacagtaag agaattatgc agtgctgcca taaccatgag   6600
tgataacact gcggccaact tacttctgac aacgatcgga ggaccgaagg agctaaccgc   6660
ttttttgcac aacatggggg atcatgtaac tcgccttgat cgttgggaac cggagctgaa   6720
tgaagccata ccaaacgacg agcgtgacac cacgatgcct gtagcaatgg caacaacgtt   6780
gcgcaaacta ttaactggcg aactacttac tctagcttcc cggcaacaat taatagactg   6840
gatggaggcg gataaagttg caggaccact tctgcgctcg gcccttccgg ctggctggtt   6900
tattgctgat aaatctggag ccggtgagcg tgggtctcgc ggtatcattg cagcactggg   6960
gccagatggt aagccctccc gtatcgtagt tatctacacg acggggagtc aggcaactat   7020
ggatgaacga aatagacaga tcgctgagat aggtgcctca ctgattaagc attggtaact   7080
gtcagaccaa gtttactcat atatacttta gattgattta aaacttcatt tttaatttaa   7140
aaggatctag gtgaagatcc tttttgataa tctcatgacc aaaatccctt aacgtgagtt   7200
ttcgttccac tgagcgtcag accccgtaga aaagatcaaa ggatcttctt gagatccttt   7260
ttttctgcgc gtaatctgct gcttgcaaac aaaaaaacca ccgctaccag cggtggtttg   7320
```

```
tttgccggat caagagctac caactctttt tccgaaggta actggcttca gcagagcgca   7380
gataccaaat actgtccttc tagtgtagcc gtagttaggc caccacttca agaactctgt   7440
agcaccgcct acatacctcg ctctgctaat cctgttacca gtggctgctg ccagtggcga   7500
taagtcgtgt cttaccgggt tggactcaag acgatagtta ccggataagg cgcagcggtc   7560
gggctgaacg gggggttcgt gcacacagcc cagcttggag cgaacgacct acaccgaact   7620
gagataccta cagcgtgagc attgagaaag cgccacgctt cccgaaggga gaaaggcgga   7680
caggtatccg gtaagcggca gggtcggaac aggagagcgc acgagggagc ttccaggggg   7740
aaacgcctgg tatctttata gtcctgtcgg gtttcgccac ctctgacttg agcgtcgatt   7800
tttgtgatgc tcgtcagggg ggcggagcct atggaaaaac gccagcaacg cggccttttt   7860
acggttcctg gccttttgct ggccttttgc tcacatgttc tttcctgcgt tatcccctga   7920
ttctgtggat aaccgtatta ccgcctttga gtgagctgat accgctcgcc gcagccgaac   7980
gaccgagcgc agcgagtcag tgagcgagga agcggaagag cgcccaatac gcaaaccgcc   8040
tctccccgcg cgttggccga ttcattaatg cagctgtgga atgtgtgtca gttagggtgt   8100
ggaaagtccc caggctcccc agcaggcaga agtatgcaaa gcatgcatct caattagtca   8160
gcaaccaggt gtggaaagtc cccaggctcc ccagcaggca gaagtatgca aagcatgcat   8220
ctcaattagt cagcaaccat agtcccgccc ctaactccgc ccatcccgcc cctaactccg   8280
cccagttccg cccattctcc gccccatggc tgactaattt tttttattta tgcagaggcc   8340
gaggccgcct cggcctctga gctattccag aagtagtgag gaggcttttt tggaggccta   8400
ggcttttgca aaaagcttgg acacaagaca ggcttgcgag atatgtttga gaataccact   8460
ttatcccgcg tcagggagag gcagtgcgta aaaagacgcg gactcatgtg aaatactggt   8520
ttttagtgcg ccagatctct ataatctcgc gcaacctatt ttcccctcga acacttttta   8580
agccgtagat aaacaggctg ggacacttca catgagcgaa aaatacatcg tcacctggga   8640
catgttgcag atccatgcac gtaaactcgc aagccgactg atgccttctg aacaatggaa   8700
aggcattatt gccgtaagcc gtggcggtct gtaccgggtg cgttactggc gcgtgaactg   8760
ggtattcgtc atgtcgatac cgtttgtatt tccagctacg atcacgacaa ccagcgcgag   8820
cttaaagtgc tgaaacgcgc agaaggcgat ggcgaaggct tcatcgttat tgatgacctg   8880
gtggataccg gtggtactgc ggttgcgatt cgtgaaatgt atccaaaagc gcactttgtc   8940
accatcttcg caaaaccggc tggtcgtccg ctggttgatg actatgttgt tgatatcccg   9000
caagatacct ggattgaaca gccgtgggat atgggcgtcg tattcgtccc gccaatctcc   9060
ggtcgctaat cttttcaacg cctggcactg ccgggcgttg ttcttttttaa cttcaggcgg   9120
gttacaatag tttccagtaa gtattctgga ggctgcatcc atgacacagg caaacctgag   9180
cgaaaccctg ttcaaacccc gctttaaaca tcctgaaacc tcgacgctag tccgccgctt   9240
taatcacggc gcacaaccgc ctgtgcagtc ggcccttgat ggtaaaacca tccctcactg   9300
gtatcgcatg attaaccgtc tgatgtggat ctggcgcggc attgacccac gcgaaatcct   9360
cgacgtccag gcacgtattg tgatgagcga tgccgaacgt accgacgatg atttatacga   9420
tacggtgatt ggctaccgtg gcggcaactg gatttatgag tgggccccgg atctttgtga   9480
aggaacctta cttctgtggt gtgacataat tggacaaact acctacagag atttaaagct   9540
ctaaggtaaa tataaaattt ttaagtgtat aatgtgttaa actactgatt ctaattgttt   9600
gtgtatttta gattccaacc tatggaactg atgaatggga gcagtggtgg aatgccttta   9660
```

```
atgaggaaaa cctgttttgc tcagaagaaa tgccatctag tgatgatgag gctactgctg   9720
actctcaaca ttctactcct ccaaaaaaga agagaaaggt agaagacccc aaggactttc   9780
cttcagaatt gctaagtttt ttgagtcatg ctgtgtttag taatagaact cttgcttgct   9840
ttgctattta caccacaaag gaaaaagctg cactgctata caagaaaatt atggaaaaat   9900
attctgtaac ctttataagt aggcataaca gttataatca taacatactg tttttttctta   9960
ctccacacag gcatagagtg tctgctatta ataactatgc tcaaaaattg tgtaccttta  10020
gctttttaat ttgtaaaggg gttaataagg aatatttgat gtatagtgcc ttgactagag  10080
atcataatca gccataccac atttgtagag gttttacttg ctttaaaaaa cctcccacac  10140
ctccccctga acctgaaaca taaaatgaat gcaattgttg ttgttaactt gtttattgca  10200
gcttataatg gttacaaata aagcaatagc atcacaaatt tcacaaataa agcatttttt  10260
tcactgcatt ctagttgtgg tttgtccaaa ctcatcaatg tatcttatca tgtctggatc  10320
aactggataa ctcaagctaa ccaaaatcat cccaaacttc ccaccccata ccctattacc  10380
actgccaatt acctagtggt ttcatttact ctaaacctgt gattcctctg aattattttc  10440
attttaaaga aattgtattt gttaaatatg tactacaaac ttagtag                10487
```

```
<210> SEQ ID NO 27
<211> LENGTH: 10790
<212> TYPE: DNA
<213> ORGANISM: Artificial sequence
<220> FEATURE:
<223> OTHER INFORMATION: pWPT-eGFP-F2A-GPC3-Z

<400> SEQUENCE: 27
```

```
ttggaagggc taattcactc ccaaagaaga caagatatcc ttgatctgtg gatctaccac     60
acacaaggct acttccctga ttagcagaac tacacaccag ggccaggggt cagatatcca    120
ctgacctttg gatggtgcta caagctagta ccagttgagc cagataaggt agaagaggcc    180
aataaaggag agaacaccag cttgttacac cctgtgagcc tgcatgggat ggatgacccg    240
gagagagaag tgttagagtg gaggtttgac agccgcctag catttcatca cgtggcccga    300
gagctgcatc cggagtactt caagaactgc tgatatcgag cttgctacaa gggactttcc    360
gctggggact ttccagggag gcgtggcctg ggcgggactg gggagtggcg agccctcaga    420
tcctgcatat aagcagctgc tttttgcctg tactgggtct ctctggttag accagatctg    480
agcctgggag ctctctggct aactagggaa cccactgctt aagcctcaat aaagcttgcc    540
ttgagtgctt caagtagtgt gtgcccgtct gttgtgtgac tctggtaact agagatccct    600
cagacccttt tagtcagtgt ggaaaatctc tagcagtggc gcccgaacag ggacttgaaa    660
gcgaaaggga aaccagagga gctctctcga cgcaggactc ggcttgctga agcgcgcacg    720
gcaagaggcg aggggcggcg actggtgagt acgccaaaaa ttttgactag cggaggctag    780
aaggagagag atgggtgcga gagcgtcagt attaagcggg ggagaattag atcgcgatgg    840
gaaaaaattc ggttaaggcc agggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg gccgctgatc ttcagacctg gaggaggaga tatgagggac aattggagaa   1200
gtgaattata taaatataaa gtagtaaaaa ttgaaccatt aggagtagca cccaccaagg   1260
```

```
caaagagaag agtggtgcag agagaaaaaa gagcagtggg aataggagct ttgttccttg   1320
ggttcttggg agcagcagga agcactatgg gcgcagcgtc aatgacgctg acggtacagg   1380
ccagacaatt attgtctggt atagtgcagc agcagaacaa tttgctgagg gctattgagg   1440
cgcaacagca tctgttgcaa ctcacagtct ggggcatcaa gcagctccag gcaagaatcc   1500
tggctgtgga aagataccta aaggatcaac agctcctggg gatttggggt tgctctggaa   1560
aactcatttg caccactgct gtgccttgga atgctagttg gagtaataaa tctctggaac   1620
agatttggaa tcacacgacc tggatggagt gggacagaga aattaacaat tacacaagct   1680
taatacactc cttaattgaa gaatcgcaaa accagcaaga aaagaatgaa caagaattat   1740
tggaattaga taaatgggca agtttgtgga attggtttaa cataacaaat tggctgtggt   1800
atataaaatt attcataatg atagtaggag gcttggtagg tttaagaata gtttttgctg   1860
tactttctat agtgaataga gttaggcagg gatattcacc attatcgttt cagacccacc   1920
tcccaacccc gaggggaccc gacaggcccg aaggaataga agaagaaggt ggagagagag   1980
acagagacag atccattcga ttagtgaacg gatctcgacg gtatcggtta acttttaaaa   2040
gaaaaggggg gattgggggg tacagtgcag gggaaagaat agtagacata atagcaacag   2100
acatacaaac taaagaatta caaaaacaaa ttacaaaaat tcaaaatttt ccgatcacga   2160
gactagcctc gagaagcttg atcgatggct ccggtgcccg tcagtgggca gagcgcacat   2220
cgcccacagt ccccgagaag ttggggggag gggtcggcaa ttgaaccggt gcctagagaa   2280
ggtggcgcgg ggtaaactgg gaaagtgatg tcgtgtactg gctccgcctt tttcccgagg   2340
gtgggggaga accgtatata agtgcagtag tcgccgtgaa cgttcttttt cgcaacgggt   2400
ttgccgccag aacacaggtg tcgtgacgcg gatccaggcc taagcttacg cgtcctagcg   2460
ctaccggtcg ccaccatggt gagcaagggc gaggagctgt tcaccggggt ggtgcccatc   2520
ctggtcgagc tggacggcga cgtaaacggc cacaagttca gcgtgtccgg cgagggcgag   2580
ggcgatgcca cctacggcaa gctgaccctg aagttcatct gcaccaccgg caagctgccc   2640
gtgccctggc ccaccctcgt gaccaccctg acctacggcg tgcagtgctt cagccgctac   2700
cccgaccaca tgaagcagca cgacttcttc aagtccgcca tgcccgaagg ctacgtccag   2760
gagcgcacca tcttcttcaa ggacgacggc aactacaaga cccgcgccga ggtgaagttc   2820
gagggcgaca ccctggtgaa ccgcatcgag ctgaagggca tcgacttcaa ggaggacggc   2880
aacatcctgg ggcacaagct ggagtacaac tacaacagcc acaacgtcta tatcatggcc   2940
gacaagcaga agaacggcat caaggtgaac ttcaagatcc gccacaacat cgaggacggc   3000
agcgtgcagc tcgccgacca ctaccagcag aacaccccca tcggcgacgg ccccgtgctg   3060
ctgcccgaca accactacct gagcacccag tccgccctga gcaaagaccc caacgagaag   3120
cgcgatcaca tggtcctgct ggagttcgtg accgccgccg ggatcactct cggcatggac   3180
gagctgtaca agtccggagt gaaacagact ttgaattttg accttctgaa gttggcagga   3240
gacgttgagt ccaaccctgg gcccatggcc ttaccagtga ccgccttgct cctgccgctg   3300
gccttgctgc tccacgccgc caggccggat gttgtgatga ctcagtctcc actctccctg   3360
cccgtcaccc ctggagagcc ggcctccatc tcctgcagat ctagtcagag ccttgtacac   3420
agtaatgcca acacctattt acattggtac ctgcagaagc cagggcagtc tccacagctc   3480
ctgatctata aagtttccaa ccgattttct ggggtccctg acaggttcag tggcagtgga   3540
tcaggcacag attttacact gaaaatcagc agagtggagg ctgaggatgt tggggtttat   3600
```

-continued

```
tactgctctc aaaatacaca tgttcctcct acgtttggcc aggggaccaa gctggagatc   3660
aaacgtggtg gaggcggttc aggcggaggt ggctctggcg gtggcggatc gcaggtgcag   3720
ctggtgcagt ctggagctga ggtgaagaag cctggggcct cagtgaaggt ctcctgcaag   3780
gcttctggat acaccttcac cgactatgaa atgcactggg tgcgacaggc ccctggacaa   3840
gggcttgagt ggatgggagc tcttgatcct aaaactggtg atactgccta cagtcagaag   3900
ttcaagggca gagtcacgct gaccgcggac gaatccacga gcacagccta catggagctg   3960
agcagcctga gatctgagga cacggccgtg tattactgta caagattcta ctcctatact   4020
tactggggcc agggaaccct ggtcaccgtc tcctcaacca cgacgccagc gccgcgacca   4080
ccaacaccgg cgcccaccat cgcgtcgcag cccctgtccc tgcgcccaga ggcgtgccgg   4140
ccagcggcgg ggggcgcagt gcacacgagg gggctggact tcgcctgtga tatctacatc   4200
tgggcgccct tggccgggac ttgtggggtc cttctcctgt cactggttat caccagagtg   4260
aagttcagca ggagcgcaga cgcccccgcg taccagcagg gccagaacca gctctataac   4320
gagctcaatc taggacgaag agaggagtac gatgttttgg acaagagacg tggccgggac   4380
cctgagatgg ggggaaagcc gcagagaagg aagaaccctc aggaaggcct gtacaatgaa   4440
ctgcagaaag ataagatggc ggaggcctac agtgagattg ggatgaaagg cgagcgccgg   4500
aggggcaagg ggcacgatgg cctttaccag ggtctcagta cagccaccaa ggacacctac   4560
gacgcccttc acatgcaggc cctgccccct cgctaggtcg acctcgaggg aattccgata   4620
atcaacctct ggattacaaa atttgtgaaa gattgactgg tattcttaac tatgttgctc   4680
cttttacgct atgtggatac gctgctttaa tgcctttgta tcatgctatt gcttcccgta   4740
tggctttcat tttctcctcc ttgtataaat cctggttgct gtctctttat gaggagttgt   4800
ggcccgttgt caggcaacgt ggcgtggtgt gcactgtgtt tgctgacgca acccccactg   4860
gttggggcat tgccaccacc tgtcagctcc tttccgggac tttcgctttc cccctcccta   4920
ttgccacggc ggaactcatc gccgcctgcc ttgcccgctg ctggacaggg gctcggctgt   4980
tgggcactga caattccgtg gtgttgtcgg ggaagctgac gtcctttcca tggctgctcg   5040
cctgtgttgc cacctggatt ctgcgcggga cgtccttctg ctacgtccct tcggccctca   5100
atccagcgga ccttccttcc cgcggcctgc tgccggctct gcggcctctt ccgcgtcttc   5160
gccttcgccc tcagacgagt cggatctccc tttgggccgc ctccccgcat cgggaattcg   5220
agctcggtac ctttaagacc aatgacttac aaggcagctg tagatcttag ccacttttta   5280
aaagaaaagg ggggactgga agggctaatt cactcccaac gaagacaaga tgggatcaat   5340
tcaccatggg aataacttcg tatagcatac attatacgaa gttatgctgc tttttgcttg   5400
tactgggtct ctctggttag accagatctg agcctgggag ctctctggct aactagggaa   5460
cccactgctt aagcctcaat aaagcttgcc ttgagtgctt caagtagtgt gtgcccgtct   5520
gttgtgtgac tctggtaact agagatccct cagacccttt tagtcagtgt ggaaaatctc   5580
tagcagcatc tagaattaat tccgtgtatt ctatagtgtc acctaaatcg tatgtgtatg   5640
atacataagg ttatgtatta attgtagccg cgttctaacg acaatatgta caagcctaat   5700
tgtgtagcat ctggcttact gaagcagacc ctatcatctc tctcgtaaac tgccgtcaga   5760
gtcggtttgg ttggacgaac cttctgagtt tctggtaacg ccgtcccgca cccggaaatg   5820
gtcagcgaac caatcagcag ggtcatcgct agccagatcc tctacgccgg acgcatcgtg   5880
gccggcatca ccggcgccac aggtgcggtt gctggcgcct atatcgccga catcaccgat   5940
ggggaagatc gggctcgcca cttcgggctc atgagcgctt gtttcggcgt gggtatggtg   6000
```

```
gcaggccccg tggccggggg actgttgggc gccatctcct tgcatgcacc attccttgcg   6060
gcggcggtgc tcaacggcct caacctacta ctgggctgct tcctaatgca ggagtcgcat   6120
aagggagagc gtcgaatggt gcactctcag tacaatctgc tctgatgccg catagttaag   6180
ccagccccga cacccgccaa cacccgctga cgcgccctga cgggcttgtc tgctcccggc   6240
atccgcttac agacaagctg tgaccgtctc cgggagctgc atgtgtcaga ggttttcacc   6300
gtcatcaccg aaacgcgcga gacgaaaggg cctcgtgata cgcctatttt tataggttaa   6360
tgtcatgata ataatggttt cttagacgtc aggtggcact tttcggggaa atgtgcgcgg   6420
aacccctatt tgtttatttt tctaaataca ttcaaatatg tatccgctca tgagacaata   6480
accctgataa atgcttcaat aatattgaaa aaggaagagt atgagtattc aacatttccg   6540
tgtcgccctt attccctttt ttgcggcatt ttgccttcct gtttttgctc acccagaaac   6600
gctggtgaaa gtaaaagatg ctgaagatca gttgggtgca cgagtgggtt acatcgaact   6660
ggatctcaac agcggtaaga tccttgagag ttttcgcccc gaagaacgtt ttccaatgat   6720
gagcactttt aaagttctgc tatgtggcgc ggtattatcc cgtattgacg ccgggcaaga   6780
gcaactcggt cgccgcatac actattctca gaatgacttg gttgagtact caccagtcac   6840
agaaaagcat cttacggatg gcatgacagt aagagaatta tgcagtgctg ccataaccat   6900
gagtgataac actgcggcca acttacttct gacaacgatc ggaggaccga aggagctaac   6960
cgcttttttg cacaacatgg gggatcatgt aactcgcctt gatcgttggg aaccggagct   7020
gaatgaagcc ataccaaacg acgagcgtga caccacgatg cctgtagcaa tggcaacaac   7080
gttgcgcaaa ctattaactg gcgaactact tactctagct tcccggcaac aattaataga   7140
ctggatggag gcggataaag ttgcaggacc acttctgcgc tcggcccttc cggctggctg   7200
gtttattgct gataaatctg gagccggtga gcgtgggtct cgcggtatca ttgcagcact   7260
ggggccagat ggtaagccct cccgtatcgt agttatctac acgacgggga gtcaggcaac   7320
tatggatgaa cgaaatagac agatcgctga gataggtgcc tcactgatta agcattggta   7380
actgtcagac caagtttact catatatact ttagattgat ttaaaacttc atttttaatt   7440
taaaaggatc taggtgaaga tcctttttga taatctcatg accaaaatcc cttaacgtga   7500
gttttcgttc cactgagcgt cagaccccgt agaaaagatc aaaggatctt cttgagatcc   7560
tttttttctg cgcgtaatct gctgcttgca aacaaaaaaa ccaccgctac cagcggtggt   7620
ttgtttgccg gatcaagagc taccaactct ttttccgaag gtaactggct tcagcagagc   7680
gcagatacca aatactgtcc ttctagtgta gccgtagtta ggccaccact tcaagaactc   7740
tgtagcaccg cctacatacc tcgctctgct aatcctgtta ccagtggctg ctgccagtgg   7800
cgataagtcg tgtcttaccg ggttggactc aagacgatag ttaccggata aggcgcagcg   7860
gtcgggctga acggggggtt cgtgcacaca gcccagcttg gagcgaacga cctacaccga   7920
actgagatac ctacagcgtg agcattgaga aagcgccacg cttcccgaag ggagaaaggc   7980
ggacaggtat ccggtaagcg gcagggtcgg aacaggagag cgcacgaggg agcttccagg   8040
gggaaacgcc tggtatcttt atagtcctgt cgggtttcgc cacctctgac ttgagcgtcg   8100
atttttgtga tgctcgtcag gggggcggag cctatggaaa aacgccagca acgcggcctt   8160
tttacggttc ctggcctttt gctggccttt tgctcacatg ttctttcctg cgttatcccc   8220
tgattctgtg gataaccgta ttaccgcctt tgagtgagct gataccgctc gccgcagccg   8280
aacgaccgag cgcagcgagt cagtgagcga ggaagcggaa gagcgcccaa tacgcaaacc   8340
```

```
gcctctcccc gcgcgttggc cgattcatta atgcagctgt ggaatgtgtg tcagttaggg   8400

tgtggaaagt ccccaggctc cccagcaggc agaagtatgc aaagcatgca tctcaattag   8460

tcagcaacca ggtgtggaaa gtccccaggc tccccagcag gcagaagtat gcaaagcatg   8520

catctcaatt agtcagcaac catagtcccg cccctaactc cgcccatccc gcccctaact   8580

ccgcccagtt ccgcccattc tccgccccat ggctgactaa ttttttttat ttatgcagag   8640

gccgaggccg cctcggcctc tgagctattc cagaagtagt gaggaggctt ttttggaggc   8700

ctaggctttt gcaaaaagct tggacacaag acaggcttgc gagatatgtt tgagaatacc   8760

actttatccc gcgtcaggga gaggcagtgc gtaaaaagac gcggactcat gtgaaatact   8820

ggtttttagt gcgccagatc tctataatct cgcgcaacct attttcccct cgaacacttt   8880

ttaagccgta gataaacagg ctgggacact tcacatgagc gaaaaataca tcgtcacctg   8940

ggacatgttg cagatccatg cacgtaaact cgcaagccga ctgatgcctt ctgaacaatg   9000

gaaaggcatt attgccgtaa gccgtggcgg tctgtaccgg gtgcgttact ggcgcgtgaa   9060

ctgggtattc gtcatgtcga taccgtttgt atttccagct acgatcacga caaccagcgc   9120

gagcttaaag tgctgaaacg cgcagaaggc gatggcgaag gcttcatcgt tattgatgac   9180

ctggtggata ccggtggtac tgcggttgcg attcgtgaaa tgtatccaaa agcgcacttt   9240

gtcaccatct tcgcaaaacc ggctggtcgt ccgctggttg atgactatgt tgttgatatc   9300

ccgcaagata cctggattga acagccgtgg gatatgggcg tcgtattcgt cccgccaatc   9360

tccggtcgct aatcttttca acgcctggca ctgccgggcg ttgttctttt taacttcagg   9420

cgggttacaa tagtttccag taagtattct ggaggctgca tccatgacac aggcaaacct   9480

gagcgaaacc ctgttcaaac cccgctttaa acatcctgaa acctcgacgc tagtccgccg   9540

ctttaatcac ggcgcacaac cgcctgtgca gtcggccctt gatggtaaaa ccatccctca   9600

ctggtatcgc atgattaacc gtctgatgtg gatctggcgc ggcattgacc cacgcgaaat   9660

cctcgacgtc caggcacgta ttgtgatgag cgatgccgaa cgtaccgacg atgatttata   9720

cgatacggtg attggctacc gtggcggcaa ctggatttat gagtgggccc cggatctttg   9780

tgaaggaacc ttacttctgt ggtgtgacat aattggacaa actacctaca gagatttaaa   9840

gctctaaggt aaatataaaa tttttaagtg tataatgtgt taaactactg attctaattg   9900

tttgtgtatt ttagattcca acctatggaa ctgatgaatg ggagcagtgg tggaatgcct   9960

ttaatgagga aaacctgttt tgctcagaag aaatgccatc tagtgatgat gaggctactg  10020

ctgactctca acattctact cctccaaaaa agaagagaaa ggtagaagac cccaaggact  10080

ttccttcaga attgctaagt tttttgagtc atgctgtgtt tagtaataga actcttgctt  10140

gctttgctat ttacaccaca aaggaaaaag ctgcactgct atacaagaaa attatggaaa  10200

aatattctgt aacctttata agtaggcata acagttataa tcataacata ctgttttttc  10260

ttactccaca caggcataga gtgtctgcta ttaataacta tgctcaaaaa ttgtgtacct  10320

ttagcttttt aatttgtaaa ggggttaata aggaatattt gatgtatagt gccttgacta  10380

gagatcataa tcagccatac cacatttgta gaggttttac ttgctttaaa aaacctccca  10440

cacctccccc tgaacctgaa acataaaatg aatgcaattg ttgttgttaa cttgtttatt  10500

gcagcttata atggttacaa ataaagcaat agcatcacaa atttcacaaa taaagcattt  10560

ttttcactgc attctagttg tggtttgtcc aaactcatca atgtatctta tcatgtctgg  10620

atcaactgga taactcaagc taaccaaaat catcccaaac ttcccacccc ataccctatt  10680

accactgcca attacctagt ggtttcattt actctaaacc tgtgattcct ctgaattatt  10740
```

```
ttcattttaa agaaattgta tttgttaaat atgtactaca aacttagtag           10790


<210> SEQ ID NO 28
<211> LENGTH: 10916
<212> TYPE: DNA
<213> ORGANISM: Artificial sequence
<220> FEATURE:
<223> OTHER INFORMATION: pWPT-eGFP-F2A-GPC3-BBZ

<400> SEQUENCE: 28

ttggaagggc taattcactc ccaaagaaga caagatatcc ttgatctgtg gatctaccac     60

acacaaggct acttccctga ttagcagaac tacacaccag ggccaggggt cagatatcca    120

ctgacctttg gatggtgcta caagctagta ccagttgagc cagataaggt agaagaggcc    180

aataaaggag agaacaccag cttgttacac cctgtgagcc tgcatgggat ggatgacccg    240

gagagagaag tgttagagtg gaggtttgac agccgcctag catttcatca cgtggcccga    300

gagctgcatc cggagtactt caagaactgc tgatatcgag cttgctacaa gggactttcc    360

gctggggact ttccagggag gcgtggcctg ggcgggactg gggagtggcg agccctcaga    420

tcctgcatat aagcagctgc tttttgcctg tactgggtct ctctggttag accagatctg    480

agcctgggag ctctctggct aactagggaa cccactgctt aagcctcaat aaagcttgcc    540

ttgagtgctt caagtagtgt gtgcccgtct gttgtgtgac tctggtaact agagatccct    600

cagacccttt tagtcagtgt ggaaaatctc tagcagtggc gcccgaacag ggacttgaaa    660

gcgaaaggga aaccagagga gctctctcga cgcaggactc ggcttgctga agcgcgcacg    720

gcaagaggcg aggggcggcg actggtgagt acgccaaaaa ttttgactag cggaggctag    780

aaggagagag atgggtgcga gagcgtcagt attaagcggg ggagaattag atcgcgatgg    840

gaaaaaattc ggttaaggcc agggggaaag aaaaaatata aattaaaaca tatagtatgg    900

gcaagcaggg agctagaacg attcgcagtt aatcctggcc tgttagaaac atcagaaggc    960

tgtagacaaa tactgggaca gctacaacca tcccttcaga caggatcaga agaacttaga   1020

tcattatata atacagtagc aaccctctat tgtgtgcatc aaaggataga gataaaagac   1080

accaaggaag ctttagacaa gatagaggaa gagcaaaaca aaagtaagac caccgcacag   1140

caagcggccg gccgctgatc ttcagacctg gaggaggaga tatgagggac aattggagaa   1200

gtgaattata taaatataaa gtagtaaaaa ttgaaccatt aggagtagca cccaccaagg   1260

caaagagaag agtggtgcag agagaaaaaa gagcagtggg aataggagct ttgttccttg   1320

ggttcttggg agcagcagga agcactatgg gcgcagcgtc aatgacgctg acggtacagg   1380

ccagacaatt attgtctggt atagtgcagc agcagaacaa tttgctgagg gctattgagg   1440

cgcaacagca tctgttgcaa ctcacagtct ggggcatcaa gcagctccag gcaagaatcc   1500

tggctgtgga aagataccta aaggatcaac agctcctggg gatttggggt tgctctggaa   1560

aactcatttg caccactgct gtgccttgga atgctagttg gagtaataaa tctctggaac   1620

agatttggaa tcacacgacc tggatggagt gggacagaga aattaacaat tacacaagct   1680

taatacactc cttaattgaa gaatcgcaaa accagcaaga aaagaatgaa caagaattat   1740

tggaattaga taaatgggca agtttgtgga attggtttaa cataacaaat tggctgtggt   1800

atataaaatt attcataatg atagtaggag gcttggtagg tttaagaata gtttttgctg   1860

tactttctat agtgaataga gttaggcagg gatattcacc attatcgttt cagacccacc   1920

tcccaacccc gaggggaccc gacaggcccg aaggaataga agaagaaggt ggagagagag   1980
```

```
acagagacag atccattcga ttagtgaacg gatctcgacg gtatcggtta acttttaaaa   2040
gaaaaggggg gattgggggg tacagtgcag gggaaagaat agtagacata atagcaacag   2100
acatacaaac taaagaatta caaaaacaaa ttacaaaaat tcaaaatttt ccgatcacga   2160
gactagcctc gagaagcttg atcgatggct ccggtgcccg tcagtgggca gagcgcacat   2220
cgcccacagt ccccgagaag ttggggggag gggtcggcaa ttgaaccggt gcctagagaa   2280
ggtggcgcgg ggtaaactgg gaaagtgatg tcgtgtactg gctccgcctt tttcccgagg   2340
gtgggggaga accgtatata agtgcagtag tcgccgtgaa cgttcttttt cgcaacgggt   2400
ttgccgccag aacacaggtg tcgtgacgcg gatccaggcc taagcttacg cgtcctagcg   2460
ctaccggtcg ccaccatggt gagcaagggc gaggagctgt tcaccggggt ggtgcccatc   2520
ctggtcgagc tggacggcga cgtaaacggc cacaagttca gcgtgtccgg cgagggcgag   2580
ggcgatgcca cctacggcaa gctgaccctg aagttcatct gcaccaccgg caagctgccc   2640
gtgccctggc ccaccctcgt gaccaccctg acctacggcg tgcagtgctt cagccgctac   2700
cccgaccaca tgaagcagca cgacttcttc aagtccgcca tgcccgaagg ctacgtccag   2760
gagcgcacca tcttcttcaa ggacgacggc aactacaaga cccgcgccga ggtgaagttc   2820
gagggcgaca ccctggtgaa ccgcatcgag ctgaagggca tcgacttcaa ggaggacggc   2880
aacatcctgg ggcacaagct ggagtacaac tacaacagcc acaacgtcta tatcatggcc   2940
gacaagcaga agaacggcat caaggtgaac ttcaagatcc gccacaacat cgaggacggc   3000
agcgtgcagc tcgccgacca ctaccagcag aacaccccca tcggcgacgg ccccgtgctg   3060
ctgcccgaca accactacct gagcacccag tccgccctga gcaaagaccc caacgagaag   3120
cgcgatcaca tggtcctgct ggagttcgtg accgccgccg ggatcactct cggcatggac   3180
gagctgtaca agtccggagt gaaacagact ttgaattttg accttctgaa gttggcagga   3240
gacgttgagt ccaaccctgg gcccatggcc ttaccagtga ccgccttgct cctgccgctg   3300
gccttgctgc tccacgccgc caggccggat gttgtgatga ctcagtctcc actctccctg   3360
cccgtcaccc ctggagagcc ggcctccatc tcctgcagat ctagtcagag ccttgtacac   3420
agtaatgcca acacctattt acattggtac ctgcagaagc cagggcagtc tccacagctc   3480
ctgatctata aagtttccaa ccgattttct ggggtccctg acaggttcag tggcagtgga   3540
tcaggcacag attttacact gaaaatcagc agagtggagg ctgaggatgt tggggtttat   3600
tactgctctc aaaatacaca tgttcctcct acgtttggcc aggggaccaa gctggagatc   3660
aaacgtggtg gaggcggttc aggcggaggt ggctctggcg gtggcggatc gcaggtgcag   3720
ctggtgcagt ctggagctga ggtgaagaag cctggggcct cagtgaaggt ctcctgcaag   3780
gcttctggat acaccttcac cgactatgaa atgcactggg tgcgacaggc ccctggacaa   3840
gggcttgagt ggatgggagc tcttgatcct aaaactggtg atactgccta cagtcagaag   3900
ttcaagggca gagtcacgct gaccgcggac gaatccacga gcacagccta catggagctg   3960
agcagcctga gatctgagga cacggccgtg tattactgta caagattcta ctcctatact   4020
tactggggcc agggaaccct ggtcaccgtc tcctcaacca cgacgccagc gccgcgacca   4080
ccaacaccgg cgcccaccat cgcgtcgcag cccctgtccc tgcgcccaga ggcgtgccgg   4140
ccagcggcgg ggggcgcagt gcacacgagg gggctggact tcgcctgtga tatctacatc   4200
tgggcgccct tggccgggac ttgtggggtc cttctcctgt cactggttat caccaaacgg   4260
ggcagaaaga aactcctgta tatattcaaa caaccattta tgagaccagt acaaactact   4320
caagaggaag atggctgtag ctgccgattt ccagaagaag aagaaggagg atgtgaactg   4380
```

```
agagtgaagt tcagcaggag cgcagacgcc cccgcgtacc agcagggcca gaaccagctc   4440
tataacgagc tcaatctagg acgaagagag gagtacgatg ttttggacaa gagacgtggc   4500
cgggaccctg agatgggggg aaagccgcag agaaggaaga accctcagga aggcctgtac   4560
aatgaactgc agaaagataa gatggcggag gcctacagtg agattgggat gaaaggcgag   4620
cgccggaggg gcaaggggca cgatggcctt taccagggtc tcagtacagc caccaaggac   4680
acctacgacg cccttcacat gcaggccctg ccccctcgct aggtcgacct cgagggaatt   4740
ccgataatca acctctggat tacaaaattt gtgaaagatt gactggtatt cttaactatg   4800
ttgctccttt tacgctatgt ggatacgctg ctttaatgcc tttgtatcat gctattgctt   4860
cccgtatggc tttcattttc tcctccttgt ataaatcctg gttgctgtct ctttatgagg   4920
agttgtggcc cgttgtcagg caacgtggcg tggtgtgcac tgtgtttgct gacgcaaccc   4980
ccactggttg gggcattgcc accacctgtc agctcctttc cgggactttc gctttccccc   5040
tccctattgc cacggcggaa ctcatcgccg cctgccttgc ccgctgctgg acaggggctc   5100
ggctgttggg cactgacaat tccgtggtgt tgtcggggaa gctgacgtcc tttccatggc   5160
tgctcgcctg tgttgccacc tggattctgc gcgggacgtc cttctgctac gtcccttcgg   5220
ccctcaatcc agcggacctt ccttcccgcg gcctgctgcc ggctctgcgg cctcttccgc   5280
gtcttcgcct tcgccctcag acgagtcgga tctccctttg ggccgcctcc ccgcatcggg   5340
aattcgagct cggtaccttt aagaccaatg acttacaagg cagctgtaga tcttagccac   5400
tttttaaaag aaaagggggg actggaaggg ctaattcact cccaacgaag acaagatggg   5460
atcaattcac catgggaata acttcgtata gcatacatta tacgaagtta tgctgctttt   5520
tgcttgtact gggtctctct ggttagacca gatctgagcc tgggagctct ctggctaact   5580
agggaaccca ctgcttaagc ctcaataaag cttgccttga gtgcttcaag tagtgtgtgc   5640
ccgtctgttg tgtgactctg gtaactagag atccctcaga cccttttagt cagtgtggaa   5700
aatctctagc agcatctaga attaattccg tgtattctat agtgtcacct aaatcgtatg   5760
tgtatgatac ataaggttat gtattaattg tagccgcgtt ctaacgacaa tatgtacaag   5820
cctaattgtg tagcatctgg cttactgaag cagaccctat catctctctc gtaaactgcc   5880
gtcagagtcg gtttggttgg acgaaccttc tgagtttctg gtaacgccgt cccgcacccg   5940
gaaatggtca gcgaaccaat cagcagggtc atcgctagcc agatcctcta cgccggacgc   6000
atcgtggccg gcatcaccgg cgccacaggt gcggttgctg gcgcctatat cgccgacatc   6060
accgatgggg aagatcgggc tcgccacttc gggctcatga gcgcttgttt cggcgtgggt   6120
atggtggcag gccccgtggc cgggggactg ttgggcgcca tctccttgca tgcaccattc   6180
cttgcggcgg cggtgctcaa cggcctcaac ctactactgg gctgcttcct aatgcaggag   6240
tcgcataagg gagagcgtcg aatggtgcac tctcagtaca atctgctctg atgccgcata   6300
gttaagccag ccccgacacc cgccaacacc cgctgacgcg ccctgacggg cttgtctgct   6360
cccggcatcc gcttacagac aagctgtgac cgtctccggg agctgcatgt gtcagaggtt   6420
ttcaccgtca tcaccgaaac gcgcgagacg aaagggcctc gtgatacgcc tatttttata   6480
ggttaatgtc atgataataa tggtttctta gacgtcaggt ggcacttttc ggggaaatgt   6540
gcgcggaacc cctatttgtt tatttttcta aatacattca aatatgtatc cgctcatgag   6600
acaataaccc tgataaatgc ttcaataata ttgaaaaagg aagagtatga gtattcaaca   6660
tttccgtgtc gcccttattc cctttttttgc ggcattttgc cttcctgttt ttgctcaccc   6720
```

-continued

```
agaaacgctg gtgaaagtaa aagatgctga agatcagttg ggtgcacgag tgggttacat   6780
cgaactggat ctcaacagcg gtaagatcct tgagagtttt cgccccgaag aacgttttcc   6840
aatgatgagc acttttaaag ttctgctatg tggcgcggta ttatcccgta ttgacgccgg   6900
gcaagagcaa ctcggtcgcc gcatacacta ttctcagaat gacttggttg agtactcacc   6960
agtcacagaa aagcatctta cggatggcat gacagtaaga gaattatgca gtgctgccat   7020
aaccatgagt gataacactg cggccaactt acttctgaca acgatcggag gaccgaagga   7080
gctaaccgct tttttgcaca acatggggga tcatgtaact cgccttgatc gttgggaacc   7140
ggagctgaat gaagccatac caaacgacga gcgtgacacc acgatgcctg tagcaatggc   7200
aacaacgttg cgcaaactat taactggcga actacttact ctagcttccc ggcaacaatt   7260
aatagactgg atggaggcgg ataaagttgc aggaccactt ctgcgctcgg cccttccggc   7320
tggctggttt attgctgata aatctggagc cggtgagcgt gggtctcgcg gtatcattgc   7380
agcactgggg ccagatggta agccctcccg tatcgtagtt atctacacga cggggagtca   7440
ggcaactatg gatgaacgaa atagacagat cgctgagata ggtgcctcac tgattaagca   7500
ttggtaactg tcagaccaag tttactcata tatactttag attgatttaa aacttcattt   7560
ttaatttaaa aggatctagg tgaagatcct ttttgataat ctcatgacca aaatccctta   7620
acgtgagttt tcgttccact gagcgtcaga ccccgtagaa aagatcaaag gatcttcttg   7680
agatcctttt tttctgcgcg taatctgctg cttgcaaaca aaaaaaccac cgctaccagc   7740
ggtggtttgt ttgccggatc aagagctacc aactcttttt ccgaaggtaa ctggcttcag   7800
cagagcgcag ataccaaata ctgtccttct agtgtagccg tagttaggcc accacttcaa   7860
gaactctgta gcaccgccta catacctcgc tctgctaatc ctgttaccag tggctgctgc   7920
cagtggcgat aagtcgtgtc ttaccgggtt ggactcaaga cgatagttac cggataaggc   7980
gcagcggtcg ggctgaacgg ggggttcgtg cacacagccc agcttggagc gaacgaccta   8040
caccgaactg agatacctac agcgtgagca ttgagaaagc gccacgcttc ccgaagggag   8100
aaaggcggac aggtatccgg taagcggcag ggtcggaaca ggagagcgca cgagggagct   8160
tccaggggga aacgcctggt atctttatag tcctgtcggg tttcgccacc tctgacttga   8220
gcgtcgattt ttgtgatgct cgtcaggggg gcggagccta tggaaaaacg ccagcaacgc   8280
ggccttttta cggttcctgg ccttttgctg gccttttgct cacatgttct ttcctgcgtt   8340
atcccctgat tctgtggata accgtattac cgcctttgag tgagctgata ccgctcgccg   8400
cagccgaacg accgagcgca gcgagtcagt gagcgaggaa gcggaagagc gcccaatacg   8460
caaaccgcct ctccccgcgc gttggccgat tcattaatgc agctgtggaa tgtgtgtcag   8520
ttagggtgtg gaaagtcccc aggctcccca gcaggcagaa gtatgcaaag catgcatctc   8580
aattagtcag caaccaggtg tggaaagtcc ccaggctccc cagcaggcag aagtatgcaa   8640
agcatgcatc tcaattagtc agcaaccata gtcccgcccc taactccgcc catcccgccc   8700
ctaactccgc ccagttccgc ccattctccg ccccatggct gactaatttt ttttatttat   8760
gcagaggccg aggccgcctc ggcctctgag ctattccaga agtagtgagg aggctttttt   8820
ggaggcctag gcttttgcaa aaagcttgga cacaagacag gcttgcgaga tatgtttgag   8880
aataccactt tatcccgcgt cagggagagg cagtgcgtaa aaagacgcgg actcatgtga   8940
aatactggtt tttagtgcgc cagatctcta taatctcgcg caacctattt tcccctcgaa   9000
cactttttaa gccgtagata aacaggctgg gacacttcac atgagcgaaa aatacatcgt   9060
cacctgggac atgttgcaga tccatgcacg taaactcgca agccgactga tgccttctga   9120
```

```
acaatggaaa ggcattattg ccgtaagccg tggcggtctg taccgggtgc gttactggcg   9180

cgtgaactgg gtattcgtca tgtcgatacc gtttgtattt ccagctacga tcacgacaac   9240

cagcgcgagc ttaaagtgct gaaacgcgca gaaggcgatg gcgaaggctt catcgttatt   9300

gatgacctgg tggataccgg tggtactgcg gttgcgattc gtgaaatgta tccaaaagcg   9360

cactttgtca ccatcttcgc aaaaccggct ggtcgtccgc tggttgatga ctatgttgtt   9420

gatatcccgc aagatacctg gattgaacag ccgtgggata tgggcgtcgt attcgtcccg   9480

ccaatctccg gtcgctaatc ttttcaacgc ctggcactgc cgggcgttgt tctttttaac   9540

ttcaggcggg ttacaatagt ttccagtaag tattctggag gctgcatcca tgacacaggc   9600

aaacctgagc gaaaccctgt tcaaaccccg ctttaaacat cctgaaacct cgacgctagt   9660

ccgccgcttt aatcacggcg cacaaccgcc tgtgcagtcg gcccttgatg gtaaaaccat   9720

ccctcactgg tatcgcatga ttaaccgtct gatgtggatc tggcgcggca ttgacccacg   9780

cgaaatcctc gacgtccagg cacgtattgt gatgagcgat gccgaacgta ccgacgatga   9840

tttatacgat acggtgattg gctaccgtgg cggcaactgg atttatgagt gggccccgga   9900

tctttgtgaa ggaaccttac ttctgtggtg tgacataatt ggacaaacta cctacagaga   9960

tttaaagctc taaggtaaat ataaaatttt taagtgtata atgtgttaaa ctactgattc  10020

taattgtttg tgtattttag attccaacct atggaactga tgaatgggag cagtggtgga  10080

atgcctttaa tgaggaaaac ctgttttgct cagaagaaat gccatctagt gatgatgagg  10140

ctactgctga ctctcaacat tctactcctc caaaaaagaa gagaaaggta gaagacccca  10200

aggactttcc ttcagaattg ctaagttttt tgagtcatgc tgtgtttagt aatagaactc  10260

ttgcttgctt tgctatttac accacaaagg aaaaagctgc actgctatac aagaaaatta  10320

tggaaaaata ttctgtaacc tttataagta ggcataacag ttataatcat aacatactgt  10380

tttttcttac tccacacagg catagagtgt ctgctattaa taactatgct caaaaattgt  10440

gtacctttag ctttttaatt tgtaaagggg ttaataagga atatttgatg tatagtgcct  10500

tgactagaga tcataatcag ccataccaca tttgtagagg ttttacttgc tttaaaaaac  10560

ctcccacacc tccccctgaa cctgaaacat aaaatgaatg caattgttgt tgttaacttg  10620

tttattgcag cttataatgg ttacaaataa agcaatagca tcacaaattt cacaaataaa  10680

gcattttttt cactgcattc tagttgtggt ttgtccaaac tcatcaatgt atcttatcat  10740

gtctggatca actggataac tcaagctaac caaaatcatc ccaaacttcc caccccatac  10800

cctattacca ctgccaatta cctagtggtt tcatttactc taaacctgtg attcctctga  10860

attattttca ttttaaagaa attgtatttg ttaaatatgt actacaaact tagtag      10916
```

```
<210> SEQ ID NO 29
<211> LENGTH: 10931
<212> TYPE: DNA
<213> ORGANISM: Artificial sequence
<220> FEATURE:
<223> OTHER INFORMATION: pWPT-eGFP-F2A-GPC3-28Z

<400> SEQUENCE: 29

ttggaagggc taattcactc ccaaagaaga caagatatcc ttgatctgtg gatctaccac     60

acacaaggct acttccctga ttagcagaac tacacaccag ggccaggggt cagatatcca    120

ctgacctttg gatggtgcta caagctagta ccagttgagc cagataaggt agaagaggcc    180

aataaaggag agaacaccag cttgttacac cctgtgagcc tgcatgggat ggatgacccg    240
```

```
gagagagaag tgttagagtg gaggtttgac agccgcctag catttcatca cgtggcccga    300
gagctgcatc cggagtactt caagaactgc tgatatcgag cttgctacaa gggactttcc    360
gctggggact ttccagggag gcgtggcctg ggcgggactg gggagtggcg agccctcaga    420
tcctgcatat aagcagctgc tttttgcctg tactgggtct ctctggttag accagatctg    480
agcctgggag ctctctggct aactagggaa cccactgctt aagcctcaat aaagcttgcc    540
ttgagtgctt caagtagtgt gtgcccgtct gttgtgtgac tctggtaact agagatccct    600
cagacccttt tagtcagtgt ggaaaatctc tagcagtggc gcccgaacag ggacttgaaa    660
gcgaaaggga aaccagagga gctctctcga cgcaggactc ggcttgctga agcgcgcacg    720
gcaagaggcg aggggcggcg actggtgagt acgccaaaaa ttttgactag cggaggctag    780
aaggagagag atgggtgcga gagcgtcagt attaagcggg ggagaattag atcgcgatgg    840
gaaaaaattc ggttaaggcc agggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg gccgctgatc ttcagacctg gaggaggaga tatgagggac aattggagaa   1200
gtgaattata taaatataaa gtagtaaaaa ttgaaccatt aggagtagca cccaccaagg   1260
caaagagaag agtggtgcag agagaaaaaa gagcagtggg aataggagct ttgttccttg   1320
ggttcttggg agcagcagga agcactatgg gcgcagcgtc aatgacgctg acggtacagg   1380
ccagacaatt attgtctggt atagtgcagc agcagaacaa tttgctgagg gctattgagg   1440
cgcaacagca tctgttgcaa ctcacagtct ggggcatcaa gcagctccag gcaagaatcc   1500
tggctgtgga aagataccta aaggatcaac agctcctggg gatttggggt tgctctggaa   1560
aactcatttg caccactgct gtgccttgga atgctagttg gagtaataaa tctctggaac   1620
agatttggaa tcacacgacc tggatggagt gggacagaga aattaacaat tacacaagct   1680
taatacactc cttaattgaa gaatcgcaaa accagcaaga aaagaatgaa caagaattat   1740
tggaattaga taaatgggca agtttgtgga attggtttaa cataacaaat tggctgtggt   1800
atataaaatt attcataatg atagtaggag gcttggtagg tttaagaata gtttttgctg   1860
tactttctat agtgaataga gttaggcagg gatattcacc attatcgttt cagacccacc   1920
tcccaacccc gaggggaccc gacaggcccg aaggaataga agaagaaggt ggagagagag   1980
acagagacag atccattcga ttagtgaacg gatctcgacg gtatcggtta acttttaaaa   2040
gaaaaggggg gattgggggg tacagtgcag gggaaagaat agtagacata atagcaacag   2100
acatacaaac taaagaatta caaaaacaaa ttacaaaaat tcaaaatttt ccgatcacga   2160
gactagcctc gagaagcttg atcgatggct ccggtgcccg tcagtgggca gagcgcacat   2220
cgcccacagt ccccgagaag ttggggggag gggtcggcaa ttgaaccggt gcctagagaa   2280
ggtggcgcgg ggtaaactgg gaaagtgatg tcgtgtactg gctccgcctt tttcccgagg   2340
gtgggggaga accgtatata agtgcagtag tcgccgtgaa cgttcttttt cgcaacgggt   2400
ttgccgccag aacacaggtg tcgtgacgcg gatccaggcc taagcttacg cgtcctagcg   2460
ctaccggtcg ccaccatggt gagcaagggc gaggagctgt tcaccggggt ggtgcccatc   2520
ctggtcgagc tggacggcga cgtaaacggc cacaagttca gcgtgtccgg cgagggcgag   2580
ggcgatgcca cctacggcaa gctgaccctg aagttcatct gcaccaccgg caagctgccc   2640
```

```
gtgccctggc ccaccctcgt gaccaccctg acctacggcg tgcagtgctt cagccgctac   2700
cccgaccaca tgaagcagca cgacttcttc aagtccgcca tgcccgaagg ctacgtccag   2760
gagcgcacca tcttcttcaa ggacgacggc aactacaaga cccgcgccga ggtgaagttc   2820
gagggcgaca ccctggtgaa ccgcatcgag ctgaagggca tcgacttcaa ggaggacggc   2880
aacatcctgg ggcacaagct ggagtacaac tacaacagcc acaacgtcta tatcatggcc   2940
gacaagcaga agaacggcat caaggtgaac ttcaagatcc gccacaacat cgaggacggc   3000
agcgtgcagc tcgccgacca ctaccagcag aacaccccca tcggcgacgg ccccgtgctg   3060
ctgcccgaca accactacct gagcacccag tccgccctga gcaaagaccc caacgagaag   3120
cgcgatcaca tggtcctgct ggagttcgtg accgccgccg ggatcactct cggcatggac   3180
gagctgtaca agtccggagt gaaacagact ttgaattttg accttctgaa gttggcagga   3240
gacgttgagt ccaaccctgg gcccatggcc ttaccagtga ccgccttgct cctgccgctg   3300
gccttgctgc tccacgccgc caggccggat gttgtgatga ctcagtctcc actctccctg   3360
cccgtcaccc ctggagagcc ggcctccatc tcctgcagat ctagtcagag ccttgtacac   3420
agtaatgcca acacctattt acattggtac ctgcagaagc cagggcagtc tccacagctc   3480
ctgatctata aagtttccaa ccgattttct ggggtccctg acaggttcag tggcagtgga   3540
tcaggcacag attttacact gaaaatcagc agagtggagg ctgaggatgt tggggtttat   3600
tactgctctc aaaatacaca tgttcctcct acgtttggcc aggggaccaa gctggagatc   3660
aaacgtggtg gaggcggttc aggcggaggt ggctctggcg gtggcggatc gcaggtgcag   3720
ctggtgcagt ctggagctga ggtgaagaag cctggggcct cagtgaaggt ctcctgcaag   3780
gcttctggat acaccttcac cgactatgaa atgcactggg tgcgacaggc ccctggacaa   3840
gggcttgagt ggatgggagc tcttgatcct aaaactggtg atactgccta cagtcagaag   3900
ttcaagggca gagtcacgct gaccgcggac gaatccacga gcacagccta catggagctg   3960
agcagcctga gatctgagga cacggccgtg tattactgta caagattcta ctcctatact   4020
tactggggcc agggaaccct ggtcaccgtc tcctcaacca cgacgccagc gccgcgacca   4080
ccaacaccgg cgcccaccat cgcgtcgcag cccctgtccc tgcgcccaga ggcgtgccgg   4140
ccagcggcgg ggggcgcagt gcacacgagg gggctggact tcgcctgtga tttttgggtg   4200
ctggtggtgg ttggtggagt cctggcttgc tatagcttgc tagtaacagt ggcctttatt   4260
attttctggg tgaggagtaa gaggagcagg ctcctgcaca gtgactacat gaacatgact   4320
ccccgccgcc ccgggccaac ccgcaagcat taccagccct atgccccacc acgcgacttc   4380
gcagcctatc gctccagagt gaagttcagc aggagcgcag acgcccccgc gtaccagcag   4440
ggccagaacc agctctataa cgagctcaat ctaggacgaa gagaggagta cgatgttttg   4500
gacaagagac gtggccggga ccctgagatg gggggaaagc cgcagagaag gaagaaccct   4560
caggaaggcc tgtacaatga actgcagaaa gataagatgg cggaggccta cagtgagatt   4620
gggatgaaag gcgagcgccg gaggggcaag gggcacgatg gcctttacca gggtctcagt   4680
acagccacca aggacaccta cgacgccctt cacatgcagg ccctgccccc tcgctaggtc   4740
gacctcgagg gaattccgat aatcaacctc tggattacaa aatttgtgaa agattgactg   4800
gtattcttaa ctatgttgct ccttttacgc tatgtggata cgctgcttta atgcctttgt   4860
atcatgctat tgcttcccgt atggctttca ttttctcctc cttgtataaa tcctggttgc   4920
tgtctcttta tgaggagttg tggcccgttg tcaggcaacg tggcgtggtg tgcactgtgt   4980
```

```
ttgctgacgc aacccccact ggttggggca ttgccaccac ctgtcagctc ctttccggga   5040
ctttcgcttt ccccctccct attgccacgg cggaactcat cgccgcctgc cttgcccgct   5100
gctggacagg ggctcggctg ttgggcactg acaattccgt ggtgttgtcg gggaagctga   5160
cgtcctttcc atggctgctc gcctgtgttg ccacctggat tctgcgcggg acgtccttct   5220
gctacgtccc ttcggccctc aatccagcgg accttccttc ccgcggcctg ctgccggctc   5280
tgcggcctct tccgcgtctt cgccttcgcc ctcagacgag tcggatctcc ctttgggccg   5340
cctccccgca tcgggaattc gagctcggta cctttaagac caatgactta caaggcagct   5400
gtagatctta gccacttttt aaaagaaaag gggggactgg aagggctaat tcactcccaa   5460
cgaagacaag atgggatcaa ttcaccatgg gaataacttc gtatagcata cattatacga   5520
agttatgctg ctttttgctt gtactgggtc tctctggtta gaccagatct gagcctggga   5580
gctctctggc taactaggga acccactgct taagcctcaa taaagcttgc cttgagtgct   5640
tcaagtagtg tgtgcccgtc tgttgtgtga ctctggtaac tagagatccc tcagaccctt   5700
ttagtcagtg tggaaaatct ctagcagcat ctagaattaa ttccgtgtat tctatagtgt   5760
cacctaaatc gtatgtgtat gatacataag gttatgtatt aattgtagcc gcgttctaac   5820
gacaatatgt acaagcctaa ttgtgtagca tctggcttac tgaagcagac cctatcatct   5880
ctctcgtaaa ctgccgtcag agtcggtttg gttggacgaa ccttctgagt ttctggtaac   5940
gccgtcccgc acccggaaat ggtcagcgaa ccaatcagca gggtcatcgc tagccagatc   6000
ctctacgccg gacgcatcgt ggccggcatc accggcgcca caggtgcggt tgctggcgcc   6060
tatatcgccg acatcaccga tggggaagat cgggctcgcc acttcgggct catgagcgct   6120
tgtttcggcg tgggtatggt ggcaggcccc gtggccgggg gactgttggg cgccatctcc   6180
ttgcatgcac cattccttgc ggcggcggtg ctcaacggcc tcaacctact actgggctgc   6240
ttcctaatgc aggagtcgca taagggagag cgtcgaatgg tgcactctca gtacaatctg   6300
ctctgatgcc gcatagttaa gccagccccg acacccgcca acacccgctg acgcgccctg   6360
acgggcttgt ctgctcccgg catccgctta cagacaagct gtgaccgtct ccgggagctg   6420
catgtgtcag aggttttcac cgtcatcacc gaaacgcgcg agacgaaagg gcctcgtgat   6480
acgcctattt ttataggtta atgtcatgat aataatggtt tcttagacgt caggtggcac   6540
ttttcgggga aatgtgcgcg gaacccctat ttgtttattt ttctaaatac attcaaatat   6600
gtatccgctc atgagacaat aaccctgata aatgcttcaa taatattgaa aaaggaagag   6660
tatgagtatt caacatttcc gtgtcgccct tattcccttt tttgcggcat tttgccttcc   6720
tgtttttgct cacccagaaa cgctggtgaa agtaaaagat gctgaagatc agttgggtgc   6780
acgagtgggt tacatcgaac tggatctcaa cagcggtaag atccttgaga gttttcgccc   6840
cgaagaacgt tttccaatga tgagcacttt taaagttctg ctatgtggcg cggtattatc   6900
ccgtattgac gccgggcaag agcaactcgg tcgccgcata cactattctc agaatgactt   6960
ggttgagtac tcaccagtca cagaaaagca tcttacggat ggcatgacag taagagaatt   7020
atgcagtgct gccataacca tgagtgataa cactgcggcc aacttacttc tgacaacgat   7080
cggaggaccg aaggagctaa ccgctttttt gcacaacatg ggggatcatg taactcgcct   7140
tgatcgttgg gaaccggagc tgaatgaagc cataccaaac gacgagcgtg acaccacgat   7200
gcctgtagca atggcaacaa cgttgcgcaa actattaact ggcgaactac ttactctagc   7260
ttcccggcaa caattaatag actggatgga ggcggataaa gttgcaggac cacttctgcg   7320
ctcggccctt ccggctggct ggtttattgc tgataaatct ggagccggtg agcgtgggtc   7380
```

```
tcgcggtatc attgcagcac tggggccaga tggtaagccc tcccgtatcg tagttatcta   7440
cacgacgggg agtcaggcaa ctatggatga acgaaataga cagatcgctg agataggtgc   7500
ctcactgatt aagcattggt aactgtcaga ccaagtttac tcatatatac tttagattga   7560
tttaaaactt catttttaat ttaaaaggat ctaggtgaag atcctttttg ataatctcat   7620
gaccaaaatc ccttaacgtg agttttcgtt ccactgagcg tcagaccccg tagaaaagat   7680
caaaggatct tcttgagatc ctttttttct gcgcgtaatc tgctgcttgc aaacaaaaaa   7740
accaccgcta ccagcggtgg tttgtttgcc ggatcaagag ctaccaactc tttttccgaa   7800
ggtaactggc ttcagcagag cgcagatacc aaatactgtc cttctagtgt agccgtagtt   7860
aggccaccac ttcaagaact ctgtagcacc gcctacatac ctcgctctgc taatcctgtt   7920
accagtggct gctgccagtg gcgataagtc gtgtcttacc gggttggact caagacgata   7980
gttaccggat aaggcgcagc ggtcgggctg aacggggggt tcgtgcacac agcccagctt   8040
ggagcgaacg acctacaccg aactgagata cctacagcgt gagcattgag aaagcgccac   8100
gcttcccgaa gggagaaagg cggacaggta tccggtaagc ggcagggtcg gaacaggaga   8160
gcgcacgagg gagcttccag ggggaaacgc ctggtatctt tatagtcctg tcgggtttcg   8220
ccacctctga cttgagcgtc gatttttgtg atgctcgtca ggggggcgga gcctatggaa   8280
aaacgccagc aacgcggcct ttttacggtt cctggccttt tgctggcctt ttgctcacat   8340
gttctttcct gcgttatccc ctgattctgt ggataaccgt attaccgcct ttgagtgagc   8400
tgataccgct cgccgcagcc gaacgaccga gcgcagcgag tcagtgagcg aggaagcgga   8460
agagcgccca atacgcaaac cgcctctccc cgcgcgttgg ccgattcatt aatgcagctg   8520
tggaatgtgt gtcagttagg gtgtggaaag tccccaggct ccccagcagg cagaagtatg   8580
caaagcatgc atctcaatta gtcagcaacc aggtgtggaa agtccccagg ctccccagca   8640
ggcagaagta tgcaaagcat gcatctcaat tagtcagcaa ccatagtccc gcccctaact   8700
ccgcccatcc cgcccctaac tccgcccagt tccgcccatt ctccgcccca tggctgacta   8760
atttttttta tttatgcaga ggccgaggcc gcctcggcct ctgagctatt ccagaagtag   8820
tgaggaggct tttttggagg cctaggcttt tgcaaaaagc ttggacacaa gacaggcttg   8880
cgagatatgt ttgagaatac cactttatcc cgcgtcaggg agaggcagtg cgtaaaaaga   8940
cgcggactca tgtgaaatac tggtttttag tgcgccagat ctctataatc tcgcgcaacc   9000
tattttcccc tcgaacactt tttaagccgt agataaacag gctgggacac ttcacatgag   9060
cgaaaaatac atcgtcacct gggacatgtt gcagatccat gcacgtaaac tcgcaagccg   9120
actgatgcct tctgaacaat ggaaaggcat tattgccgta agccgtggcg gtctgtaccg   9180
ggtgcgttac tggcgcgtga actgggtatt cgtcatgtcg ataccgtttg tatttccagc   9240
tacgatcacg acaaccagcg cgagcttaaa gtgctgaaac gcgcagaagg cgatggcgaa   9300
ggcttcatcg ttattgatga cctggtggat accggtggta ctgcggttgc gattcgtgaa   9360
atgtatccaa aagcgcactt tgtcaccatc ttcgcaaaac cggctggtcg tccgctggtt   9420
gatgactatg ttgttgatat cccgcaagat acctggattg aacagccgtg ggatatgggc   9480
gtcgtattcg tcccgccaat ctccggtcgc taatcttttc aacgcctggc actgccgggc   9540
gttgttcttt ttaacttcag gcgggttaca atagtttcca gtaagtattc tggaggctgc   9600
atccatgaca caggcaaacc tgagcgaaac cctgttcaaa ccccgcttta aacatcctga   9660
aacctcgacg ctagtccgcc gctttaatca cggcgcacaa ccgcctgtgc agtcggccct   9720
```

```
tgatggtaaa accatccctc actggtatcg catgattaac cgtctgatgt ggatctggcg   9780

cggcattgac ccacgcgaaa tcctcgacgt ccaggcacgt attgtgatga gcgatgccga   9840

acgtaccgac gatgatttat acgatacggt gattggctac cgtggcggca actggattta   9900

tgagtgggcc ccggatcttt gtgaaggaac cttacttctg tggtgtgaca taattggaca   9960

aactacctac agagatttaa agctctaagg taaatataaa atttttaagt gtataatgtg  10020

ttaaactact gattctaatt gtttgtgtat tttagattcc aacctatgga actgatgaat  10080

gggagcagtg gtggaatgcc tttaatgagg aaaacctgtt ttgctcagaa gaaatgccat  10140

ctagtgatga tgaggctact gctgactctc aacattctac tcctccaaaa aagaagagaa  10200

aggtagaaga ccccaaggac tttccttcag aattgctaag tttttgagt catgctgtgt  10260

ttagtaatag aactcttgct tgctttgcta tttacaccac aaaggaaaaa gctgcactgc  10320

tatacaagaa aattatggaa aaatattctg taacctttat aagtaggcat aacagttata  10380

atcataacat actgtttttt cttactccac acaggcatag agtgtctgct attaataact  10440

atgctcaaaa attgtgtacc tttagctttt taatttgtaa aggggttaat aaggaatatt  10500

tgatgtatag tgccttgact agagatcata atcagccata ccacatttgt agaggtttta  10560

cttgctttaa aaaacctccc acacctcccc ctgaacctga aacataaaat gaatgcaatt  10620

gttgttgtta acttgtttat tgcagcttat aatggttaca aataaagcaa tagcatcaca  10680

aatttcacaa ataaagcatt tttttcactg cattctagtt gtggtttgtc caaactcatc  10740

aatgtatctt atcatgtctg gatcaactgg ataactcaag ctaaccaaaa tcatcccaaa  10800

cttcccaccc catacctat taccactgcc aattacctag tggtttcatt tactctaaac  10860

ctgtgattcc tctgaattat tttcatttta aagaaattgt atttgttaaa tatgtactac  10920

aaacttagta g                                                       10931
```

<210> SEQ ID NO 30
<211> LENGTH: 11057
<212> TYPE: DNA
<213> ORGANISM: Artificial sequence
<220> FEATURE:
<223> OTHER INFORMATION: pWPT-eGFP-F2A-GPC3-28BBZ

<400> SEQUENCE: 30

```
ttggaagggc taattcactc ccaaagaaga caagatatcc ttgatctgtg gatctaccac     60

acacaaggct acttccctga ttagcagaac tacacaccag ggccaggggt cagatatcca    120

ctgacctttg gatggtgcta caagctagta ccagttgagc cagataaggt agaagaggcc    180

aataaaggag agaacaccag cttgttacac cctgtgagcc tgcatgggat ggatgacccg    240

gagagagaag tgttagagtg gaggtttgac agccgcctag catttcatca cgtggcccga    300

gagctgcatc cggagtactt caagaactgc tgatatcgag cttgctacaa gggactttcc    360

gctggggact ttccagggag gcgtggcctg ggcgggactg gggagtggcg agccctcaga    420

tcctgcatat aagcagctgc tttttgcctg tactgggtct ctctggttag accagatctg    480

agcctgggag ctctctggct aactagggaa cccactgctt aagcctcaat aaagcttgcc    540

ttgagtgctt caagtagtgt gtgcccgtct gttgtgtgac tctggtaact agagatccct    600

cagacccttt tagtcagtgt ggaaaatctc tagcagtggc gcccgaacag ggacttgaaa    660

gcgaaaggga aaccagagga gctctctcga cgcaggactc ggcttgctga agcgcgcacg    720

gcaagaggcg aggggcggcg actggtgagt acgccaaaaa ttttgactag cggaggctag    780

aaggagagag atgggtgcga gagcgtcagt attaagcggg ggagaattag atcgcgatgg    840
```

```
gaaaaaattc ggttaaggcc agggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg gccgctgatc ttcagacctg gaggaggaga tatgagggac aattggagaa   1200
gtgaattata taaatataaa gtagtaaaaa ttgaaccatt aggagtagca cccaccaagg   1260
caaagagaag agtggtgcag agagaaaaaa gagcagtggg aataggagct ttgttccttg   1320
ggttcttggg agcagcagga agcactatgg gcgcagcgtc aatgacgctg acggtacagg   1380
ccagacaatt attgtctggt atagtgcagc agcagaacaa tttgctgagg gctattgagg   1440
cgcaacagca tctgttgcaa ctcacagtct ggggcatcaa gcagctccag gcaagaatcc   1500
tggctgtgga aagataccta aaggatcaac agctcctggg gatttggggt tgctctggaa   1560
aactcatttg caccactgct gtgccttgga atgctagttg gagtaataaa tctctggaac   1620
agatttggaa tcacacgacc tggatggagt gggacagaga aattaacaat tacacaagct   1680
taatacactc cttaattgaa gaatcgcaaa accagcaaga aaagaatgaa caagaattat   1740
tggaattaga taaatgggca agtttgtgga attggtttaa cataacaaat tggctgtggt   1800
atataaaatt attcataatg atagtaggag gcttggtagg tttaagaata gtttttgctg   1860
tactttctat agtgaataga gttaggcagg gatattcacc attatcgttt cagacccacc   1920
tcccaacccc gaggggaccc gacaggcccg aaggaataga agaagaaggt ggagagagag   1980
acagagacag atccattcga ttagtgaacg gatctcgacg gtatcggtta acttttaaaa   2040
gaaaaggggg gattgggggg tacagtgcag gggaaagaat agtagacata atagcaacag   2100
acatacaaac taaagaatta caaaaacaaa ttacaaaaat tcaaaatttt ccgatcacga   2160
gactagcctc gagaagcttg atcgatggct ccggtgcccg tcagtgggca gagcgcacat   2220
cgcccacagt ccccgagaag ttggggggag gggtcggcaa ttgaaccggt gcctagagaa   2280
ggtggcgcgg ggtaaactgg gaaagtgatg tcgtgtactg gctccgcctt tttcccgagg   2340
gtgggggaga accgtatata agtgcagtag tcgccgtgaa cgttcttttt cgcaacgggt   2400
ttgccgccag aacacaggtg tcgtgacgcg gatccaggcc taagcttacg cgtcctagcg   2460
ctaccggtcg ccaccatggt gagcaagggc gaggagctgt tcaccggggt ggtgcccatc   2520
ctggtcgagc tggacggcga cgtaaacggc cacaagttca gcgtgtccgg cgagggcgag   2580
ggcgatgcca cctacggcaa gctgaccctg aagttcatct gcaccaccgg caagctgccc   2640
gtgccctggc ccaccctcgt gaccaccctg acctacggcg tgcagtgctt cagccgctac   2700
cccgaccaca tgaagcagca cgacttcttc aagtccgcca tgcccgaagg ctacgtccag   2760
gagcgcacca tcttcttcaa ggacgacggc aactacaaga cccgcgccga ggtgaagttc   2820
gagggcgaca ccctggtgaa ccgcatcgag ctgaagggca tcgacttcaa ggaggacggc   2880
aacatcctgg ggcacaagct ggagtacaac tacaacagcc acaacgtcta tatcatggcc   2940
gacaagcaga agaacggcat caaggtgaac ttcaagatcc gccacaacat cgaggacggc   3000
agcgtgcagc tcgccgacca ctaccagcag aacaccccca tcggcgacgg ccccgtgctg   3060
ctgcccgaca accactacct gagcacccag tccgccctga gcaaagaccc caacgagaag   3120
cgcgatcaca tggtcctgct ggagttcgtg accgccgccg ggatcactct cggcatggac   3180
```

```
gagctgtaca agtccggagt gaaacagact ttgaattttg accttctgaa gttggcagga   3240
gacgttgagt ccaaccctgg gcccatggcc ttaccagtga ccgccttgct cctgccgctg   3300
gccttgctgc tccacgccgc caggccggat gttgtgatga ctcagtctcc actctccctg   3360
cccgtcaccc ctggagagcc ggcctccatc tcctgcagat ctagtcagag ccttgtacac   3420
agtaatgcca acacctattt acattggtac ctgcagaagc cagggcagtc tccacagctc   3480
ctgatctata aagtttccaa ccgattttct ggggtccctg acaggttcag tggcagtgga   3540
tcaggcacag attttacact gaaaatcagc agagtggagg ctgaggatgt tggggtttat   3600
tactgctctc aaaatacaca tgttcctcct acgtttggcc aggggaccaa gctggagatc   3660
aaacgtggtg gaggcggttc aggcggaggt ggctctggcg gtggcggatc gcaggtgcag   3720
ctggtgcagt ctggagctga ggtgaagaag cctggggcct cagtgaaggt ctcctgcaag   3780
gcttctggat acaccttcac cgactatgaa atgcactggg tgcgacaggc ccctggacaa   3840
gggcttgagt ggatgggagc tcttgatcct aaaactggtg atactgccta cagtcagaag   3900
ttcaagggca gagtcacgct gaccgcggac gaatccacga gcacagccta catggagctg   3960
agcagcctga gatctgagga cacggccgtg tattactgta caagattcta ctcctatact   4020
tactggggcc agggaaccct ggtcaccgtc tcctcaacca cgacgccagc gccgcgacca   4080
ccaacaccgg cgcccaccat cgcgtcgcag cccctgtccc tgcgcccaga ggcgtgccgg   4140
ccagcggcgg ggggcgcagt gcacacgagg gggctggact tcgcctgtga tttttgggtg   4200
ctggtggtgg ttggtggagt cctggcttgc tatagcttgc tagtaacagt ggcctttatt   4260
attttctggg tgaggagtaa gaggagcagg ctcctgcaca gtgactacat gaacatgact   4320
ccccgccgcc ccgggccaac ccgcaagcat taccagccct atgccccacc acgcgacttc   4380
gcagcctatc gctccaaacg gggcagaaag aaactcctgt atatattcaa acaaccattt   4440
atgagaccag tacaaactac tcaagaggaa gatggctgta gctgccgatt tccagaagaa   4500
gaagaaggag gatgtgaact gagagtgaag ttcagcagga gcgcagacgc ccccgcgtac   4560
cagcagggcc agaaccagct ctataacgag ctcaatctag gacgaagaga ggagtacgat   4620
gttttggaca agagacgtgg ccgggaccct gagatggggg gaaagccgca gagaaggaag   4680
aaccctcagg aaggcctgta caatgaactg cagaaagata agatggcgga ggcctacagt   4740
gagattggga tgaaaggcga gcgccggagg ggcaaggggc acgatggcct ttaccagggt   4800
ctcagtacag ccaccaagga cacctacgac gcccttcaca tgcaggccct gccccctcgc   4860
taggtcgacc tcgagggaat tccgataatc aacctctgga ttacaaaatt tgtgaaagat   4920
tgactggtat tcttaactat gttgctcctt ttacgctatg tggatacgct gctttaatgc   4980
ctttgtatca tgctattgct tcccgtatgg ctttcatttt ctcctccttg tataaatcct   5040
ggttgctgtc tctttatgag gagttgtggc ccgttgtcag gcaacgtggc gtggtgtgca   5100
ctgtgtttgc tgacgcaacc cccactggtt ggggcattgc caccacctgt cagctccttt   5160
ccgggacttt cgctttcccc ctccctattg ccacggcgga actcatcgcc gcctgccttg   5220
cccgctgctg gacaggggct cggctgttgg gcactgacaa ttccgtggtg ttgtcgggga   5280
agctgacgtc ctttccatgg ctgctcgcct gtgttgccac ctggattctg cgcgggacgt   5340
ccttctgcta cgtcccttcg gccctcaatc cagcggacct tccttcccgc ggcctgctgc   5400
cggctctgcg gcctcttccg cgtcttcgcc ttcgccctca gacgagtcgg atctcccttt   5460
gggccgcctc cccgcatcgg gaattcgagc tcggtacctt taagaccaat gacttacaag   5520
gcagctgtag atcttagcca ctttttaaaa gaaaaggggg gactggaagg gctaattcac   5580
```

```
tcccaacgaa gacaagatgg gatcaattca ccatgggaat aacttcgtat agcatacatt   5640
atacgaagtt atgctgcttt ttgcttgtac tgggtctctc tggttagacc agatctgagc   5700
ctgggagctc tctggctaac tagggaaccc actgcttaag cctcaataaa gcttgccttg   5760
agtgcttcaa gtagtgtgtg cccgtctgtt gtgtgactct ggtaactaga gatccctcag   5820
acccttttag tcagtgtgga aaatctctag cagcatctag aattaattcc gtgtattcta   5880
tagtgtcacc taaatcgtat gtgtatgata cataaggtta tgtattaatt gtagccgcgt   5940
tctaacgaca atatgtacaa gcctaattgt gtagcatctg gcttactgaa gcagacccta   6000
tcatctctct cgtaaactgc cgtcagagtc ggtttggttg gacgaacctt ctgagtttct   6060
ggtaacgccg tcccgcaccc ggaaatggtc agcgaaccaa tcagcagggt catcgctagc   6120
cagatcctct acgccggacg catcgtggcc ggcatcaccg gcgccacagg tgcggttgct   6180
ggcgcctata tcgccgacat caccgatggg gaagatcggg ctcgccactt cgggctcatg   6240
agcgcttgtt tcggcgtggg tatggtggca ggccccgtgg ccgggggact gttgggcgcc   6300
atctccttgc atgcaccatt ccttgcggcg gcggtgctca acggcctcaa cctactactg   6360
ggctgcttcc taatgcagga gtcgcataag ggagagcgtc gaatggtgca ctctcagtac   6420
aatctgctct gatgccgcat agttaagcca gccccgacac ccgccaacac ccgctgacgc   6480
gccctgacgg gcttgtctgc tcccggcatc cgcttacaga caagctgtga ccgtctccgg   6540
gagctgcatg tgtcagaggt tttcaccgtc atcaccgaaa cgcgcgagac gaaagggcct   6600
cgtgatacgc ctatttttat aggttaatgt catgataata atggtttctt agacgtcagg   6660
tggcactttt cggggaaatg tgcgcggaac ccctatttgt ttatttttct aaatacattc   6720
aaatatgtat ccgctcatga gacaataacc ctgataaatg cttcaataat attgaaaaag   6780
gaagagtatg agtattcaac atttccgtgt cgcccttatt cccttttttg cggcattttg   6840
ccttcctgtt tttgctcacc cagaaacgct ggtgaaagta aaagatgctg aagatcagtt   6900
gggtgcacga gtgggttaca tcgaactgga tctcaacagc ggtaagatcc ttgagagttt   6960
tcgccccgaa gaacgttttc caatgatgag cacttttaaa gttctgctat gtggcgcggt   7020
attatcccgt attgacgccg ggcaagagca actcggtcgc cgcatacact attctcagaa   7080
tgacttggtt gagtactcac cagtcacaga aaagcatctt acggatggca tgacagtaag   7140
agaattatgc agtgctgcca taaccatgag tgataacact gcggccaact tacttctgac   7200
aacgatcgga ggaccgaagg agctaaccgc ttttttgcac aacatggggg atcatgtaac   7260
tcgccttgat cgttgggaac cggagctgaa tgaagccata ccaaacgacg agcgtgacac   7320
cacgatgcct gtagcaatgg caacaacgtt gcgcaaacta ttaactggcg aactacttac   7380
tctagcttcc cggcaacaat taatagactg gatggaggcg gataaagttg caggaccact   7440
tctgcgctcg gcccttccgg ctggctggtt tattgctgat aaatctggag ccggtgagcg   7500
tgggtctcgc ggtatcattg cagcactggg gccagatggt aagccctccc gtatcgtagt   7560
tatctacacg acggggagtc aggcaactat ggatgaacga aatagacaga tcgctgagat   7620
aggtgcctca ctgattaagc attggtaact gtcagaccaa gtttactcat atatacttta   7680
gattgattta aaacttcatt tttaatttaa aaggatctag gtgaagatcc tttttgataa   7740
tctcatgacc aaaatccctt aacgtgagtt ttcgttccac tgagcgtcag accccgtaga   7800
aaagatcaaa ggatcttctt gagatccttt ttttctgcgc gtaatctgct gcttgcaaac   7860
aaaaaaacca ccgctaccag cggtggtttg tttgccggat caagagctac caactctttt   7920
```

```
tccgaaggta actggcttca gcagagcgca gataccaaat actgtccttc tagtgtagcc   7980
gtagttaggc caccacttca agaactctgt agcaccgcct acatacctcg ctctgctaat   8040
cctgttacca gtggctgctg ccagtggcga taagtcgtgt cttaccgggt tggactcaag   8100
acgatagtta ccggataagg cgcagcggtc gggctgaacg gggggttcgt gcacacagcc   8160
cagcttggag cgaacgacct acaccgaact gagataccta cagcgtgagc attgagaaag   8220
cgccacgctt cccgaaggga gaaaggcgga caggtatccg gtaagcggca gggtcggaac   8280
aggagagcgc acgagggagc ttccaggggg aaacgcctgg tatctttata gtcctgtcgg   8340
gtttcgccac ctctgacttg agcgtcgatt tttgtgatgc tcgtcagggg ggcggagcct   8400
atggaaaaac gccagcaacg cggccttttt acggttcctg gccttttgct ggccttttgc   8460
tcacatgttc tttcctgcgt tatcccctga ttctgtggat aaccgtatta ccgcctttga   8520
gtgagctgat accgctcgcc gcagccgaac gaccgagcgc agcgagtcag tgagcgagga   8580
agcggaagag cgcccaatac gcaaaccgcc tctccccgcg cgttggccga ttcattaatg   8640
cagctgtgga atgtgtgtca gttagggtgt ggaaagtccc caggctcccc agcaggcaga   8700
agtatgcaaa gcatgcatct caattagtca gcaaccaggt gtggaaagtc cccaggctcc   8760
ccagcaggca gaagtatgca aagcatgcat ctcaattagt cagcaaccat agtcccgccc   8820
ctaactccgc ccatcccgcc cctaactccg cccagttccg cccattctcc gccccatggc   8880
tgactaattt tttttattta tgcagaggcc gaggccgcct cggcctctga gctattccag   8940
aagtagtgag gaggcttttt tggaggccta ggcttttgca aaaagcttgg acacaagaca   9000
ggcttgcgag atatgtttga gaataccact ttatcccgcg tcagggagag gcagtgcgta   9060
aaaagacgcg gactcatgtg aaatactggt ttttagtgcg ccagatctct ataatctcgc   9120
gcaacctatt ttcccctcga acacttttta agccgtagat aaacaggctg ggacacttca   9180
catgagcgaa aaatacatcg tcacctggga catgttgcag atccatgcac gtaaactcgc   9240
aagccgactg atgccttctg aacaatggaa aggcattatt gccgtaagcc gtggcggtct   9300
gtaccgggtg cgttactggc gcgtgaactg ggtattcgtc atgtcgatac cgtttgtatt   9360
tccagctacg atcacgacaa ccagcgcgag cttaaagtgc tgaaacgcgc agaaggcgat   9420
ggcgaaggct tcatcgttat tgatgacctg gtggataccg gtggtactgc ggttgcgatt   9480
cgtgaaatgt atccaaaagc gcactttgtc accatcttcg caaaaccggc tggtcgtccg   9540
ctggttgatg actatgttgt tgatatcccg caagatacct ggattgaaca gccgtgggat   9600
atgggcgtcg tattcgtccc gccaatctcc ggtcgctaat cttttcaacg cctggcactg   9660
ccgggcgttg ttctttttaa cttcaggcgg gttacaatag tttccagtaa gtattctgga   9720
ggctgcatcc atgacacagg caaacctgag cgaaaccctg ttcaaacccc gctttaaaca   9780
tcctgaaacc tcgacgctag tccgccgctt taatcacggc gcacaaccgc ctgtgcagtc   9840
ggcccttgat ggtaaaacca tccctcactg gtatcgcatg attaaccgtc tgatgtggat   9900
ctggcgcggc attgacccac gcgaaatcct cgacgtccag gcacgtattg tgatgagcga   9960
tgccgaacgt accgacgatg atttatacga tacggtgatt ggctaccgtg gcggcaactg  10020
gatttatgag tgggccccgg atctttgtga aggaacctta cttctgtggt gtgacataat  10080
tggacaaact acctacagag atttaaagct ctaaggtaaa tataaaattt ttaagtgtat  10140
aatgtgttaa actactgatt ctaattgttt gtgtatttta gattccaacc tatggaactg  10200
atgaatggga gcagtggtgg aatgccttta atgaggaaaa cctgttttgc tcagaagaaa  10260
tgccatctag tgatgatgag gctactgctg actctcaaca ttctactcct ccaaaaaaga  10320
```

```
agagaaaggt agaagacccc aaggactttc cttcagaatt gctaagtttt ttgagtcatg  10380
ctgtgtttag taatagaact cttgcttgct ttgctattta caccacaaag gaaaaagctg  10440
cactgctata caagaaaatt atggaaaaat attctgtaac ctttataagt aggcataaca  10500
gttataatca taacatactg tttttctta ctccacacag gcatagagtg tctgctatta  10560
ataactatgc tcaaaaattg tgtaccttta gctttttaat ttgtaaaggg gttaataagg  10620
aatatttgat gtatagtgcc ttgactagag atcataatca gccataccac atttgtagag  10680
gttttacttg ctttaaaaaa cctcccacac ctccccctga acctgaaaca taaaatgaat  10740
gcaattgttg ttgttaactt gtttattgca gcttataatg gttacaaata aagcaatagc  10800
atcacaaatt tcacaaataa agcatttttt tcactgcatt ctagttgtgg tttgtccaaa  10860
ctcatcaatg tatcttatca tgtctggatc aactggataa ctcaagctaa ccaaaatcat  10920
cccaaacttc ccaccccata ccctattacc actgccaatt acctagtggt ttcatttact  10980
ctaaacctgt gattcctctg aattattttc attttaaaga aattgtattt gttaaatatg  11040
tactacaaac ttagtag                                                 11057
```

```
<210> SEQ ID NO 31
<211> LENGTH: 1815
<212> TYPE: DNA
<213> ORGANISM: Artificial sequence
<220> FEATURE:
<223> OTHER INFORMATION: eGFP-GPC-delta Z

<400> SEQUENCE: 31
```

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtcc    720
ggagtgaaac agactttgaa ttttgacctt ctgaagttgg caggagacgt tgagtccaac    780
cctgggccca tggccttacc agtgaccgcc ttgctcctgc cgctggcctt gctgctccac    840
gccgccaggc cggatgttgt gatgactcag tctccactct ccctgcccgt cacccctgga    900
gagccggcct ccatctcctg cagatctagt cagagccttg tacacagtaa tgccaacacc    960
tatttacatt ggtacctgca gaagccaggg cagtctccac agctcctgat ctataaagtt   1020
tccaaccgat tttctggggt ccctgacagg ttcagtggca gtggatcagg cacagatttt   1080
acactgaaaa tcagcagagt ggaggctgag gatgttgggg tttattactg ctctcaaaat   1140
acacatgttc ctcctacgtt tggccagggg accaagctgg agatcaaacg tggtggaggc   1200
ggttcaggcg gaggtggctc tggcggtggc ggatcgcagg tgcagctggt gcagtctgga   1260
```

```
gctgaggtga agaagcctgg ggcctcagtg aaggtctcct gcaaggcttc tggatacacc   1320

ttcaccgact atgaaatgca ctgggtgcga caggcccctg gacaagggct tgagtggatg   1380

ggagctcttg atcctaaaac tggtgatact gcctacagtc agaagttcaa gggcagagtc   1440

acgctgaccg cggacgaatc cacgagcaca gcctacatgg agctgagcag cctgagatct   1500

gaggacacgg ccgtgtatta ctgtacaaga ttctactcct atacttactg gggccaggga   1560

accctggtca ccgtctcctc aaccacgacg ccagcgccgc gaccaccaac accggcgccc   1620

accatcgcgt cgcagcccct gtccctgcgc ccagaggcgt gccggccagc ggcggggggc   1680

gcagtgcaca cgagggggct ggacttcgcc tgtgatatct acatctgggc gcccttggcc   1740

gggacttgtg gggtccttct cctgtcactg gttatcacca gagtgaagtt cagcaggagc   1800

gcagacgccc ccgcg                                                    1815
```

```
<210> SEQ ID NO 32
<211> LENGTH: 321
<212> TYPE: PRT
<213> ORGANISM: Artificial sequence
<220> FEATURE:
<223> OTHER INFORMATION: GPC3-deltaZ protein

<400> SEQUENCE: 32

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
```

-continued

```
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Arg Val Lys Phe Ser Arg Ser Ala Asp Ala Pro
305                 310                 315                 320

Ala
```